(12) United States Patent
Burger et al.

(10) Patent No.: US 9,510,885 B2
(45) Date of Patent: Dec. 6, 2016

(54) STEERABLE AND CURVABLE CAVITY CREATION SYSTEM

(71) Applicant: Osseon LLC, Granby, CT (US)

(72) Inventors: Keith Burger, San Francisco, CA (US); Joshua Cheatwood, Windsor, CA (US); Shixin Chen, Santa Rosa, CA (US)

(73) Assignee: Osseon LLC, Granby, CT (US)

( * ) Notice: Subject to any disclaimer, the term of this patent is extended or adjusted under 35 U.S.C. 154(b) by 292 days.

(21) Appl. No.: 13/736,871

(22) Filed: Jan. 8, 2013

(65) Prior Publication Data

US 2013/0345709 A1  Dec. 26, 2013

Related U.S. Application Data

(63) Continuation of application No. 13/461,727, filed on May 1, 2012, now abandoned, which is a continuation-in-part of application No. 13/182,335, filed on Jul. 13, 2011, which is a continuation of application No. 12/954,511, filed on Nov. 24, 2010, now abandoned, which is a continuation-in-part of application No. 12/469,654, filed on May 20, 2009, now abandoned, which is a continuation-in-part of application No. 12/029,428, filed on Feb. 11, 2008, (Continued)

(51) Int. Cl.
*A61B 17/88* (2006.01)
*A61B 17/00* (2006.01)

(52) U.S. Cl.
CPC ......... *A61B 17/8811* (2013.01); *A61B 17/885* (2013.01); *A61B 17/8805* (2013.01); *A61B 17/8852* (2013.01); *A61B 17/8855* (2013.01); *A61B 17/8858* (2013.01); *A61B 17/8827* (2013.01); *A61B 2017/00309* (2013.01); *A61B 2017/00323* (2013.01); *A61B 2017/00331* (2013.01)

(58) Field of Classification Search
USPC ...................................... 606/79, 92–94, 105
See application file for complete search history.

(56) References Cited

U.S. PATENT DOCUMENTS

| 2,688,329 A | 9/1954 | Wallace |
| 3,503,385 A | 3/1970 | Stevens |

(Continued)

FOREIGN PATENT DOCUMENTS

| WO | 9613297 | 5/1996 |
| WO | 9620752 | 7/1996 |

(Continued)

OTHER PUBLICATIONS

US 7,063,700, 06/2006, Michelson (withdrawn)

(Continued)

*Primary Examiner* — Nicholas Woodall
(74) *Attorney, Agent, or Firm* — Reed Smith LLP

(57) ABSTRACT

Methods and devices for augmenting bone, such as in performing vertebroplasty are disclosed. A bone cement injection needle is provided, having a laterally deflectable distal end. Systems are also disclosed, including the steerable and curvable injection needle, introducer and stylet. The system can also include various exit ports that can be configured with clog-resistant features, such as an obturator. Steerable cavity creation systems and methods are also disclosed.

8 Claims, 55 Drawing Sheets

Related U.S. Application Data now abandoned, which is a continuation-in-part of application No. 11/941,764, filed on Nov. 16, 2007, now abandoned, said application No. 13/461,727 is a continuation-in-part of application No. PCT/US2010/058108, filed on Nov. 24, 2010, and a continuation-in-part of application No. 13/452,784, filed on Apr. 20, 2012, now Pat. No. 8,827,981, which is a continuation of application No. 12/029,428, filed on Feb. 11, 2008, now abandoned, which is a continuation of application No. 11/941,764, filed on Nov. 16, 2007, now abandoned.

(60) Provisional application No. 61/264,640, filed on Nov. 25, 2009, provisional application No. 61/296,013, filed on Jan. 18, 2010, provisional application No. 61/300,401, filed on Feb. 1, 2010.

(56) References Cited

U.S. PATENT DOCUMENTS

| | | |
|---|---|---|
| 3,625,200 A | 12/1971 | Muller |
| 3,908,637 A | 9/1975 | Doroshow |
| 4,033,331 A | 7/1977 | Guss et al. |
| 4,131,597 A | 12/1978 | Bluethgen et al. |
| 4,236,520 A | 12/1980 | Anderson |
| 4,276,880 A | 7/1981 | Malmin |
| 4,294,251 A | 10/1981 | Brems |
| 4,337,773 A | 7/1982 | Raftopoulos et al. |
| 4,386,717 A | 6/1983 | Koob |
| 4,399,814 A | 8/1983 | Pratt, Jr. et al. |
| 4,578,061 A | 3/1986 | Lemelson |
| 4,586,923 A | 5/1986 | Gould et al. |
| 4,619,263 A | 10/1986 | Frisbie et al. |
| 4,627,434 A | 12/1986 | Murray |
| 4,641,654 A | 2/1987 | Samson et al. |
| 4,653,489 A | 3/1987 | Tronzo |
| 4,668,295 A | 5/1987 | Bajpai |
| 4,722,948 A | 2/1988 | Sanderson |
| 4,731,054 A | 3/1988 | Billeter et al. |
| 4,747,840 A | 5/1988 | Ladika et al. |
| 4,748,969 A | 6/1988 | Wardle |
| 4,784,638 A | 11/1988 | Ghajar et al. |
| 4,842,603 A | 6/1989 | Draenert |
| 4,843,112 A | 6/1989 | Gerhart et al. |
| 4,846,814 A | 7/1989 | Ruiz |
| 4,865,586 A | 9/1989 | Hedberg |
| 4,869,906 A | 9/1989 | Dingeldein et al. |
| 4,888,366 A | 12/1989 | Chu |
| 4,900,303 A | 2/1990 | Lemelson |
| 4,961,731 A | 10/1990 | Bodicky et al. |
| 4,963,151 A | 10/1990 | Ducheyne et al. |
| 4,969,870 A | 11/1990 | Kramer et al. |
| 4,969,888 A | 11/1990 | Scholten et al. |
| 4,982,730 A | 1/1991 | Lewis, Jr. |
| 4,998,923 A | 3/1991 | Samson et al. |
| 5,004,501 A | 4/1991 | Faccioli |
| 5,017,627 A | 5/1991 | Bonfield |
| 5,046,513 A | 9/1991 | O'Leary et al. |
| 5,049,137 A | 9/1991 | Thompson |
| 5,049,157 A | 9/1991 | Mittelmeier et al. |
| 5,050,193 A | 9/1991 | Kuslich |
| 5,085,861 A | 2/1992 | Gerhart et al. |
| 5,088,991 A | 2/1992 | Weldon |
| 5,092,891 A | 3/1992 | Kummer et al. |
| 5,108,404 A | 4/1992 | Reiley |
| 5,112,303 A | 5/1992 | Pudenz et al. |
| 5,114,414 A | 5/1992 | Buchbinder |
| 5,116,305 A * | 5/1992 | Milder et al. ............ 600/18 |
| 5,147,334 A | 9/1992 | Moss |
| 5,156,606 A | 10/1992 | Chin |
| 5,163,431 A | 11/1992 | Griep |
| 5,184,757 A | 2/1993 | Giannuzzi |
| 5,188,619 A | 2/1993 | Myers |
| 5,196,201 A | 3/1993 | Larsson et al. |
| 5,197,971 A | 3/1993 | Bonutti |
| 5,211,631 A | 5/1993 | Sheaff |
| 5,231,989 A | 8/1993 | Middleman et al. |
| 5,242,082 A | 9/1993 | Giannuzzi |
| 5,264,214 A | 11/1993 | Rhee et al. |
| 5,266,248 A | 11/1993 | Ohtsuka et al. |
| 5,269,750 A | 12/1993 | Grulke et al. |
| 5,285,795 A | 2/1994 | Ryan et al. |
| 5,295,980 A | 3/1994 | Ersek |
| 5,296,026 A | 3/1994 | Monroe et al. |
| 5,308,342 A | 5/1994 | Sepetka et al. |
| 5,336,699 A | 8/1994 | Cooke et al. |
| 5,343,877 A | 9/1994 | Park |
| 5,352,715 A | 10/1994 | Wallace et al. |
| 5,356,629 A | 10/1994 | Sander |
| 5,360,416 A | 11/1994 | Ausherman et al. |
| 5,368,598 A | 11/1994 | Hasson |
| 5,372,587 A | 12/1994 | Hammerslag et al. |
| 5,378,234 A | 1/1995 | Hammerslag et al. |
| 5,380,307 A | 1/1995 | Chee et al. |
| 5,385,563 A | 1/1995 | Gross |
| 5,389,073 A | 2/1995 | Imran |
| 5,425,770 A | 6/1995 | Piez et al. |
| 5,431,168 A | 7/1995 | Webster, Jr. |
| 5,431,639 A | 7/1995 | Shaw |
| 5,480,382 A | 1/1996 | Hammerslag et al. |
| 5,484,424 A | 1/1996 | Cottenceau et al. |
| 5,489,275 A | 2/1996 | Thompson et al. |
| 5,496,330 A | 3/1996 | Bates et al. |
| 5,512,610 A | 4/1996 | Lin |
| 5,514,137 A | 5/1996 | Coutts |
| 5,531,715 A | 7/1996 | Engelson et al. |
| 5,533,985 A | 7/1996 | Wang |
| 5,535,922 A | 7/1996 | Maziarz |
| 5,549,542 A | 8/1996 | Kovalcheck |
| 5,549,679 A | 8/1996 | Kuslich |
| 5,554,114 A | 9/1996 | Wallace et al. |
| 5,571,085 A | 11/1996 | Accisano, III |
| 5,574,075 A | 11/1996 | Draenert |
| 5,616,121 A | 4/1997 | McKay |
| 5,624,396 A | 4/1997 | McNamara et al. |
| 5,637,091 A | 6/1997 | Hakky et al. |
| 5,681,289 A | 10/1997 | Wilcox et al. |
| 5,681,317 A | 10/1997 | Caldarise |
| 5,685,826 A | 11/1997 | Bonutti |
| 5,704,926 A | 1/1998 | Sutton |
| 5,709,697 A | 1/1998 | Ratcliff et al. |
| 5,725,568 A | 3/1998 | Hastings |
| 5,735,829 A | 4/1998 | Cherian |
| 5,741,320 A | 4/1998 | Thornton et al. |
| 5,800,408 A | 9/1998 | Strauss et al. |
| 5,810,867 A | 9/1998 | Zarbatany et al. |
| 5,820,592 A | 10/1998 | Hammerslag et al. |
| 5,833,692 A * | 11/1998 | Cesarini et al. ............ 606/79 |
| 5,847,046 A | 12/1998 | Jiang et al. |
| 5,858,003 A | 1/1999 | Atala |
| 5,860,952 A | 1/1999 | Quinn |
| 5,876,373 A | 3/1999 | Giba et al. |
| 5,902,839 A | 5/1999 | Lautenschlager |
| 5,914,356 A | 6/1999 | Erbe |
| 5,928,239 A | 7/1999 | Mirza |
| 5,931,829 A | 8/1999 | Burbank et al. |
| 5,972,015 A | 10/1999 | Scribner et al. |
| 5,997,581 A | 12/1999 | Khalili |
| 6,019,765 A | 2/2000 | Thornhill et al. |
| 6,027,487 A | 2/2000 | Crocker |
| 6,030,360 A | 2/2000 | Biggs |
| 6,048,346 A | 4/2000 | Reiley et al. |
| 6,059,739 A | 5/2000 | Baumann |
| 6,066,154 A | 5/2000 | Reiley et al. |
| 6,066,176 A | 5/2000 | Oshida |
| 6,080,801 A | 6/2000 | Draenert |
| 6,099,514 A | 8/2000 | Sharkey et al. |
| 6,110,155 A | 8/2000 | Baudino |
| 6,127,597 A | 10/2000 | Beyar et al. |
| 6,146,355 A | 11/2000 | Biggs |
| 6,183,435 B1 | 2/2001 | Bumbalough et al. |
| 6,203,507 B1 | 3/2001 | Wadsworth et al. |

(56) References Cited

U.S. PATENT DOCUMENTS

| | | |
|---|---|---|
| 6,203,574 B1 | 3/2001 | Kawamura |
| 6,228,052 B1 | 5/2001 | Pohndorf |
| 6,228,904 B1 | 5/2001 | Yadav |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,251,092 B1 | 6/2001 | Qin et al. |
| 6,276,700 B1 | 8/2001 | Way et al. |
| 6,280,413 B1 | 8/2001 | Clark et al. |
| 6,280,434 B1 | 8/2001 | Kinoshita et al. |
| 6,280,456 B1 | 8/2001 | Scribner et al. |
| 6,280,473 B1 | 8/2001 | Lemperle et al. |
| 6,291,547 B1 | 9/2001 | Lyles |
| 6,332,894 B1 | 12/2001 | Stalcup |
| 6,348,055 B1 | 2/2002 | Preissman |
| 6,358,251 B1 | 3/2002 | Mirza |
| 6,375,659 B1 | 4/2002 | Erbe et al. |
| 6,383,188 B2 | 5/2002 | Kuslich et al. |
| 6,383,190 B1 | 5/2002 | Preissman |
| 6,395,007 B1 | 5/2002 | Bhatnagar et al. |
| 6,437,019 B1 | 8/2002 | Rusin |
| 6,440,138 B1 | 8/2002 | Reiley et al. |
| 6,447,514 B1 | 9/2002 | Stalcup et al. |
| 6,479,565 B1 | 11/2002 | Stanley |
| 6,484,904 B1 | 11/2002 | Horner et al. |
| 6,506,217 B1 | 1/2003 | Arnett |
| 6,511,471 B2 | 1/2003 | Rosenman et al. |
| 6,524,296 B1 | 2/2003 | Beals |
| 6,565,588 B1 | 5/2003 | Clement et al. |
| 6,575,978 B2 | 6/2003 | Peterson et al. |
| 6,576,249 B1 | 6/2003 | Gendler et al. |
| 6,582,446 B1 | 6/2003 | Marchosky |
| 6,592,559 B1 | 7/2003 | Pakter et al. |
| 6,599,961 B1 | 7/2003 | Pienkowski et al. |
| 6,607,544 B1 * | 8/2003 | Boucher et al. ............... 606/192 |
| 6,613,054 B2 | 9/2003 | Scribner et al. |
| 6,620,162 B2 | 9/2003 | Kuslich et al. |
| 6,623,448 B2 | 9/2003 | Slater |
| 6,638,268 B2 | 10/2003 | Niazi |
| 6,641,587 B2 | 11/2003 | Scribner et al. |
| 6,645,213 B2 | 11/2003 | Sand et al. |
| 6,663,647 B2 | 12/2003 | Reiley et al. |
| 6,676,665 B2 | 1/2004 | Foley et al. |
| 6,679,886 B2 | 1/2004 | Weikel et al. |
| 6,689,823 B1 | 2/2004 | Bellare et al. |
| 6,692,532 B1 | 2/2004 | Healy et al. |
| 6,716,216 B1 | 4/2004 | Boucher et al. |
| 6,719,761 B1 | 4/2004 | Reiley et al. |
| 6,719,773 B1 | 4/2004 | Boucher et al. |
| 6,726,691 B2 | 4/2004 | Osorio et al. |
| 6,730,095 B2 | 5/2004 | Olson, Jr. et al. |
| 6,740,093 B2 | 5/2004 | Hochschuler et al. |
| 6,743,239 B1 | 6/2004 | Kuehn et al. |
| 6,746,451 B2 | 6/2004 | Middleton et al. |
| 6,752,863 B2 | 6/2004 | Lyles et al. |
| 6,753,007 B2 | 6/2004 | Haggard et al. |
| 6,770,079 B2 | 8/2004 | Bhatnagar et al. |
| 6,814,734 B2 | 11/2004 | Chappuis et al. |
| 6,814,736 B2 | 11/2004 | Reiley et al. |
| 6,818,001 B2 | 11/2004 | Wulfman et al. |
| 6,832,984 B2 | 12/2004 | Stelzer et al. |
| 6,835,193 B2 | 12/2004 | Epstein et al. |
| 6,837,867 B2 | 1/2005 | Kortelling |
| 6,863,672 B2 | 3/2005 | Reiley et al. |
| 6,869,445 B1 | 3/2005 | Johnson |
| 6,875,219 B2 | 4/2005 | Arramon |
| 6,887,246 B2 | 5/2005 | Bhatnagar et al. |
| 6,899,715 B1 | 5/2005 | Beaty |
| 6,899,719 B2 | 5/2005 | Reiley et al. |
| 6,913,594 B2 | 7/2005 | Coleman et al. |
| 6,916,306 B1 | 7/2005 | Jenkins et al. |
| 6,923,813 B2 | 8/2005 | Phillips et al. |
| 6,945,956 B2 | 9/2005 | Waldhauser et al. |
| 6,953,594 B2 | 10/2005 | Lee et al. |
| 6,955,716 B2 | 10/2005 | Xu et al. |
| 6,976,987 B2 | 12/2005 | Flores |
| 6,979,312 B2 | 12/2005 | Shimada |
| 6,979,352 B2 | 12/2005 | Reynolds |
| 6,981,981 B2 | 1/2006 | Reiley et al. |
| 6,991,616 B2 | 1/2006 | Bencini et al. |
| 6,998,128 B2 | 2/2006 | Haggard et al. |
| 7,004,945 B2 | 2/2006 | Boyd et al. |
| 7,008,433 B2 | 3/2006 | Voellmicke et al. |
| 7,018,460 B2 | 3/2006 | Xu et al. |
| 7,029,468 B2 | 4/2006 | Honebrink |
| 7,044,954 B2 | 5/2006 | Reiley et al. |
| 7,059,330 B1 | 6/2006 | Makower et al. |
| 7,063,682 B1 | 6/2006 | Whayne et al. |
| 7,066,942 B2 | 6/2006 | Treace |
| RE39,196 E | 7/2006 | Ying et al. |
| 7,081,122 B1 | 7/2006 | Reiley et al. |
| 7,081,161 B2 | 7/2006 | Genge et al. |
| 7,091,258 B2 | 8/2006 | Neubert et al. |
| 7,091,260 B2 | 8/2006 | Kuhn |
| 7,094,202 B2 | 8/2006 | Nobis et al. |
| 7,094,286 B2 | 8/2006 | Liu |
| 7,109,254 B2 | 9/2006 | Muller et al. |
| 7,112,205 B2 | 9/2006 | Carrison |
| 7,114,501 B2 | 10/2006 | Johnson et al. |
| 7,138,442 B2 | 11/2006 | Smith |
| 7,153,306 B2 | 12/2006 | Ralph et al. |
| 7,153,307 B2 | 12/2006 | Scribner et al. |
| 7,166,121 B2 | 1/2007 | Reiley et al. |
| 7,172,629 B2 | 2/2007 | McKay |
| 7,186,761 B2 | 3/2007 | Soffiati |
| 7,226,481 B2 | 6/2007 | Kuslich |
| 7,252,671 B2 | 8/2007 | Scribner et al. |
| 7,465,318 B2 | 12/2008 | Sennett |
| 7,544,196 B2 | 6/2009 | Bagga et al. |
| 7,559,932 B2 | 7/2009 | Truckai et al. |
| 7,572,263 B2 | 8/2009 | Preissman |
| 7,591,822 B2 | 9/2009 | Olson, Jr. et al. |
| 7,641,664 B2 | 1/2010 | Pagano |
| 7,731,720 B2 | 6/2010 | Sand et al. |
| 7,811,291 B2 | 10/2010 | Liu et al. |
| 7,842,041 B2 | 11/2010 | Liu et al. |
| 7,887,543 B2 | 2/2011 | Sand et al. |
| 7,918,874 B2 | 4/2011 | Siegal |
| 7,972,340 B2 | 7/2011 | Sand et al. |
| 8,034,071 B2 | 10/2011 | Scribner et al. |
| 8,827,981 B2 | 9/2014 | Liu et al. |
| 2001/0011174 A1 | 8/2001 | Reiley et al. |
| 2001/0023349 A1 | 9/2001 | VanTassel et al. |
| 2002/0013600 A1 | 1/2002 | Scribner et al. |
| 2002/0026195 A1 | 2/2002 | Layne et al. |
| 2002/0068974 A1 | 6/2002 | Kuslich et al. |
| 2002/0077595 A1 | 6/2002 | Hundertmark et al. |
| 2002/0082605 A1 | 6/2002 | Reiley et al. |
| 2002/0115742 A1 | 8/2002 | Trieu et al. |
| 2002/0156483 A1 | 10/2002 | Voellmicke et al. |
| 2002/0188299 A1 | 12/2002 | Reiley et al. |
| 2002/0188300 A1 | 12/2002 | Arramon et al. |
| 2003/0032929 A1 | 2/2003 | McGuckin |
| 2003/0032963 A1 | 2/2003 | Reiss et al. |
| 2003/0036763 A1 | 2/2003 | Bhatnagar et al. |
| 2003/0050644 A1 | 3/2003 | Boucher et al. |
| 2003/0073979 A1 | 4/2003 | Naimark et al. |
| 2003/0130664 A1 | 7/2003 | Boucher et al. |
| 2003/0163085 A1 | 8/2003 | Tanner et al. |
| 2003/0191489 A1 | 10/2003 | Reiley et al. |
| 2003/0195547 A1 | 10/2003 | Scribner et al. |
| 2003/0220414 A1 | 11/2003 | Axen et al. |
| 2003/0225432 A1 | 12/2003 | Baptiste et al. |
| 2003/0233096 A1 | 12/2003 | Osorio et al. |
| 2004/0023784 A1 | 2/2004 | Yu et al. |
| 2004/0024081 A1 | 2/2004 | Trieu et al. |
| 2004/0024409 A1 | 2/2004 | Sand et al. |
| 2004/0024410 A1 | 2/2004 | Olson et al. |
| 2004/0034384 A1 | 2/2004 | Fukaya |
| 2004/0044096 A1 | 3/2004 | Smith et al. |
| 2004/0044350 A1 | 3/2004 | Martin et al. |
| 2004/0087994 A1 | 5/2004 | Suddaby |
| 2004/0092946 A1 | 5/2004 | Bagga et al. |
| 2004/0097612 A1 | 5/2004 | Rosenberg et al. |

(56) References Cited

U.S. PATENT DOCUMENTS

| | | |
|---|---|---|
| 2004/0127987 A1 | 7/2004 | Evans et al. |
| 2004/0133208 A1 | 7/2004 | Weikel et al. |
| 2004/0138758 A1 | 7/2004 | Evans et al. |
| 2004/0153004 A1 | 8/2004 | Burbank et al. |
| 2004/0153115 A1 | 8/2004 | Reiley et al. |
| 2004/0167561 A1 | 8/2004 | Boucher et al. |
| 2004/0167562 A1 | 8/2004 | Osorio et al. |
| 2004/0167625 A1 | 8/2004 | Beyar et al. |
| 2004/0210231 A1 | 10/2004 | Boucher et al. |
| 2004/0215343 A1 | 10/2004 | Hochschuler et al. |
| 2004/0220680 A1 | 11/2004 | Yamamoto et al. |
| 2004/0225296 A1 | 11/2004 | Reiss et al. |
| 2004/0226479 A1 | 11/2004 | Lyles et al. |
| 2004/0230309 A1 | 11/2004 | DiMauro et al. |
| 2004/0236186 A1 | 11/2004 | Chu |
| 2004/0247644 A1 | 12/2004 | Bratt et al. |
| 2004/0267271 A9 | 12/2004 | Scribner et al. |
| 2005/0027245 A1 | 2/2005 | Sachdeva et al. |
| 2005/0033303 A1 | 2/2005 | Chappuis et al. |
| 2005/0038383 A1 | 2/2005 | Kelley et al. |
| 2005/0043737 A1 | 2/2005 | Reiley et al. |
| 2005/0060030 A1 | 3/2005 | Lashinski et al. |
| 2005/0070844 A1 | 3/2005 | Chow et al. |
| 2005/0070915 A1 | 3/2005 | Mazzuca et al. |
| 2005/0970912 | 3/2005 | Voellmicke |
| 2005/0090852 A1 | 4/2005 | Layne et al. |
| 2005/0113836 A1 | 5/2005 | Lozier et al. |
| 2005/0124989 A1 | 6/2005 | Suddaby |
| 2005/0143827 A1 | 6/2005 | Globerman et al. |
| 2005/0182412 A1 | 8/2005 | Johnson et al. |
| 2005/0182413 A1 | 8/2005 | Johnson et al. |
| 2005/0187556 A1 | 8/2005 | Stack et al. |
| 2005/0199156 A1 | 9/2005 | Khairoun et al. |
| 2005/0209557 A1 | 9/2005 | Carroll et al. |
| 2005/0216018 A1 | 9/2005 | Sennett |
| 2005/0228391 A1 | 10/2005 | Levy et al. |
| 2005/0234425 A1 | 10/2005 | Miller et al. |
| 2005/0240193 A1 | 10/2005 | Layne et al. |
| 2005/0251266 A1 | 11/2005 | Maspero et al. |
| 2005/0251267 A1 | 11/2005 | Winterbottom et al. |
| 2005/0261683 A1 | 11/2005 | Veldhuizen et al. |
| 2006/0024348 A1 | 2/2006 | Engqvist et al. |
| 2006/0041033 A1 | 2/2006 | Bisig et al. |
| 2006/0052743 A1 | 3/2006 | Reynolds |
| 2006/0064101 A1 | 3/2006 | Arramon |
| 2006/0074433 A1 | 4/2006 | McGill et al. |
| 2006/0100635 A1 | 5/2006 | Reiley et al. |
| 2006/0100706 A1 | 5/2006 | Shadduck et al. |
| 2006/0106392 A1 | 5/2006 | Embry |
| 2006/0106459 A1 | 5/2006 | Truckai |
| 2006/0116689 A1 | 6/2006 | Albans et al. |
| 2006/0116690 A1 | 6/2006 | Pagano |
| 2006/0142732 A1 | 6/2006 | Karmarkar et al. |
| 2006/0149268 A1 | 7/2006 | Truckai et al. |
| 2006/0149281 A1 | 7/2006 | Reiley et al. |
| 2006/0156959 A1 | 7/2006 | Engqvist |
| 2006/0184106 A1 | 8/2006 | McDaniel et al. |
| 2006/0184192 A1 | 8/2006 | Markworth et al. |
| 2006/0206116 A1 | 9/2006 | Yeung |
| 2006/0206136 A1 | 9/2006 | Sachdeva et al. |
| 2006/0217736 A1 | 9/2006 | Kaneko |
| 2006/0229625 A1 | 10/2006 | Truckai et al. |
| 2006/0229631 A1 | 10/2006 | Reiley et al. |
| 2006/0235417 A1 | 10/2006 | Sala |
| 2006/0264945 A1 | 11/2006 | Edidin et al. |
| 2006/0266372 A1 | 11/2006 | Miller et al. |
| 2006/0270750 A1 | 11/2006 | Almen |
| 2006/0271061 A1 | 11/2006 | Beyar et al. |
| 2006/0276797 A1 | 12/2006 | Botimer |
| 2006/0276819 A1 | 12/2006 | Osorio et al. |
| 2006/0293687 A1 | 12/2006 | Bogert |
| 2007/0010845 A1 | 1/2007 | Gong et al. |
| 2007/0016130 A1 | 1/2007 | Leeflang et al. |
| 2007/0016211 A1 | 1/2007 | Botimer |
| 2007/0021769 A1 | 1/2007 | Scribner et al. |
| 2007/0043373 A1 | 2/2007 | Sala et al. |
| 2007/0055201 A1 | 3/2007 | Seto et al. |
| 2007/0055266 A1 | 3/2007 | Osorio et al. |
| 2007/0055275 A1 | 3/2007 | Schaller |
| 2007/0055277 A1 | 3/2007 | Osorio et al. |
| 2007/0055278 A1 | 3/2007 | Osorio et al. |
| 2007/0055279 A1 | 3/2007 | Sand et al. |
| 2007/0055283 A1 | 3/2007 | Scribner |
| 2007/0055284 A1 | 3/2007 | Osorio |
| 2007/0055285 A1 | 3/2007 | Osorio et al. |
| 2007/0055300 A1 | 3/2007 | Osorio et al. |
| 2007/0055382 A1 | 3/2007 | Osorio et al. |
| 2007/0059281 A1 | 3/2007 | Moseley et al. |
| 2007/0067034 A1 | 3/2007 | Chirico et al. |
| 2007/0114248 A1 | 5/2007 | Kovac |
| 2007/0118142 A1 | 5/2007 | Krueger |
| 2007/0118143 A1 | 5/2007 | Ralph et al. |
| 2007/0142842 A1 | 6/2007 | Krueger et al. |
| 2007/0162042 A1 | 7/2007 | Dunker |
| 2007/0173939 A1 | 7/2007 | Kim et al. |
| 2007/0185231 A1 | 8/2007 | Liu et al. |
| 2007/0197935 A1 | 8/2007 | Reiley |
| 2007/0198023 A1 | 8/2007 | Sand et al. |
| 2007/0211563 A1 | 9/2007 | De Vries |
| 2007/0233146 A1 | 10/2007 | Henniges et al. |
| 2007/0260223 A1 | 11/2007 | Scheibe et al. |
| 2007/0270876 A1 | 11/2007 | Kuo et al. |
| 2008/0058725 A1 | 3/2008 | Scribner et al. |
| 2008/0058827 A1 | 3/2008 | Osorio et al. |
| 2008/0058840 A1 | 3/2008 | Albrecht |
| 2008/0065020 A1 | 3/2008 | Ralph et al. |
| 2008/0065087 A1 | 3/2008 | Osorio et al. |
| 2008/0065190 A1 | 3/2008 | Osorio et al. |
| 2008/0086142 A1 | 4/2008 | Kohm et al. |
| 2008/0140079 A1 | 6/2008 | Osorio et al. |
| 2008/0195112 A1 | 8/2008 | Liu et al. |
| 2008/0221608 A1* | 9/2008 | Betts .................. 606/191 |
| 2008/0228192 A1 | 9/2008 | Beyar et al. |
| 2008/0249481 A1 | 10/2008 | Crainich et al. |
| 2008/0269766 A1 | 10/2008 | Justis |
| 2008/0269796 A1 | 10/2008 | Reiley et al. |
| 2008/0294167 A1 | 11/2008 | Schumacher et al. |
| 2009/0076517 A1 | 3/2009 | Reiley et al. |
| 2009/0105775 A1 | 4/2009 | Mitchell |
| 2009/0131867 A1 | 5/2009 | Liu et al. |
| 2009/0131886 A1 | 5/2009 | Liu et al. |
| 2009/0131945 A1 | 5/2009 | Liu et al. |
| 2009/0131948 A1 | 5/2009 | Liu et al. |
| 2009/0131950 A1 | 5/2009 | Liu et al. |
| 2009/0182427 A1 | 7/2009 | Liu et al. |
| 2009/0292289 A9 | 11/2009 | Sand et al. |
| 2009/0299282 A1 | 12/2009 | Lau et al. |
| 2010/0211076 A1* | 8/2010 | Germain et al. .............. 606/84 |
| 2010/0298832 A1 | 11/2010 | Lau et al. |
| 2012/0130381 A1 | 5/2012 | Germain |
| 2012/0158004 A1 | 6/2012 | Burger et al. |
| 2012/0191095 A1 | 7/2012 | Burger et al. |
| 2012/0265186 A1 | 10/2012 | Burger et al. |
| 2013/0345709 A1 | 12/2013 | Burger et al. |
| 2014/0316413 A1 | 10/2014 | Burger et al. |

FOREIGN PATENT DOCUMENTS

| | | |
|---|---|---|
| WO | 0203870 | 1/2002 |
| WO | 2007087400 | 8/2007 |
| WO | 2010135602 | 11/2010 |
| WO | 2011066465 | 6/2011 |

OTHER PUBLICATIONS

International Search Report for PCT/US08/83698 dated Jan. 22, 2009.

Disc-O-Tech Confidence Cement System at http://www.disco-o-tech.com/Articles/Article.asp?CategoryID=4&ArticleID=168 accessed Dec. 3, 2007.

Dai et al, "Bone-Particle-Impregnated Bone Cement: An in vivo weight-bearing study," Journal of Biomedical Materials Research, vol. 25, 141-156 (1991).

(56) References Cited

OTHER PUBLICATIONS

Hasenwinkel et al, "A Novel High-Viscosity, Two-Solution Acrylic Bone Cement: Effect of Chemical Composition on Propeties," J. Biomed Mater. Res. vol. 47, No. 1, 36-45 (1999).

Klawitter, J.J. and Hulbert, S.F., "Application of Porous Ceramics for the Attachment of Load Bearing Internal Orthopedic Applications," J. Biomed. Mater. Res. Symp., 2(1), 161-229 (1972).

Liu et al., "Bone-Particle-Impregnate Bone Cement: An In Vitro Study," Journal of Biomedical Materials Research, vol. 21, 247-261 (1987).

Park et al., "The Material Properties of Bone-Particle Impregnated PMMA," Journal of Biomechanical Engineering, vol. 108, 141-148 (1986).

Park, J.B. and Lakes, S., "Biornaterials: An Introduction—Second Edition," Plenum Press, pp. 177-178 (1992).

International Search Report and Written Opinion for corresponding European Patent Application No. 13784241.5 dated Nov. 20, 2015.

\* cited by examiner

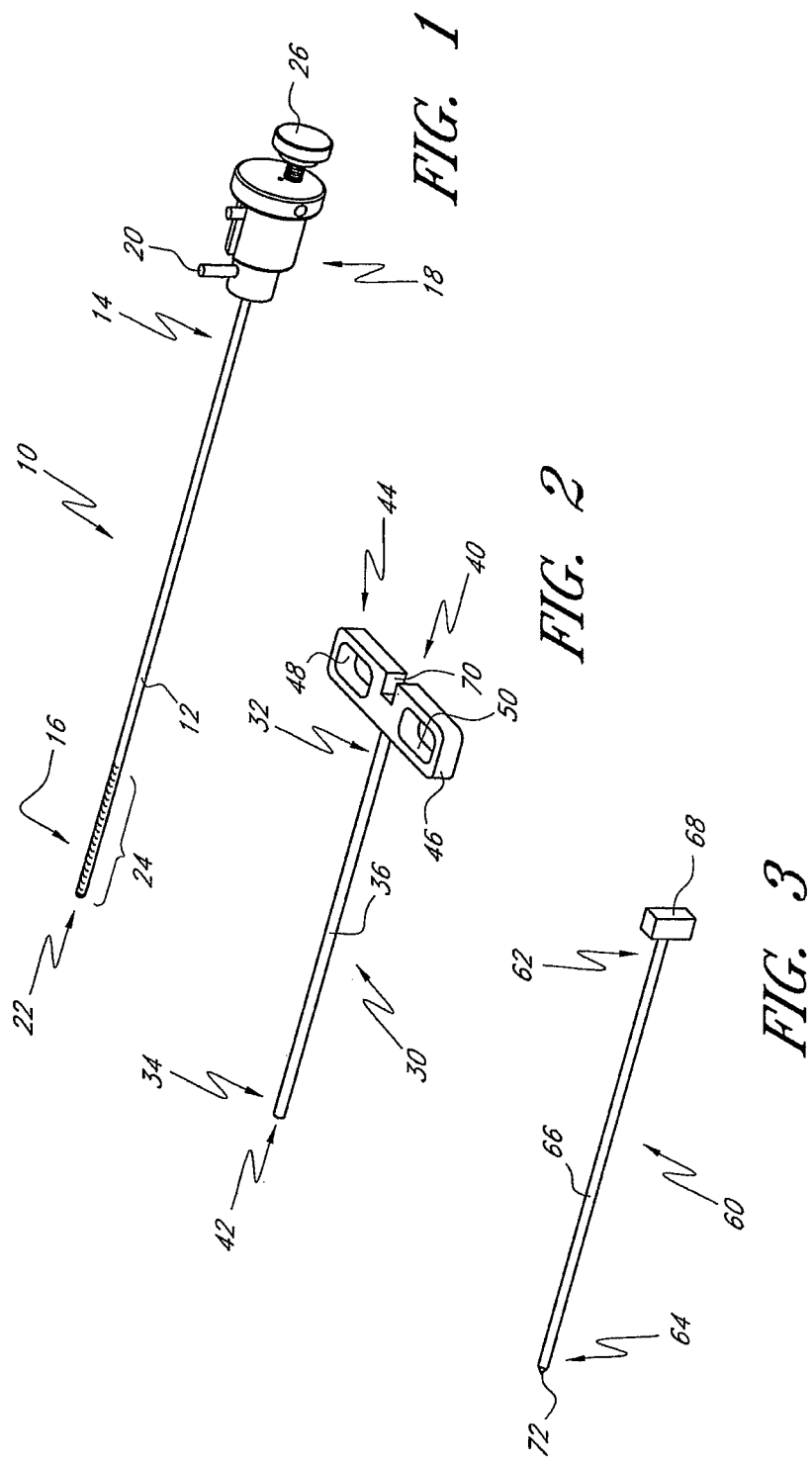

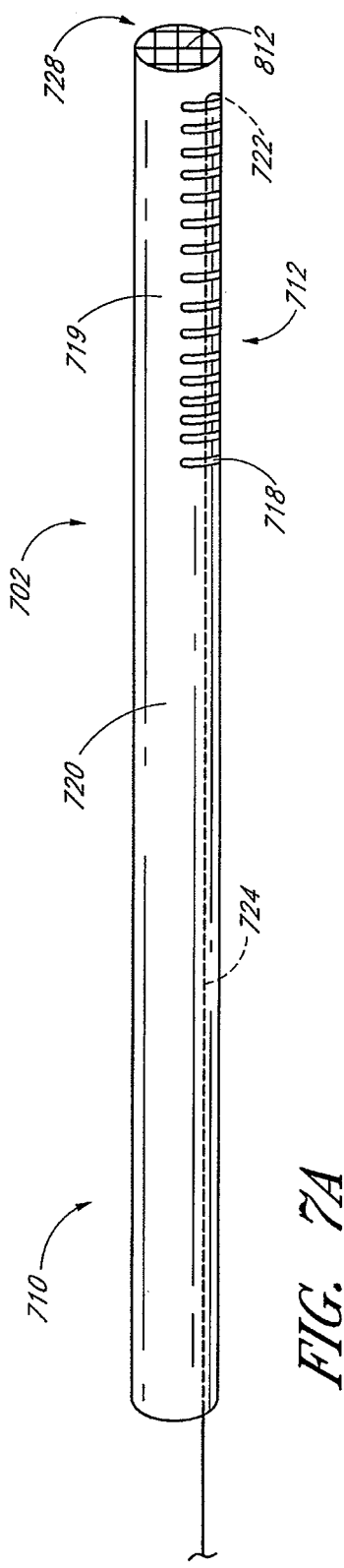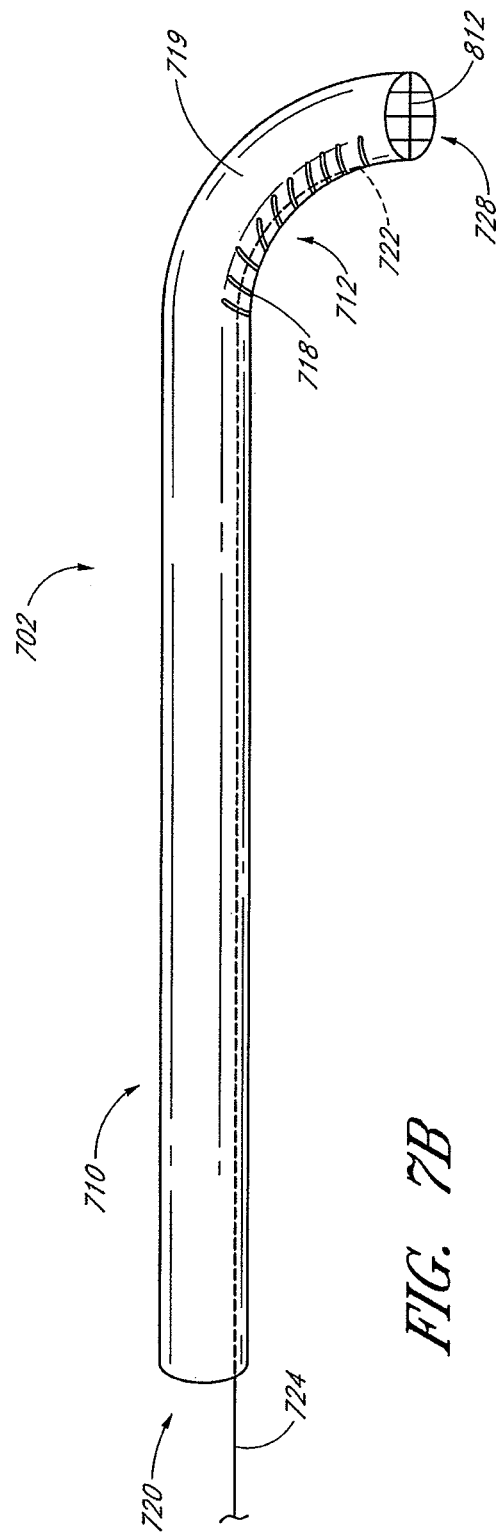
FIG. 7A
FIG. 7B

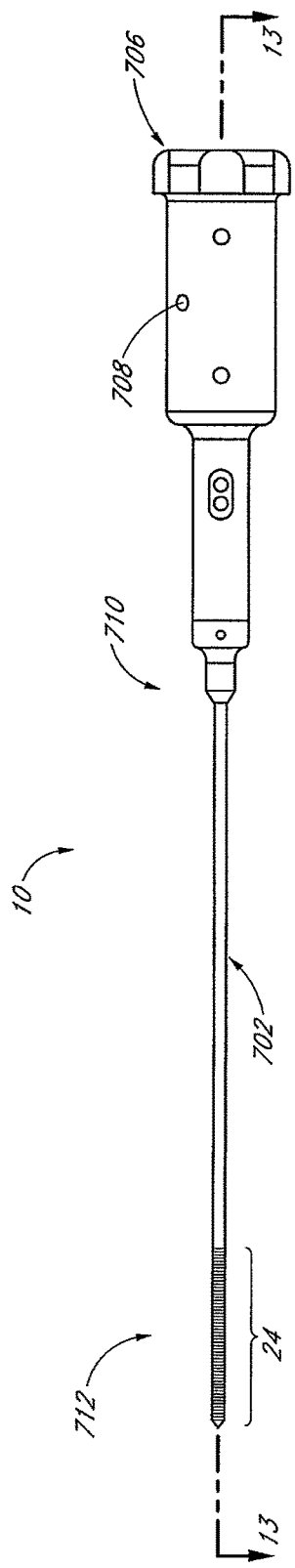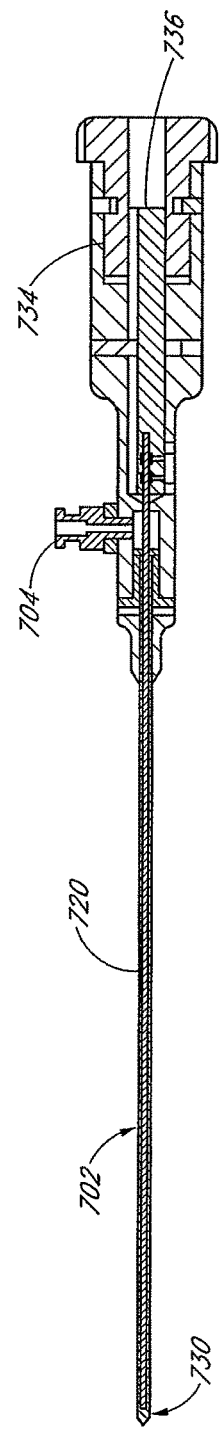
FIG. 12
FIG. 13

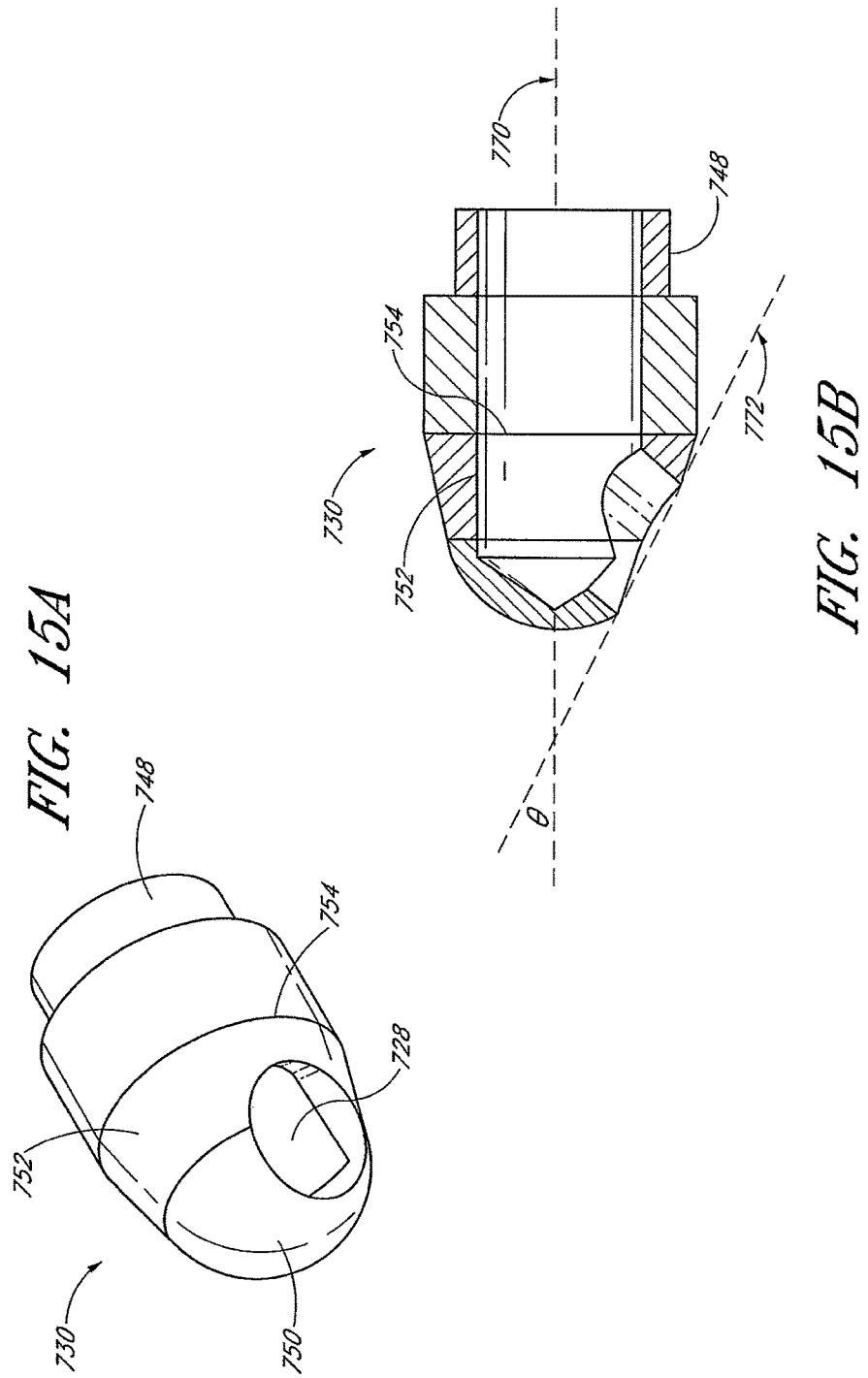

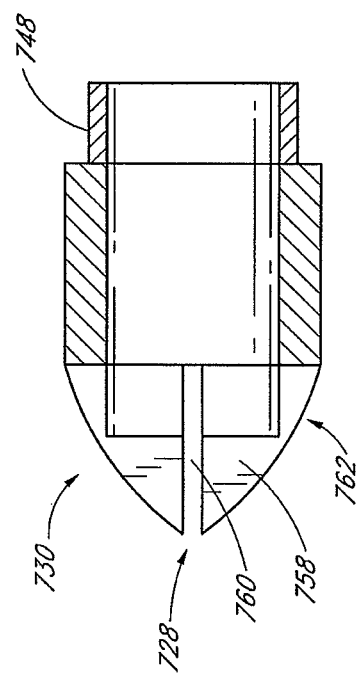
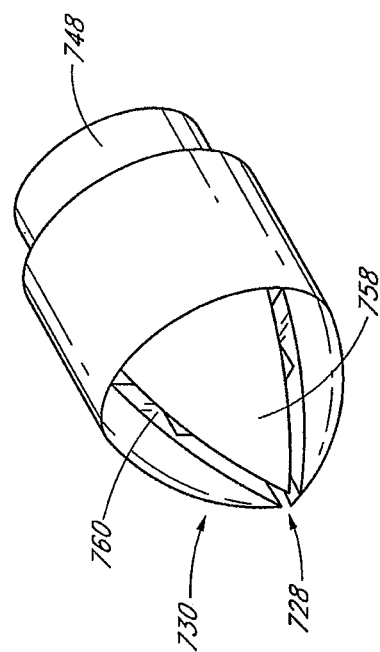
FIG. 15H
FIG. 15G

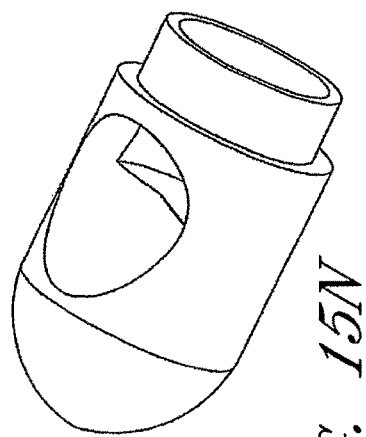
*FIG. 15N*
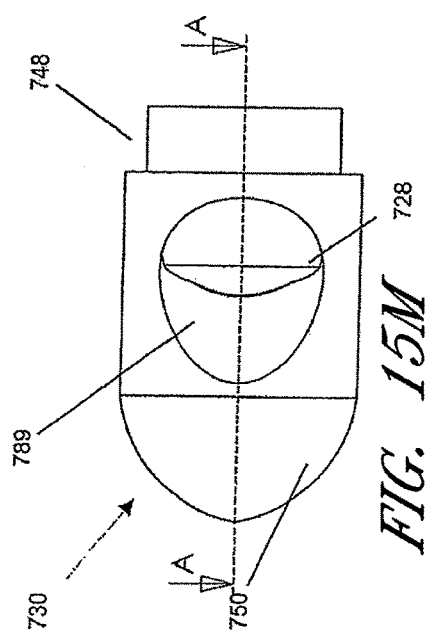
*FIG. 15M*
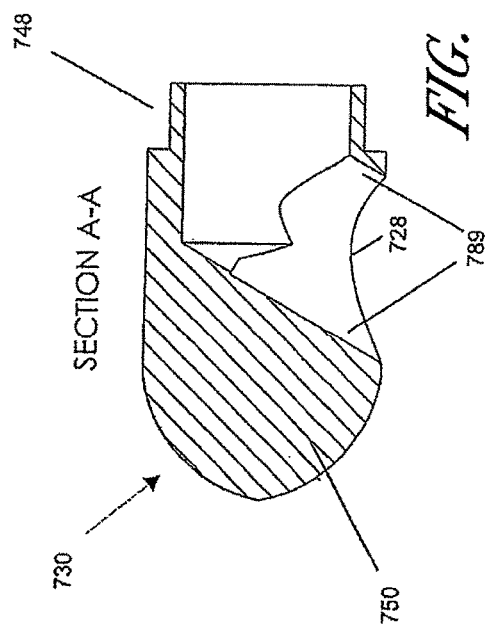
*FIG. 15M1*

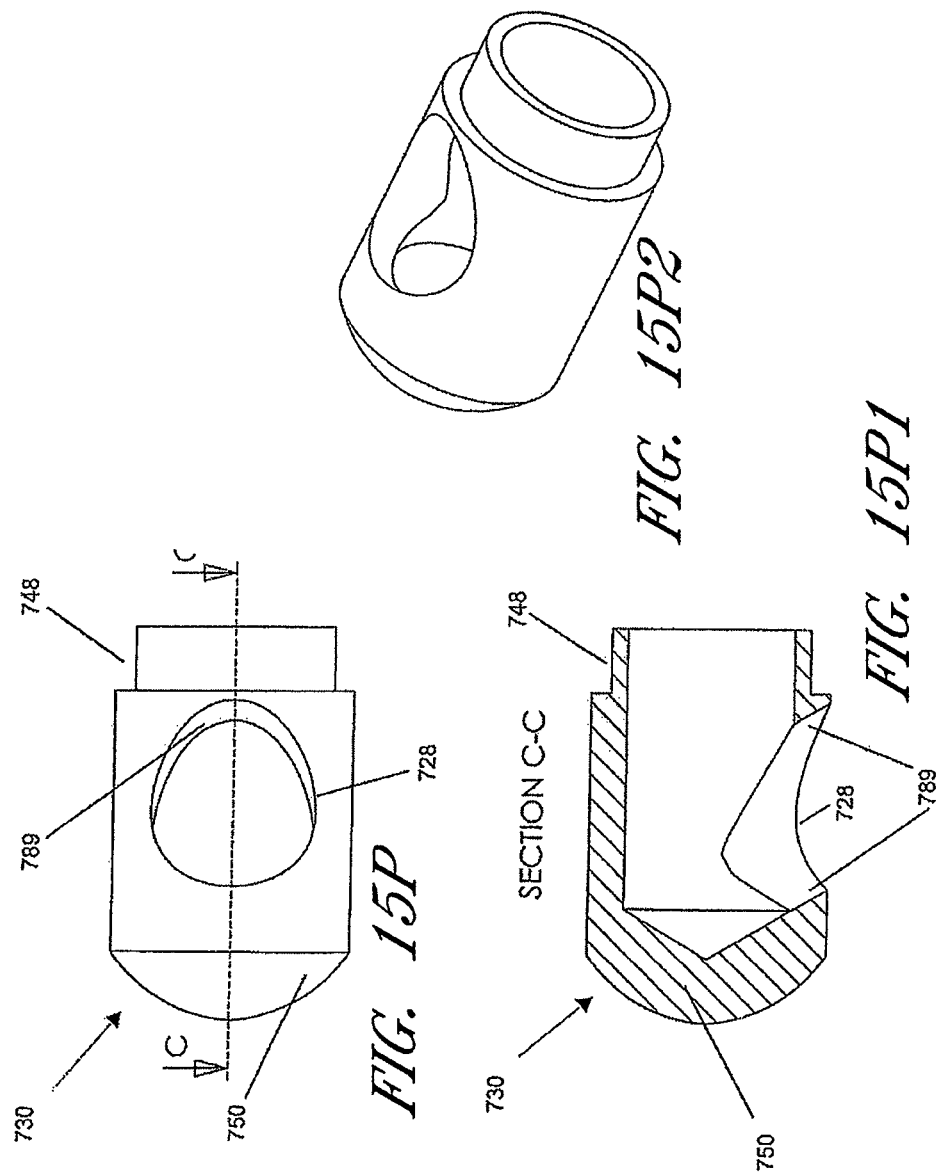

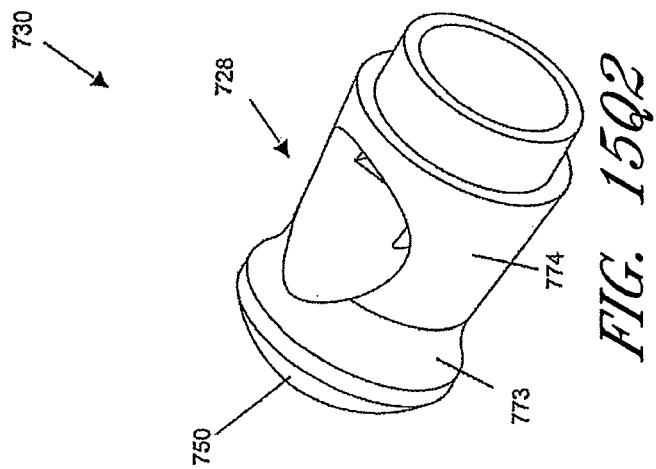
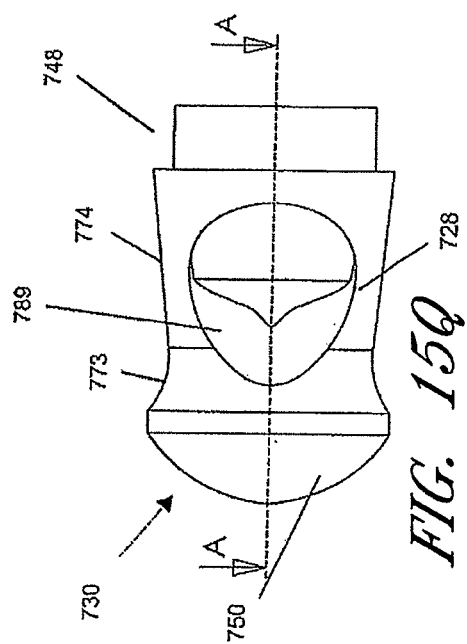
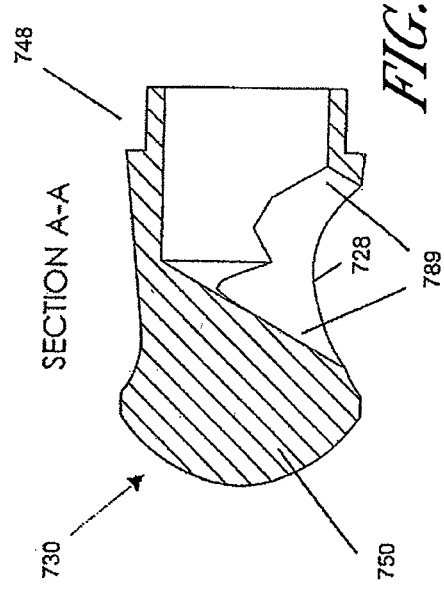

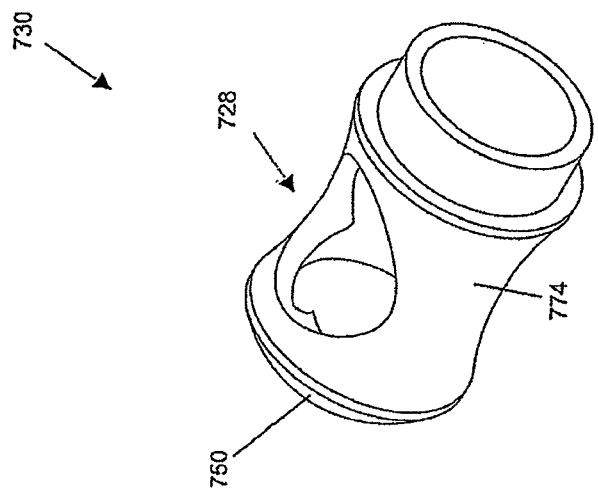
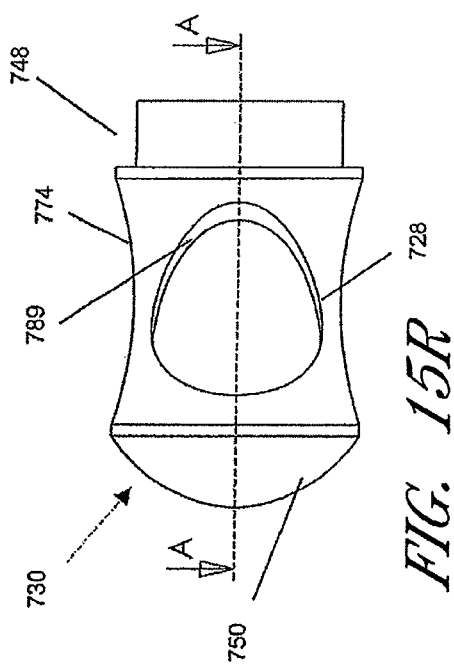
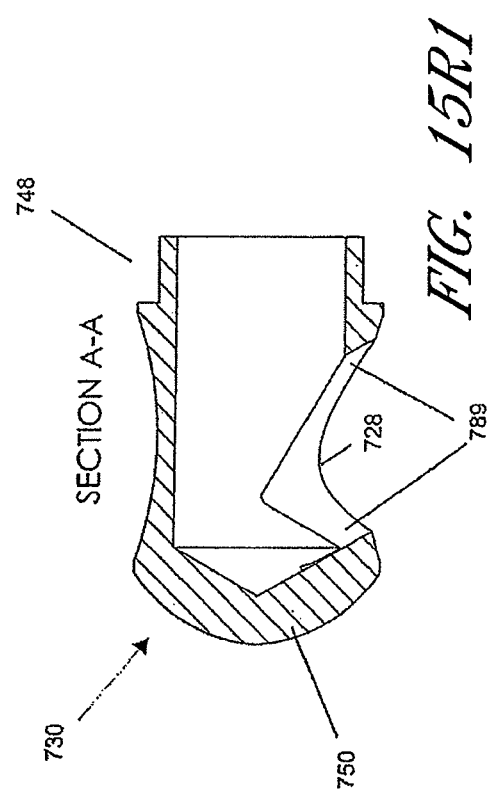
FIG. 15R2
FIG. 15R
FIG. 15R1

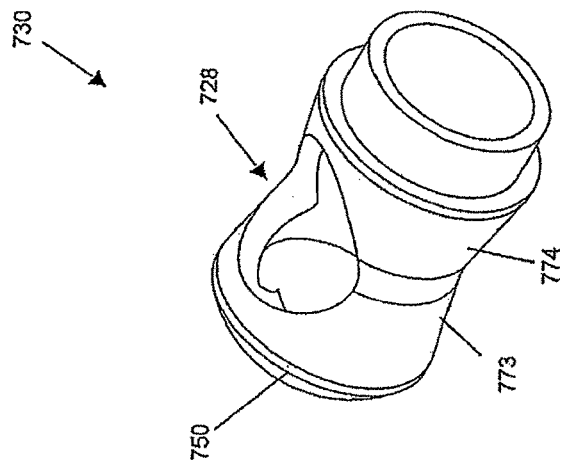
FIG. 15S2
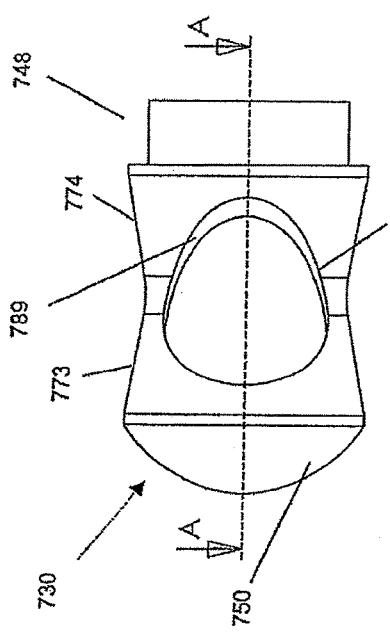
FIG. 15S
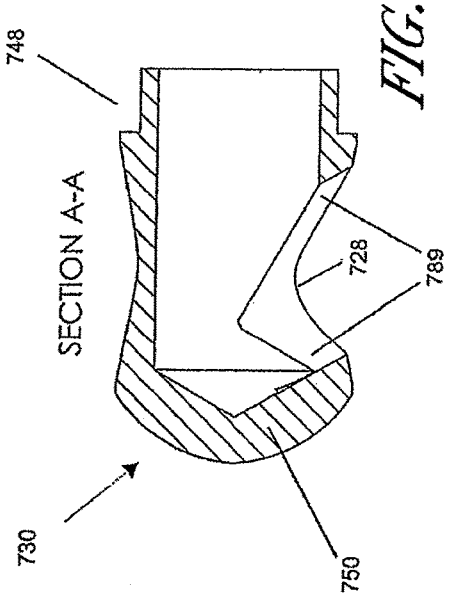
FIG. 15S1

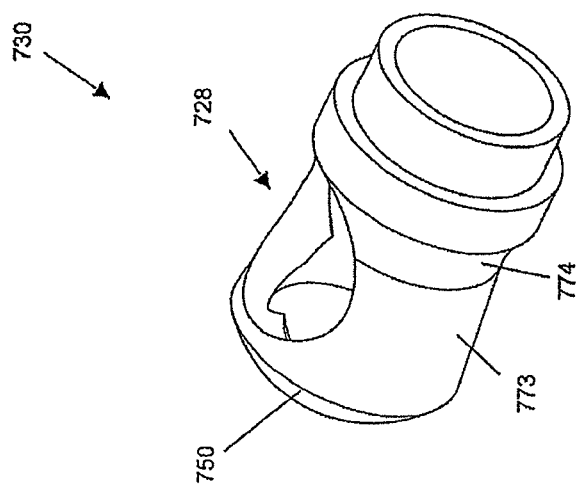
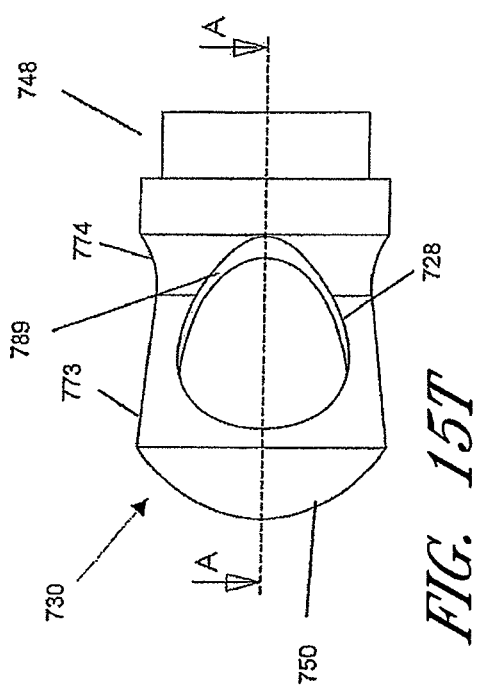
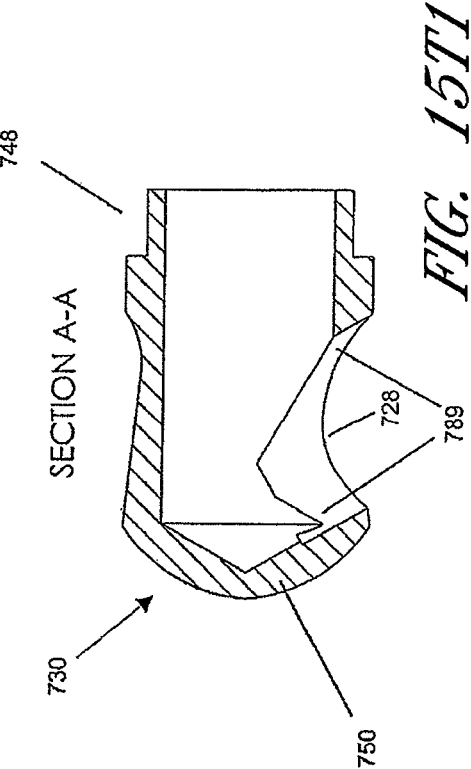
FIG. 15T2
FIG. 15T
FIG. 15T1

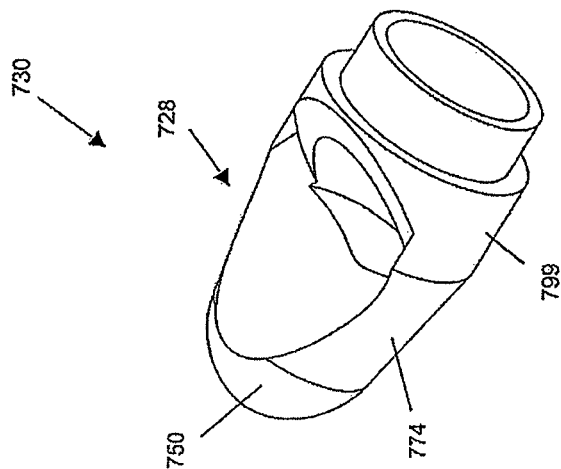
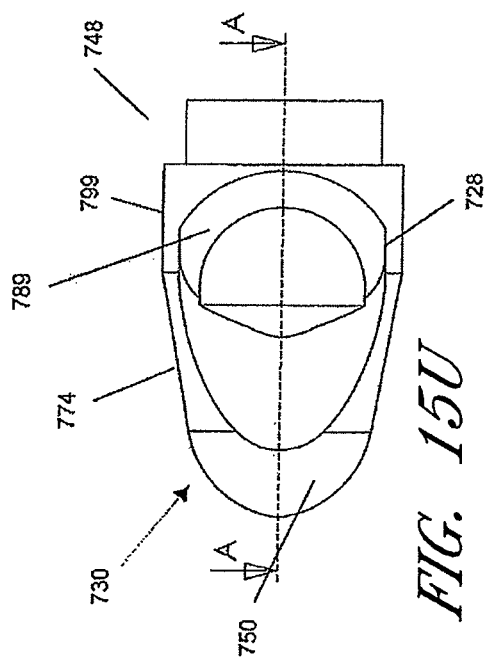
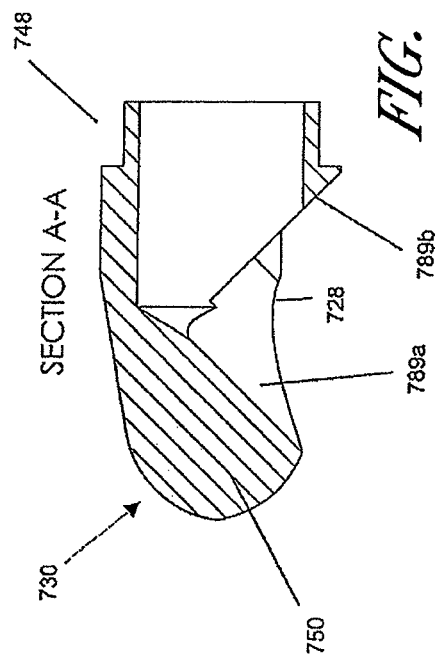
FIG. 15U2
FIG. 15U
FIG. 15U1

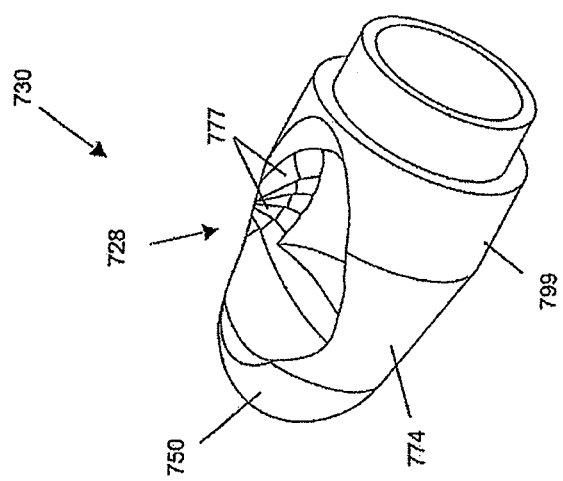
FIG. 15V2
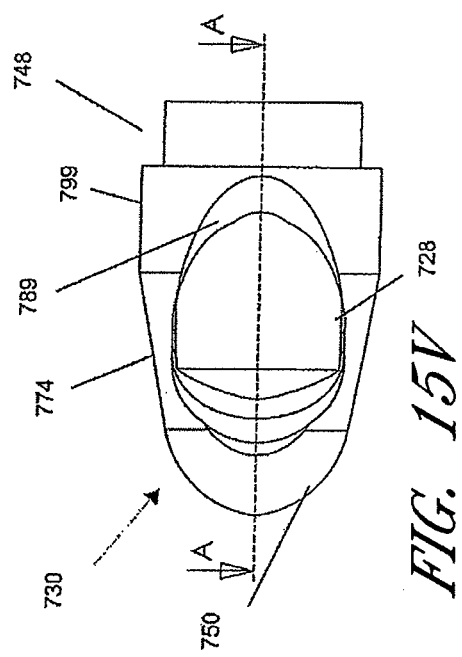
FIG. 15V
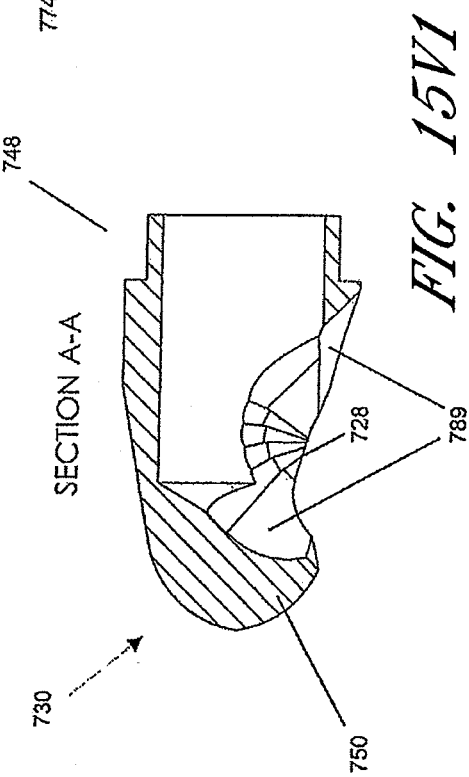
FIG. 15V1

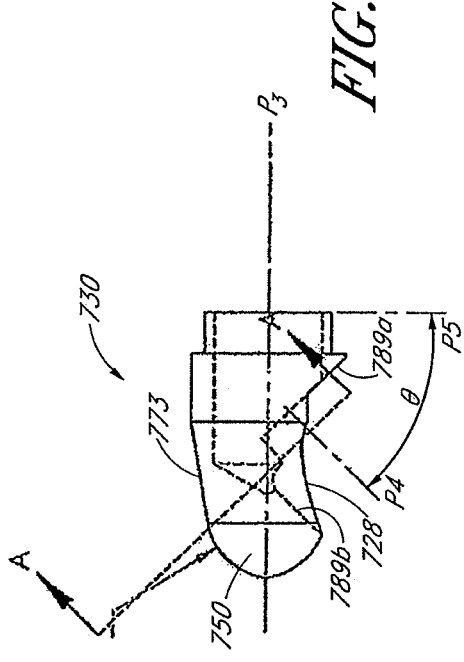
FIG. 15W2
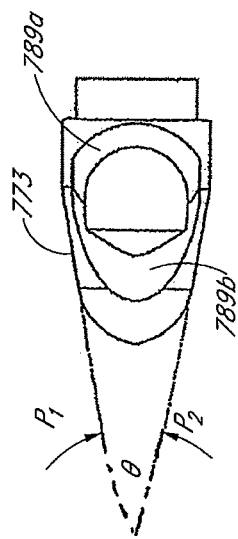
FIG. 15W
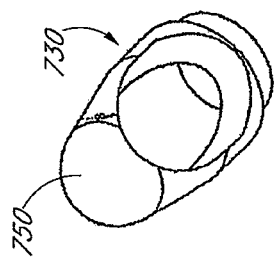
FIG. 15W1

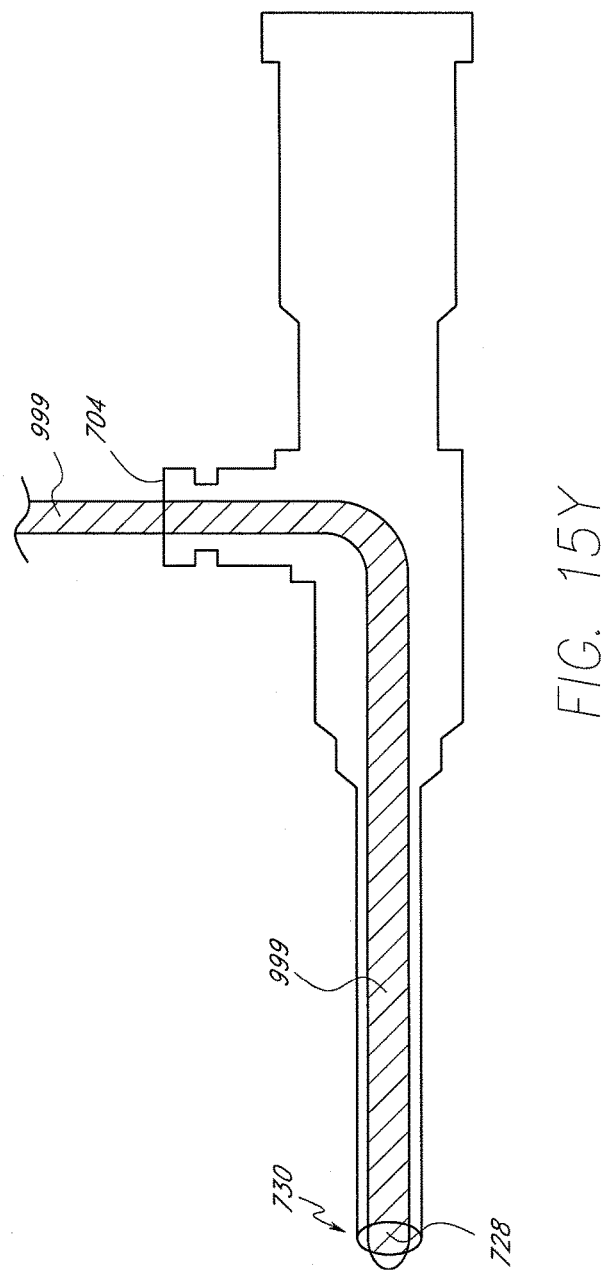

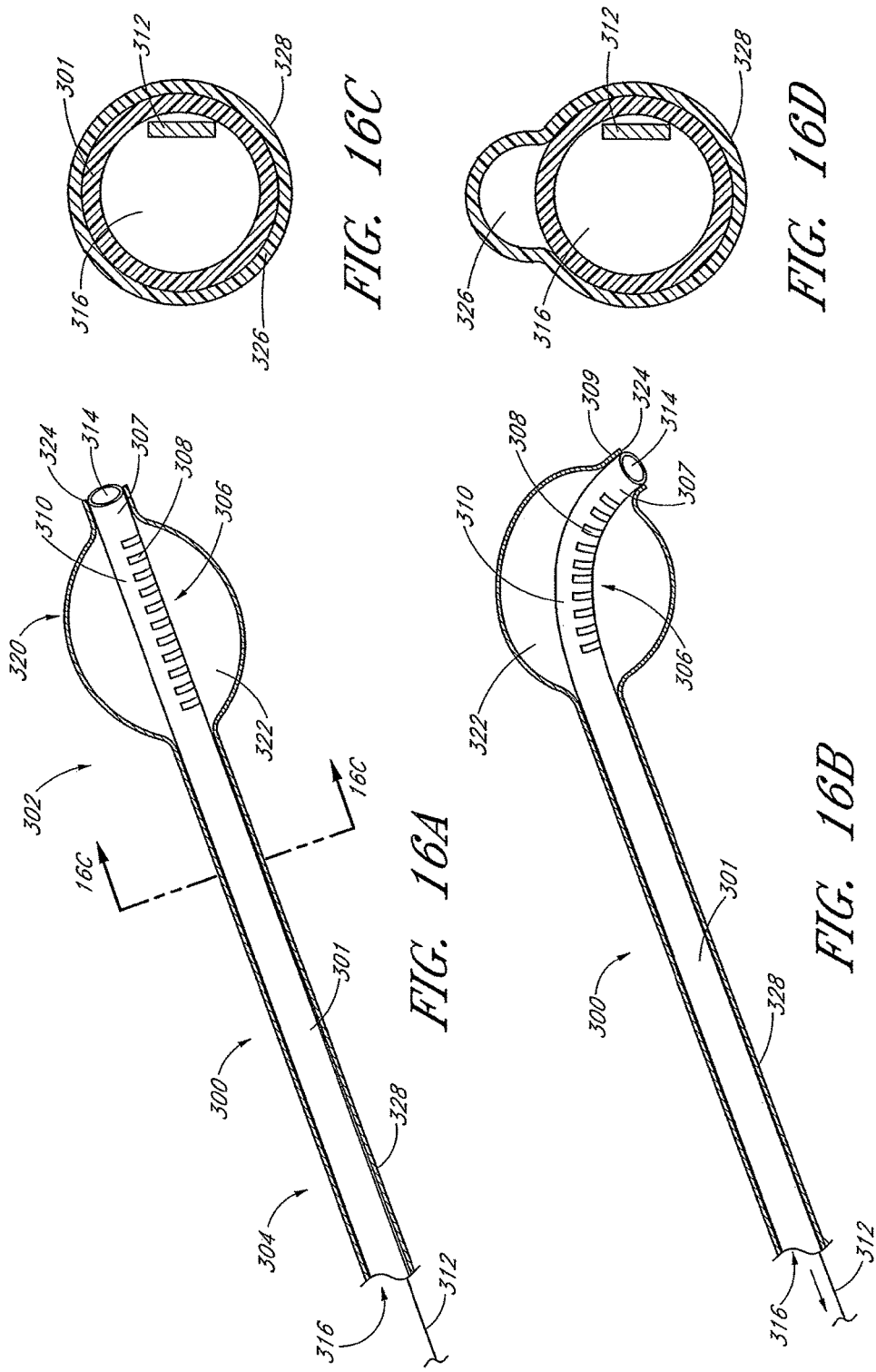

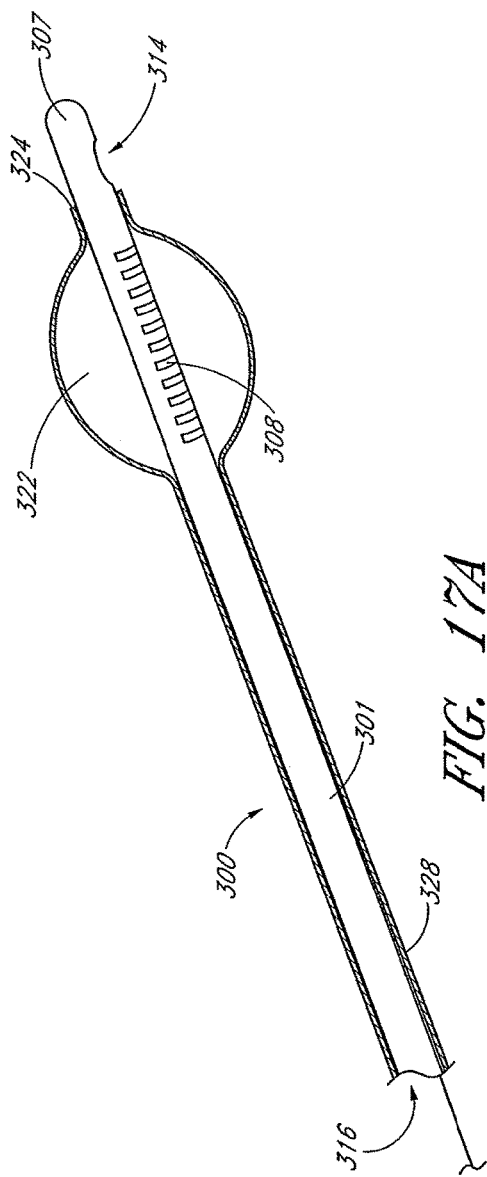
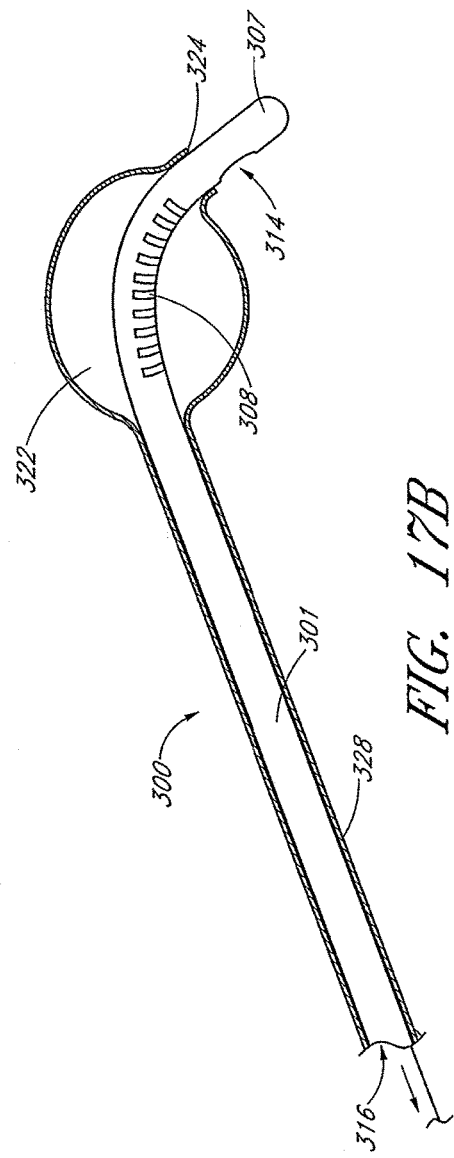
FIG. 17A
FIG. 17B

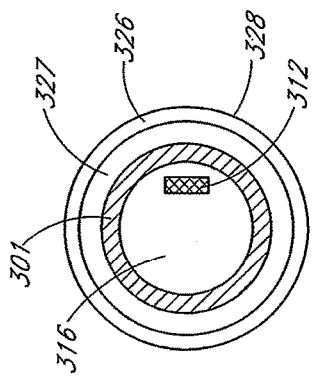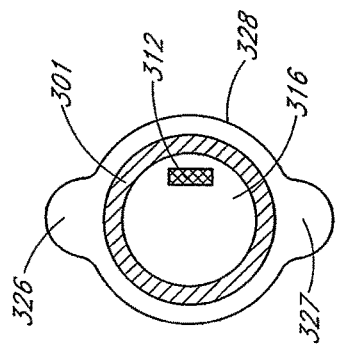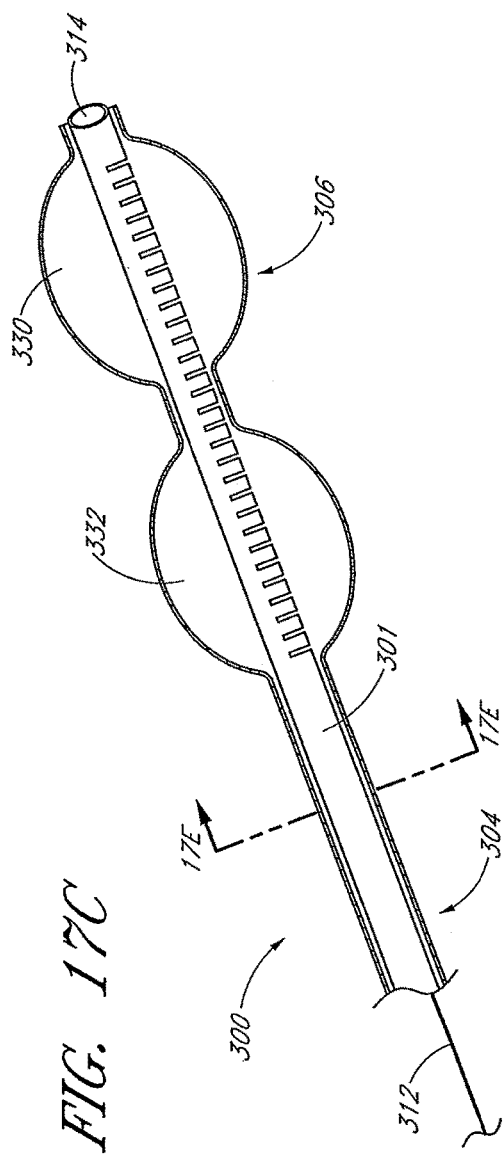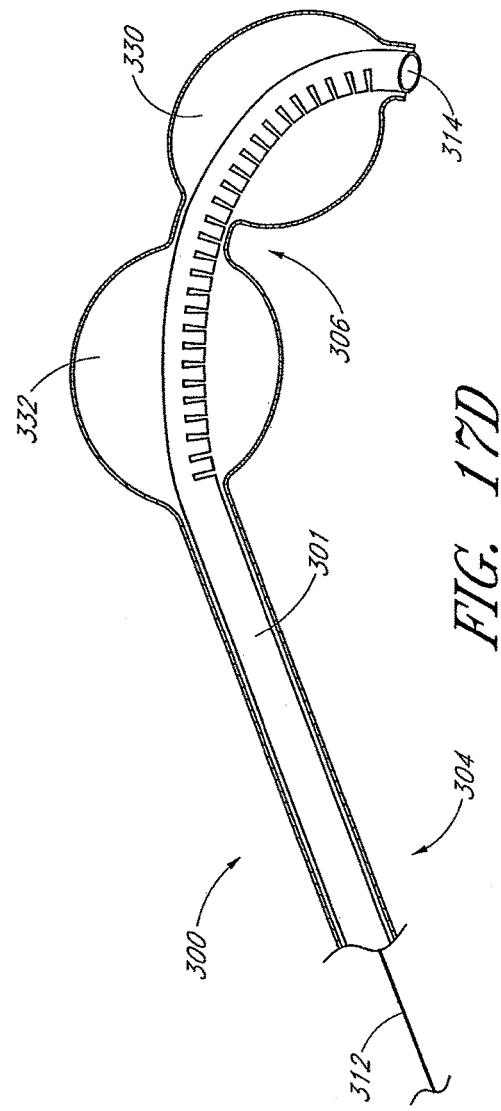

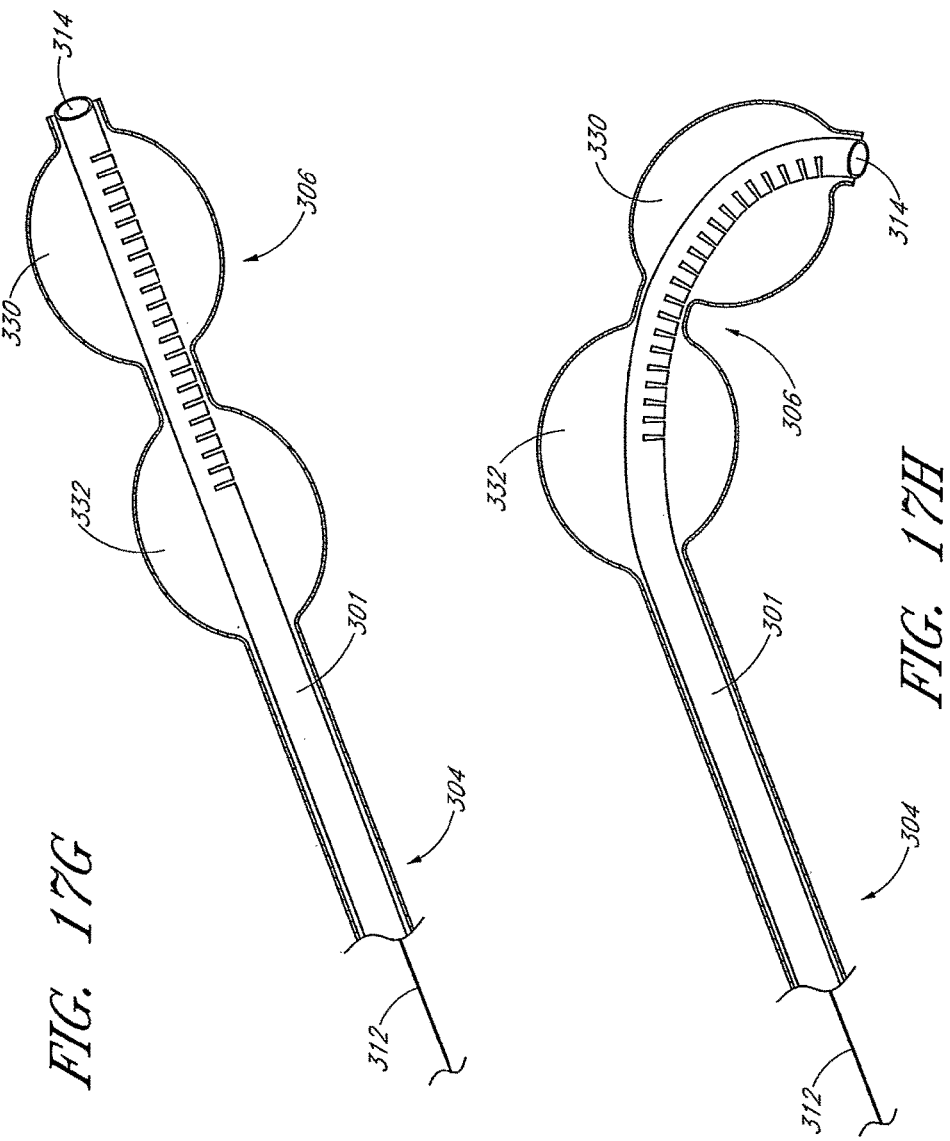

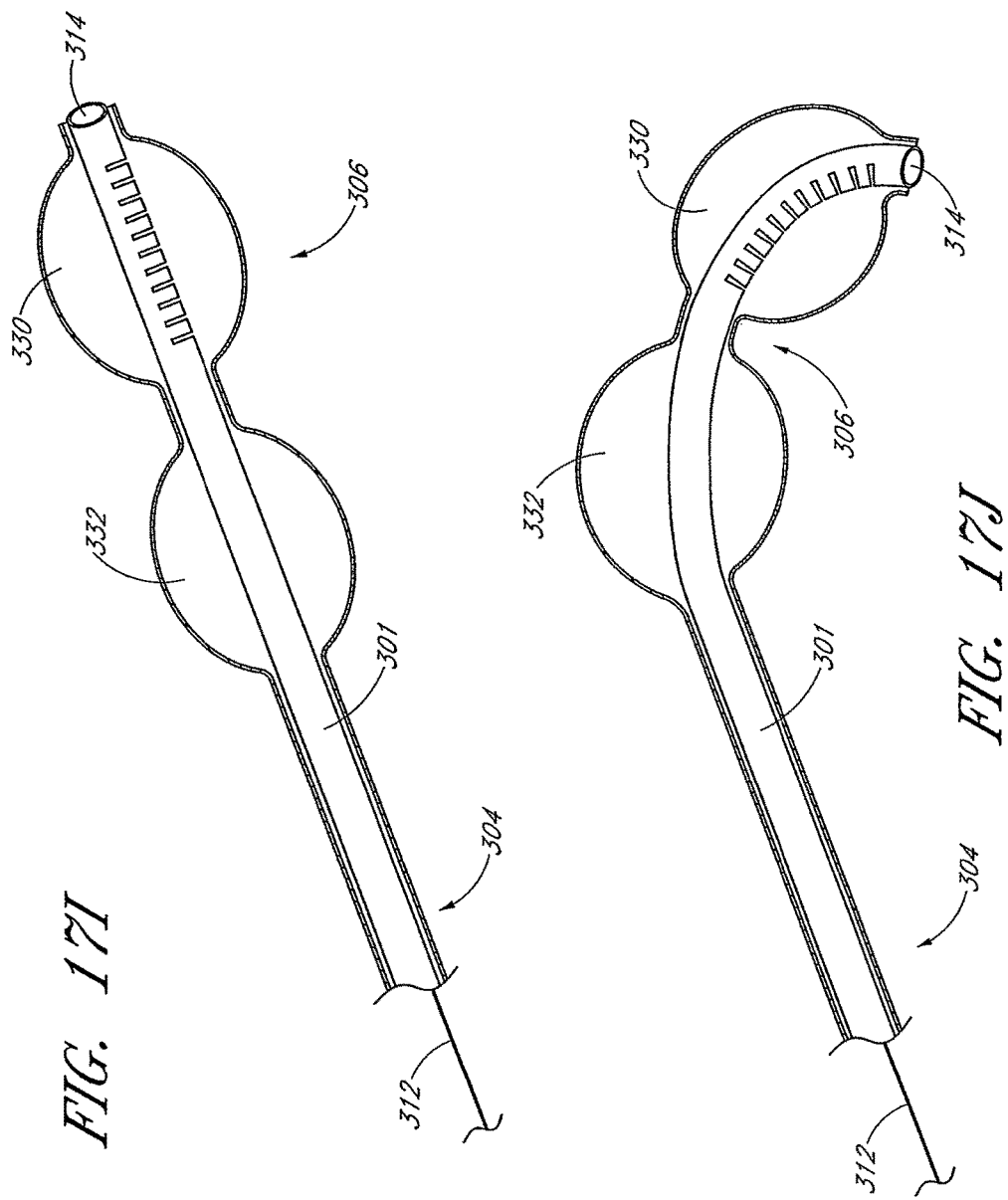

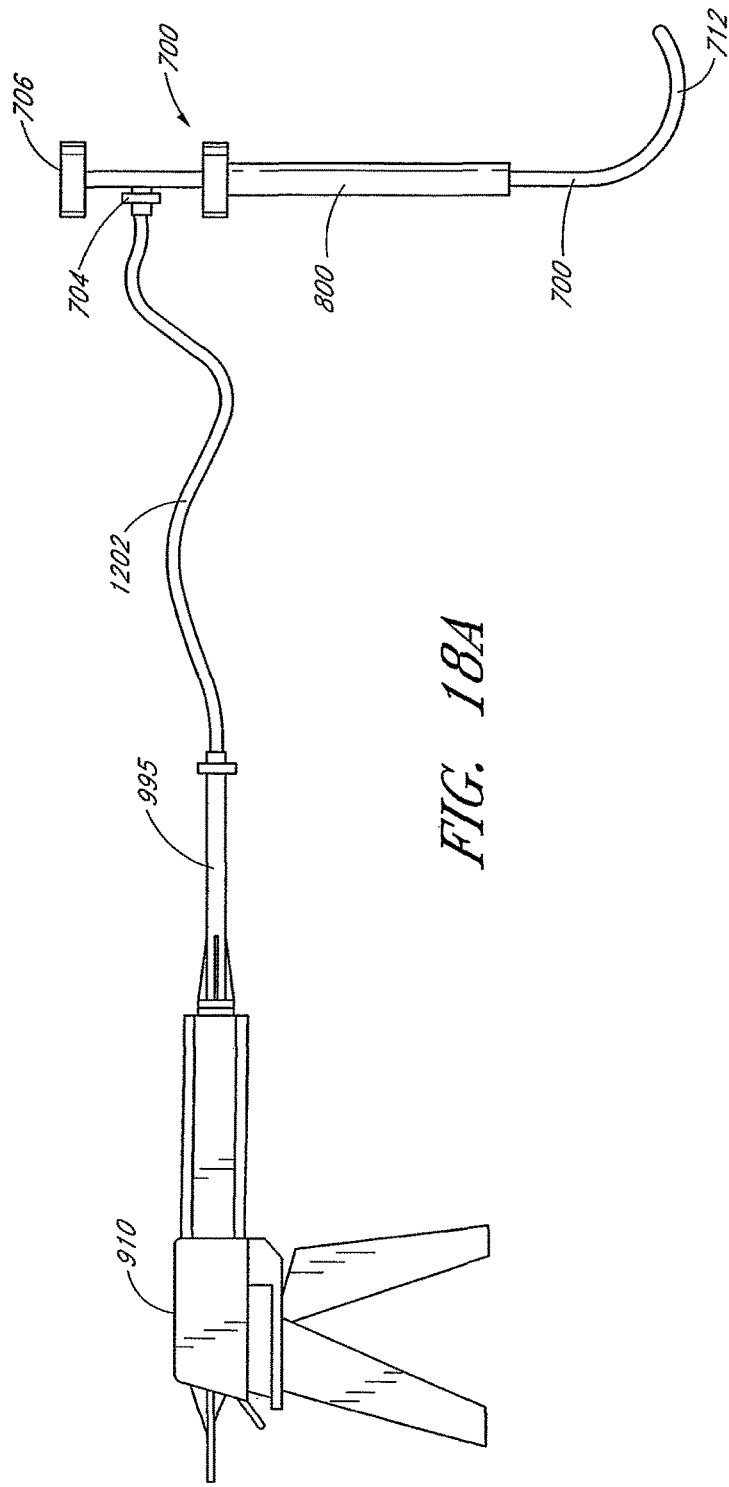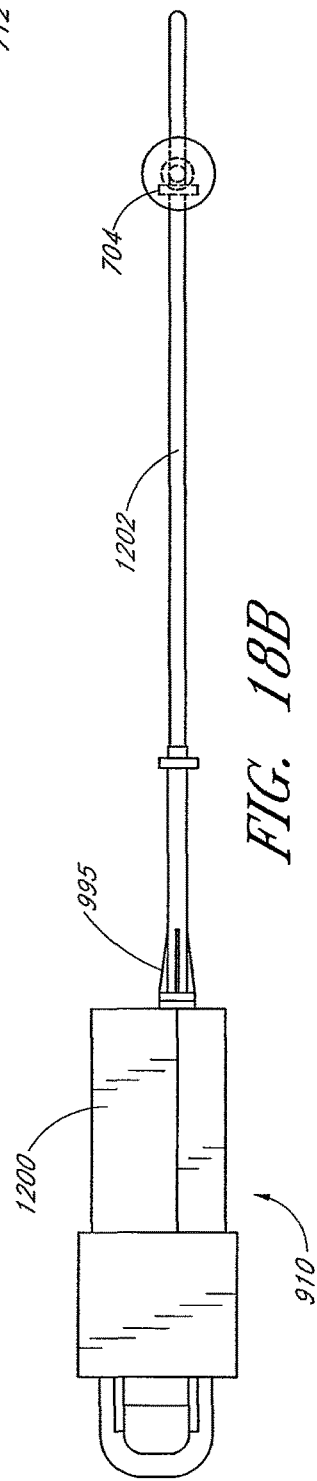
FIG. 18A
FIG. 18B

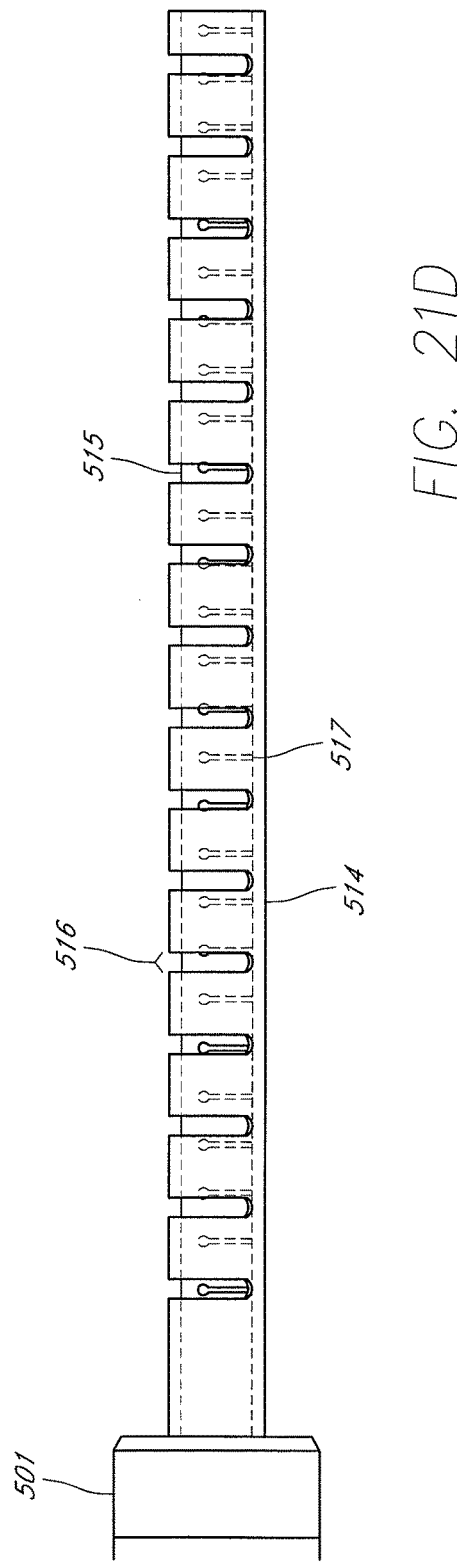

STEERABLE AND CURVABLE CAVITY CREATION SYSTEM

PRIORITY CLAIM

This application claims priority under 35 U.S.C. §120 as a continuation of U.S. patent application Ser. No. 13/461,727 filed on May 1, 2012, which is in turn a continuation-in-part of U.S. patent application Ser. No. 13/182,335 filed on Jul. 13, 2011, which is a continuation of U.S. patent application Ser. No. 12/954,511 filed on Nov. 24, 2010, which in turn claims priority under 35 U.S.C. §119(e) as a nonprovisional of U.S. Provisional Application No. 61/264,640 filed Nov. 25, 2009, U.S. Provisional Application No. 61/296,013 filed Jan. 18, 2010, and U.S. Provisional Application No. 61/300,401 filed Feb. 1, 2010, and under 35 U.S.C. §120 as a continuation-in-part of U.S. patent application Ser. No. 12/469,654 filed May 20, 2009, which is a continuation-in-part of U.S. patent application Ser. No. 12/029,428 filed Feb. 11, 2008, which is a continuation-in-part of U.S. patent application Ser. No. 11/941,764 filed on Nov. 16, 2007. U.S. patent application Ser. No. 13/461,727 filed on May 1, 2012 also claims priority under 35 U.S.C. §120 as a continuation-in-part of PCT/US/2010/058108 filed on Nov. 24, 2010, which in turn claims priority under 35 U.S.C. §119(e) as a nonprovisional of U.S. Provisional Application No. 61/264,640 filed Nov. 25, 2009, U.S. Provisional Application No. 61/296,013 filed Jan. 18, 2010, and U.S. Provisional Application No. 61/300,401 filed Feb. 1, 2010. U.S. patent application Ser. No. 13/461,727 filed on May 1, 2012 also claims priority under 35 U.S.C. §120 as a continuation-in-part of U.S. patent application Ser. No. 13/452,784 filed Apr. 20, 2012, which is a continuation of U.S. patent application Ser. No. 12/029,428 filed Feb. 11, 2008, which is a continuation-in-part of U.S. patent application Ser. No. 11/941,764 filed on Nov. 16, 2007. All of the aforementioned priority applications are hereby incorporated by reference in their entireties.

BACKGROUND OF THE INVENTION

1. Field of the Invention

The invention relates, in some embodiments, to bone augmentation devices and procedures. In particular, the present invention relates to steerable and curvable injection devices and systems for introducing conventional or novel bone cement formulations such as in performing vertebroplasty.

2. Description of the Related Art

According to the National Osteoporosis Foundation ten million Americans have osteoporosis (OSP), and an estimated 34 million with low bone mass are at risk of developing osteoporosis (http://www.nof.org/osteoporosis/diseasefacts.htm). Called the "silent disease," OSP develops slowly over a number of years without symptoms. Eighty percent of those affected are women, particularly petite Caucasian and Asian women, although older men and women of all races and ethnicities are at significant risk.

In the United States, 700,000 people are diagnosed with vertebral compression fractures as a result of OSP each year. Morbidity associated with vertebral fractures includes severe back pain, loss of height and deformity, all of which negatively affect quality of life.

Once microfracture of the vertebra begins, there is little the clinician can do except palliative medical treatment using analgesics, bed rest and/or restriction of activity. With time, the microfractures widen at one level and without surgical intervention, the fractures cascade downward with increasing kyphosis or "hunching" of the back. Once a mechanical lesion develops, surgery is often the only practical option. Vertebroplasty or kyphoplasty are the primary minimally-invasive surgical procedures performed for the treatment of compression-wedge fractures due to OSP.

Vertebroplasty stabilizes the collapsed vertebra by injecting polymethylmethacrylate (PMMA) or a substantially equivalent bone cement into cancellous bone space of the vertebrae. Besides providing structural support to the vertebra, the exothermic reaction of PMMA polymerization is said to kill off the nociceptors or pain receptors in the bone, although no proof of this hypothesis has been provided in the literature. This procedure is typically performed as an out-patient procedure and requires only a short-acting local or general anesthetic. Once the surgical area of the spine is anesthetized, the physician inserts one or two needles through small skin incisions into either the pedicle (uni-transpedicular) or the pedicles of the vertebral body i.e., bi-transpedicular. Polymethylmethacrylate (PMMA) is injected through the needle and into the cancellous-bone space of the vertebra.

Kyphoplasty mirrors the vertebroplasty procedure but has the additional step of inserting and expanding a nylon or polyurethane balloon in the interior of the vertebral body. Expansion of the balloon under pressure reduces the compression fracture and creates a cavity. After withdrawal of the balloon, PMMA is injected into the cavity to stabilize the reduction. The kyphoplasty procedure may restore the vertebral body height. Kyphoplasty is an in-patient surgery that requires hospitalization and a general anesthetic. Kyphon Inc. claims over 275,000 spinal fractures have been treated using their PMMA derivative and their "balloon" kyphoplasty procedure worldwide (Sunnyvale, Calif., Sep. 5, 2006, (PR NEWS WIRE) Kyphon study 2006).

Bone cement for both vertebroplasty and kyphoplasty procedures currently employ variations of standard PMMA in a powder and a methyl methacrylate monomer liquid. When the powder and liquid monomer are mixed, an exothermic polymerization takes place resulting in the formation of a "dough-like" material, which is then inserted into the cancellous bone space. The dough, when hardened, becomes either the reinforcing structure or the grout between the bone and prosthesis in the case of total joint replacement.

The average clinical in vivo life of the PMMA grout is approximately 10 years due to corrosion fatigue of either the bone-cement/prosthesis and/or the bone cement/bone interfaces. Jasty et al. (1991) showed that in cemented total hip replacements: "Fractures in the cement mantle itself were found on cut sections around all prostheses which had been in use for over three years." Jasty et al. also noted: "In general, specimens less than 10 years in situ showed small incomplete fractures while the specimens in place more than 10 years all showed large complete cement mantle fractures."

When an implant fails, a revision becomes almost mandatory. After removal of the cement and hardware, a cemented arthroplasty can be repeated if enough cancellous bone matrixes exist to grip the new PMMA. Alternatively, cement-less prostheses can be installed. Such a revision, however, can only be applied to total joint replacement failures. For vertebroplasty and/or kyphoplasty, a classical screw and plate internal fixation with autograft fusion is necessary.

Despite advances in the foregoing procedures, there remains a need for improved bone cement delivery systems which enable rapid and controllable deployment of bone cement for the treatment of conditions such as vertebral compression fractures.

SUMMARY OF THE INVENTION

There is provided in accordance with one aspect of the present invention, a steerable and curvable vertebroplasty device having a cavity creation element. The vertebroplasty device comprises an elongate tubular body, having a proximal end, a distal end, and a central lumen extending therethrough. A deflectable zone is provided on the distal end of the tubular body, for deflection through an angular range. A handle is provided on the proximal end of the tubular body, having a deflection controller thereon. A cavity creating element may be carried by the deflectable zone. In one embodiment, the cavity creating element is an inflatable balloon, in communication with a proximal inflation port by way of an elongate inflation lumen extending throughout the length of the tubular body.

The deflection controller may comprise a rotatable element, such as a knob rotatable about the longitudinal axis of the handle.

The distal end of the tubular body is provided with at least one exit port in communication with the central lumen. The exit port may open in a lateral direction, an axial direction, or along an inclined surface positioned distally of a transition point between the longitudinal side wall of the tubular body and the distal end of the distal tip.

In another aspect of the invention, disclosed is a steerable and curvable vertebroplasty device having a plurality of cavity creation elements. The device can include an elongate, tubular body, having a proximal end, a distal end, and a central lumen extending therethrough; a deflectable zone on the distal end of the tubular body, deflectable through an angular range; a handle on the proximal end of the tubular body; and a deflection controller on the handle; a first cavity creating element carried by the deflectable zone; and a second cavity creating element on the elongate tubular body. The second cavity creating element can be carried at least partially by the deflectable zone. The first and/or second cavity creating element can be a balloon. The first and second cavity creating elements can share a common inflation lumen, or have separate lumens. The first cavity creating element and/or second cavity creating element could be positioned proximal to, or distal to one or more exit ports on the tubular body. The first and/or cavity creating element could include a filament layer, such as a braided layer.

A method of performing vertebroplasty is also disclosed herein, according to some embodiments. The method can include the steps of: creating a pedicular access channel in a pedicle to access the interior of a vertebral body; inserting an introducer cannula into the pedicle; inserting a steerable and curvable injection needle through the introducer cannula into the interior of a vertebral body, the steerable and curvable injection needle having a proximal end and a distal end, the distal end having a first configuration substantially coaxial with a long axis of the proximal end, the steerable and curvable injection needle also having a first cavity creating element and a second cavity creating element; rotating a control to deflect the distal end of the steerable and curvable injection needle to a second configuration that is not substantially coaxial with the long axis of the proximal end; actuating the first cavity creating element to create a first cavity within the interior of the vertebral body; actuating a second cavity creating element to create a second cavity within the interior of the vertebral body; and flowing bone cement through the steerable and curvable injection needle into the interior of the vertebral body.

In some embodiments, flowing bone cement through the steerable and curvable injection needle into the interior of the vertebral body comprises releasing a first particle-containing bone cement within the interior of the vertebral body, the bone cement comprising at least 30%, 35%, 40%, 45%, 50%, or more particles by weight, and additionally comprises releasing a second particle-containing bone cement within the first bone cement, the second particle-containing bone cement comprising less than about 35%, 30%, 25%, 20%, or less particles by weight.

In another embodiment, disclosed herein is a steerable and curvable vertebroplasty device, that can include an elongate, tubular body, having a proximal end, a distal end, and a central lumen extending therethrough; a deflectable zone on the distal end of the tubular body, deflectable through an angular range; a handle on the proximal end of the tubular body; a deflection controller on the handle; and a cavity creating element carried by the deflectable zone, wherein the cavity creating element comprises a filament layer.

In still another embodiment, disclosed is a steerable and curvable vertebroplasty device that includes an elongate, tubular body, having a proximal end, a distal end, and a central lumen extending therethrough; a deflectable zone on the distal end of the tubular body, deflectable through an angular range; a handle on the proximal end of the tubular body; a deflection controller on the handle; and a cavity creating element carried by the deflectable zone, wherein the cavity creating element comprises a plurality of concentric balloons.

Also disclosed herein is a steerable vertebroplasty device, comprising an elongate, tubular body having a proximal end, a distal end, and a central lumen extending therethrough. The distal end can include a closed distal-facing surface and a lateral-facing surface comprising an exit aperture in connection with the central lumen. The exit port is defined by at least a first angled surface. Some apertures can include a first angled surface and a second angled surface, the first angled surface opposing and being non-parallel to the second angled surface. The device can also include a deflectable zone on the distal end of the tubular body, deflectable through an angular range; the deflectable zone having a proximal portion and a distal portion. The elongate tubular body has a longitudinal axis extending from the proximal end to the proximal portion of the deflectable zone. The deflectable zone is movable from a first configuration coaxial with the first longitudinal axis in an unstressed state to a second deflected configuration. The device can also have a handle on the proximal end of the tubular body, a deflection control on the handle, and an input port for receiving bone cement. The first angled surface and the second angled surface can have longitudinal axes that intersect and form an angle of between about, for example, 30 degrees and 150 degrees, 60 degrees and 120 degrees, 75 degrees and 105 degrees, or about 90 degrees in some embodiments. The distal end can include an end cap operably attached to the tubular body, and in some embodiments have a zone having a radially inwardly tapering diameter. The first radial surface can include a proximal radial termination, and the second radial surface can include a distal radial termination. The proximal radial termination can be radially offset from the distal radial termination by at least about 0.01 inches, 0.05 inches, 0.10 inches, or more. The exit aperture can include a rippled zone.

Also disclosed herein is a steerable vertebroplasty device having an elongate, tubular body having a proximal end, a distal end, and a central lumen extending therethrough. The distal end can include a closed distal-facing surface and a lateral-facing surface comprising an exit port in connection with the central lumen. The exit port can be defined by a first wall and a second wall that is not parallel to the first wall. The exit port can have a first inner axial or circumferential dimension at a junction with the central lumen and a second outer axial or circumferential dimension where bone cement exits the device. The second dimension can be less than, equal to, or greater than the first dimension, such as by about 5%, 10%, 15%, 20%, 25%, 35%, 40%, 50%, 75%, 100%, or more. The device can also include a deflectable zone on the distal end of the tubular body, deflectable through an angular range. The deflectable zone can have a proximal portion and a distal portion. The elongate tubular body has a first longitudinal axis extending from the proximal end to the proximal portion of the deflectable zone. The deflectable zone is movable from a first substantially straight configuration in an unstressed state to a second deflected configuration. The device also can include a handle on the proximal end of the tubular body, a deflection control on the handle, and an input port for receiving bone cement, the input port having a second longitudinal axis spaced apart from and at an angle with respect to the first longitudinal axis, the input port positioned distally on the elongate, tubular body relative to the deflection control.

In another aspect, disclosed herein is a method for treating a bone. The method can include the steps of creating a pedicular access channel in a pedicle to access the interior of a vertebral body; inserting an introducer cannula into the pedicle; inserting a steerable injection needle through the introducer cannula into the interior of a vertebral body, the steerable injection needle having a proximal end, a tubular body having a longitudinal axis, and a distal end, a control for controlling deflection of the distal end, and an input port having a longitudinal axis and configured to receive bone cement, wherein the control is positioned proximally to the input port, wherein the longitudinal axis of the input port is not coaxial with the longitudinal axis of the tubular body, wherein the distal end has a first configuration substantially coaxial with the longitudinal axis of the tubular body, wherein the distal end comprises a closed distal-facing surface and a lateral-facing surface comprising an exit aperture in connection with a central lumen, the exit aperture defined by a first angled surface and a second angled surface, the first angled surface opposing and being non-parallel to the second angled surface; adjusting the control to deflect the distal end of the steerable injection needle to a second configuration that is not substantially coaxial with the longitudinal axis of the tubular body; and flowing bone cement through the steerable injection needle, out the exit aperture and into the interior of the vertebral body. In some embodiments, the exit aperture has a first inner axial or circumferential dimension at a junction with the central lumen and a second outer axial or circumferential dimension where bone cement exits the needle, wherein the second dimension is greater than, equal to, or less than the first width.

In some embodiments, disclosed is a steerable cavity creation device. The device can include an elongate, tubular body having a proximal end, a distal end, a lumen extending therethrough, a first hypotube, and a second hypotube disposed within the first hypotube. The device can also include a deflectable zone on the distal end of the tubular body, deflectable through an angular range, the deflectable zone having a proximal portion and a distal portion. The first hypotube can have a distal zone having a first plurality of slots, and the second hypotube has a distal zone having a second plurality of slots. The first plurality of slots can be oriented 180 degrees circumferentially apart from the second plurality of slots. The elongate tubular body can have a first longitudinal axis extending from the proximal end to the proximal portion of the deflectable zone. The deflectable zone can be movable from a first substantially straight configuration in an unstressed state to a second deflected configuration. The device can include a handle on the proximal end of the tubular body, as well as a deflection control on the handle actuated by rotation about the first longitudinal axis of the tubular body. Upon rotation of the deflection control, a proximally directed force is exerted on a movable actuator attached to the second hypotube to actively change the curvature of the deflectable zone. The device can also include an input port. The input port can have a second longitudinal axis spaced apart from and at an angle with respect to the first longitudinal axis. The input port can be positioned distally on the elongate, tubular body relative to the deflection control. The device can also include a cavity creating element carried by the deflectable zone. Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 1 is a perspective view of a steerable and curvable injection needle in accordance with one aspect of the present invention.

FIG. 2 is a perspective view of an introducer in accordance with one aspect of the present invention.

FIG. 3 is a perspective view of a stylet in accordance with one aspect of the present invention.

FIG. 7A is a schematic view of a distal portion of the steerable and curvable needle of FIG. 6, shown in a linear configuration.

FIG. 7B is a schematic view as in FIG. 7A, following proximal retraction of a pull wire to laterally deflect the distal end.

FIGS. 12 and 13 illustrate a further variation of the deflectable needle design in accordance with the present invention.

FIGS. 16A and 16B are schematic illustrations of the distal end of a steerable and curvable injection device in accordance with the present invention, having a cavity creating element thereon.

FIGS. 16C and 16D are alternative cross sectional views taken along the line 16C-16C in FIG. 16A, showing different inflation lumen configurations.

FIGS. 17A and 17B illustrate an alternative steerable and curvable injection device having a cavity creation element thereon.

FIGS. 17C and 17D illustrate an alternative steerable and curvable injection device having a plurality of cavity creation elements thereon.

FIGS. 17E and 17F are alternative cross sectional views showing different inflation lumen configurations.

FIGS. 17G-17J illustrate further alternative steerable and curvable injection devices having a plurality of cavity creation elements thereon.

FIGS. 18A and 18B are schematic views of a bone cement delivery system in accordance with the present invention.

FIGS. 21A-21E illustrate various views of an embodiment of a cavity creation device.

DETAILED DESCRIPTION OF THE PREFERRED EMBODIMENT

Figure 4:
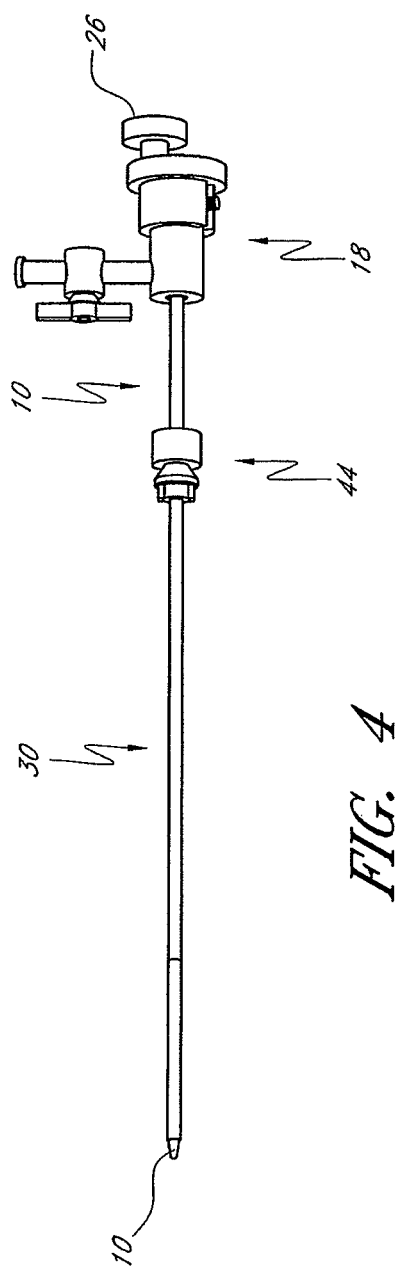
FIG. 4 is a side elevational view of the steerable and curvable injection needle moveably coaxially disposed within the introducer, in a substantially linear configuration.

The present invention provides improved delivery systems for delivery of a bone cement or bone cement composite for the treatment of vertebral compression fractures due to osteoporosis (OSP), osteo-trauma, and benign or malignant lesions such as metastatic cancers and myeloma, and associated access and deployment tools and procedures.

Also incorporated by reference in their entirety herein are U.S. patent application Ser. No. 11/941,764 filed Nov. 16, 2007, U.S. patent application Ser. No. 12/029,428 filed Feb. 11, 2008, and U.S. patent application Ser. No. 12/469,654 filed May 20, 2009 which also describe various systems and methods for performing verterbroplasty including steerable, curvable vertebroplasty devices.

The primary materials in the preferred bone cement composite are methyl methacrylate and inorganic cancellous and/or cortical bone chips or particles. Suitable inorganic bone chips or particles are sold by Allosource, Osteotech and LifeNet (K053098); all have been cleared for marketing by FDA. The preferred bone cement also may contain the additives: barium sulfate for radio-opacity, benzoyl peroxide as an initiator, N,N-dimethyl-p-toluidine as a promoter and hydroquinone as a stabilizer. Other details of bone cements and systems are disclosed in U.S. patent application Ser. No. 11/626,336, filed Jan. 23, 2007, the disclosure of which is hereby incorporated in its entirety herein by reference.

One preferred bone cement implant procedure involves a two-step injection process with two different concentrations of the bone particle impregnated cement. To facilitate the implant procedure the bone cement materials are packaged in separate cartridges containing specific bone cement and inorganic bone particle concentrations for each step. Tables 1 and 2, infra, list one example of the respective contents and concentrations in Cartridges 1A and 1B for the first injection step, and Cartridges 2A and 2B for the second injection step.

The bone cement delivery system generally includes at least three main components: 1) stylet; 2) introducer cannula; and 3) steerable and curvable injection needle. See FIGS. 1-3. Packaged with the system or packaged separately is a cement dispensing pump. The complete system also preferably includes at least one cement cartridge having at least two chambers therein, and a spiral mixing nozzle.

The stylet is used to perforate a hole into the pedicle of the vertebra to gain access to the interior of the vertebral body.

The introducer cannula is used for bone access and as a guide for the steerable and curvable injection needle. The introducer cannula is sized to allow physicians to perform vertebroplasty or kyphoplasty on vertebrae with small pedicles such as the thoracic vertebra T5 as well as larger vertebrae L5. In addition, this system is designed for uni-transpedicular access and/or bi-pedicular access.

Once bone access has been achieved, the steerable and curvable injection needle can be inserted through the introducer cannula into the vertebra. The entire interior vertebral body may be accessed using the steerable and curvable injection needle. The distal end of the needle can be manually shaped to any desired radius within the product specifications. The radius is adjusted by means of a knob on the proximal end of the device.

The hand-held cement dispensing pump may be attached to the steerable and curvable injection needle by a slip-ring luer fitting. The pre-filled 2-chambered cartridges (1A and 1B, and 2A and 2B) are loaded into the dispensing pump. As the handle of the dispensing pump is squeezed, each piston pushes the cartridge material into the spiral mixing tube. The materials are mixed in the spiral mixing nozzle prior to entering the steerable and curvable injection needle. The ratio of diameters of the cartridge chambers determines the mixing ratio for achieving the desired viscosity.

The bone cement implant procedures described herein use established vertebroplasty and kyphoplasty surgical procedures to stabilize the collapsed vertebra by injecting bone cement into cancellous bone.

The preferred procedure is designed for uni-transpedicular access and may be accomplished under either a local anesthetic or short-duration general anesthetic. Once the area of the spine is anesthetized, an incision is made and the stylet is used to perforate the vertebral pedicle and gain access to the interior of the vertebral body. The introducer cannula is then inserted and acts as a guide for the steerable and curvable injection needle.

Injection of the preferred bone cement involves a two-step procedure. The pre-filled Cartridges 1A and 1B are loaded into the dispensing pump. As the dispensing pump handle is squeezed, each piston pushes material into the spiral mixing tube. The diameter of each chamber may be utilized to determine the mixing ratio for achieving the desired viscosity.

The first step involves injecting a small quantity of PMMA with more than about 35%, e.g., 60% inorganic bone particles, onto the outer periphery of the cancellous bone matrix, i.e., next to the inner wall of the cortical bone of the vertebral body. The cement composite is designed to harden relatively quickly, forming a firm but still pliable shell. This shell is intended to prevent bone marrow/PMMA content from being ejected through any venules or micro-fractures in the vertebral body wall. The second step of the procedure involves a second injection of PMMA with an approximately 30% inorganic bone particles to stabilize the remainder of the weakened, compressed cancellous bone.

Alternatively, the steerable and curvable needle disclosed herein and discussed in greater detail below, can be used in conventional vertebroplasty procedures, using a single step bone cement injection.

Injection control for the first and second steps is provided by a 2 mm ID flexible injection needle, which is coupled to the hand operated bone cement injection pump. The 60% (>35%) and 30% ratio of inorganic bone particle to PMMA concentrations may be controlled by the pre-filled cartridge sets 1A and B, and 2A and 2B. At all times, the amount of the injectate is under the direct control of the surgeon or intervention radiologist and visualized by fluoroscopy. The introducer cannula is slowly withdrawn from the cancellous space as the second injection of bone cement begins to harden, thus preventing bone marrow/PMMA content from exiting the vertebral body. The procedure concludes with closure of the surgical incision with bone filler. In vitro and in vivo studies have shown that the 60% (>35%) bone-particle impregnated bone cement hardens in 2-3 minutes and 30% bone-particle impregnated bone cement hardens between 4 to 10 minutes.

Details of the system components will be discussed below.

There is provided in accordance with the present invention a steerable and curvable injection device that can be used to introduce any of a variety of materials or devices for diagnostic or therapeutic purposes. In one embodiment, the system is used to inject bone cement, e.g., PMMA or any of the bone cement compositions disclosed elsewhere herein. The injection system most preferably includes a tubular body with a steerable and curvable (i.e., deflectable) distal portion for introducing bone cement into various locations displaced laterally from the longitudinal axis of the device within a vertebral body during a vertebroplasty procedure.

Referring to FIG. 1, there is illustrated a side perspective view of a steerable and curvable injection needle 10 in accordance with one aspect of the present invention. The steerable and curvable injection needle 10 comprises an elongate tubular body 12 having a proximal end 14 and a distal end 16. The proximal end 14 is provided with a handle or manifold 18, adapted to remain outside of the patient and enable introduction and/or aspiration of bone cement or other media, and control of the distal end as will be described herein. In general, manifold 18 is provided with at least one injection port 20, which is in fluid communication with a central lumen (not illustrated) extending through tubular body 12 to at least one distal exit port 22.

The manifold 18 is additionally provided with a control 26 such as a rotatable knob, slider, or other moveable control, for controllably deflecting a deflection zone 24 on the distal end 16 of the tubular body 12. As is described elsewhere herein, the deflection zone 24 may be advanced from a relatively linear configuration as illustrated in FIG. 1 to a deflected configuration throughout an angular range of motion.

Referring to FIG. 2, there is illustrated an elongate tubular introducer 30, having a proximal end 32, a distal end 34 and an elongate tubular body 36 extending there between. A central lumen 38 (not shown) extends between a proximal access port 40 and a distal access port 42.

The central lumen 38 has an inside diameter which is adapted to slide axially to receive the steerable and curvable injection needle 10 therethrough. This enables placement of the distal end 34 adjacent a treatment site within the body, to establish an access pathway from outside of the body to the treatment site. As will be appreciated by those of skill in the art, the introducer 30 enables procedures deep within the body such as within the spine, through a minimally invasive and/or percutaneous access. The steerable and curvable injection needle 10 and/or other procedure tools may be introduced into port 40, through lumen 38 and out of port 42 to reach the treatment site.

The proximal end 32 of introducer 30 may be provided with a handle 44 for manipulation during the procedure. Handle 44 may be configured in any of a variety of ways, such as having a frame 46 with at least a first aperture 48 and a second aperture 50 to facilitate grasping by the clinician.

Referring to FIG. 3, there is illustrated a perspective view of stylet 60. Stylet 60 comprises a proximal end 62, a distal end 64 and an elongate body 66 extending there between. The proximal end 62 may be provided with a stop 68 such as a grasping block, manifold or other structure, to facilitate manipulation by the clinician. In the illustrated embodiment, block 68 is configured to nest within a recess 70 on the proximal end of the introducer 30.

As will be appreciated by those of skill in the art, the stylet 60 has an outside diameter which is adapted to coaxially slide within the central lumen on introducer 30. When block 68 is nested within recess 70, a distal end 64 of stylet 60 is exposed beyond the distal end 34 of introducer 30. The distal end 64 of stylet 60 may be provided with a pointed tip 72, such as for anchoring into the surface of a bone.

Referring to FIG. 4, there is illustrated a side elevational view of an assembly in accordance with the present invention in which a steerable and curvable injection needle 10 is coaxially positioned within an introducer 30. The introducer 30 is axially moveably carried on the steerable and curvable injection needle 10. In the illustration of FIG. 4, the introducer 30 is illustrated in a distal position such that it covers at least a portion of the deflection zone 24 on injection needle 10.

Figure 5:
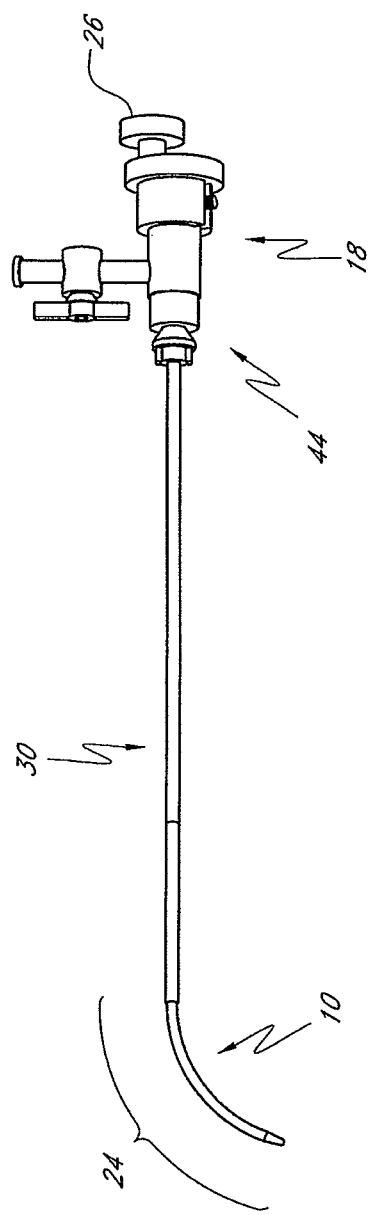
FIG. 5 is a side elevational view of the assembly of FIG. 4, showing the steerable and curvable injection needle in a curved configuration.

FIG. 5 illustrates an assembly as in FIG. 4, in which the introducer 30 has been proximally retracted along the injection needle 10 to fully expose the deflection zone 24 on injection needle 10. In addition, the control 26 has been manipulated to deflect the deflection zone 24 through an angle of approximately 90°. Additional details of the steerable and curvable needle will be discussed below.

Figure 6:
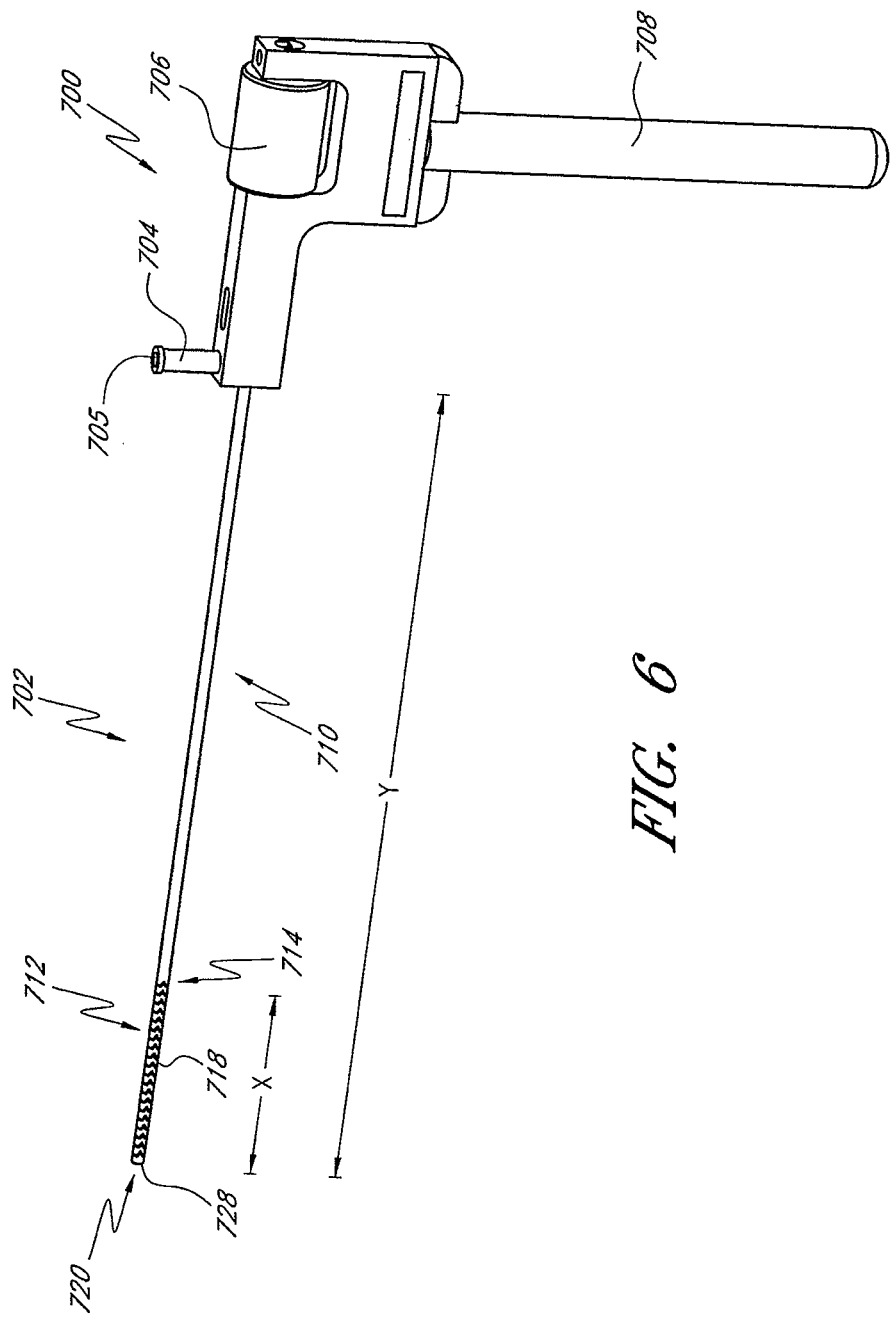
FIG. 6 is a side elevational schematic view of another steerable and curvable injection needle in accordance with the present invention.

FIG. 6 illustrates a schematic perspective view of an alternate steerable and curvable vertebroplasty injector, according to one embodiment of the invention. The steerable and curvable injector 700 includes a body or shaft portion 702 that is preferably elongate and tubular, input port 704, adjustment control 706, and handle portion 708. The elongate shaft 702 preferably has a first proximal portion 710 and a second distal portion 712 which merge at a transition point 714. Shaft 702 may be made of stainless steel, such as 304 stainless steel, Nitinol, Elgiloy, or other appropriate material. Alternatively, the tubular body 702 may be extruded from any of a variety of polymers well known in the catheter arts, such as PEEK, PEBAX, nylon and various polyethylenes. Extruded tubular bodies 702 may be reinforced using metal or polymeric spiral wrapping or braided wall patterns, as is known in the art.

The shaft 702 defines at least one lumen therethrough that is preferably configured to carry a flowable bone cement prior to hardening. Proximal portion 710 of shaft 702 is preferably relatively rigid, having sufficient column strength to push through cancellous bone. Distal portion 712 of shaft 702 is preferably flexible and/or deflectable and reversibly actuatable between a relatively straight configuration and one or more deflected configurations or curved configurations as illustrated, for example, in FIG. 5, as will be described in greater detail below. The distal portion 712 of shaft 702 may include a plurality of transverse slots 718 that extend partially circumferentially around the distal portion 712 of the shaft 702 to provide a plurality of flexion joints to facilitate bending.

Input port 704 may be provided with a Luer lock connector although a wide variety of other connector configurations, e.g., hose barb or slip fit connectors can also be used. Lumen 705 of input port 704 is fluidly connected to central lumen 720 of shaft 702 such that material can flow from a source, through input port 704 into central lumen 720 of the shaft 702 and out the open distal end or out of a side opening on distal portion 712. Input port 704 is preferably at least about 20 gauge and may be at least about 18, 16, 14, or 12 gauge or larger in diameter.

Input port 704 advantageously allows for releasable connection of the steerable and curvable injection device 700 to a source of hardenable media, such as a bone cement mixing device described herein. In some embodiments, a plurality of input ports 704, such as 2, 3, 4, or more ports are present, for example, for irrigation, aspiration, introduction of medication, hardenable media precursors, hardenable media components, catalysts or as a port for other tools, such as a light source, cautery, cutting tool, visualization devices, or the like. A first and second input port may be provided, for simultaneous introduction of first and second bone cement components such as from a dual chamber syringe or other dispenser. A mixing chamber may be provided within the injection device 700, such as within the proximal handle, or within the tubular shaft 702

A variety of adjustment controls 706 may be used with the steerable and curvable injection system, for actuating the curvature of the distal portion 712 of the shaft 702. Preferably, the adjustment control 706 advantageously allows for one-handed operation by a physician. In one embodiment, the adjustment control 706 is a rotatable member, such as a thumb wheel or dial. The dial can be operably connected to a proximal end of an axially movable actuator such as pull wire 724. See FIG. 7 A. When the dial is rotated in a first direction, a proximally directed tension force is exerted on the pull wire 724, actively changing the curvature of the distal portion 712 of the shaft 702 as desired. The degree of deflection can be observed fluoroscopically, and/or by printed or other indicia associated with the control 706. Alternative controls include rotatable knobs, slider switches, compression grips, triggers such as on a gun grip handle, or other depending upon the desired functionality.

In some embodiments, the adjustment control 706 allows for continuous adjustment of the curvature of the distal portion 712 of shaft 702 throughout a working range. In other embodiments, the adjustment control is configured for discontinuous (i.e., stepwise) adjustment, e.g., via a ratcheting mechanism, preset slots, deflecting stops, a rack and pinion system with stops, ratcheting band (adjustable zip-tie), adjustable cam, or a rotating dial of spring loaded stops. In still other embodiments, the adjustment control 706 may include an automated mechanism, such as a motor, hydraulic or compressed air system to facilitate adjustment.

The adjustment control may be configured to allow deflection of the distal portion 712 through a range of angular deviations from 0 degrees (i.e., linear) to at least about 15°, and often at least about 25°, 35°, 60°, 90°, 120°, 150°, or more degrees from linear.

In some embodiments, the length X of the flexible distal portion 712 of shaft 702 is at least about 10%, in some embodiments at least about 15%, 25%, 35%, 45%, or more of the length Y of the entire shaft 702 for optimal delivery of bone cement into a vertebral body. One of ordinary skill in the art will recognize that the ratio of lengths X:Y can vary depending on desired clinical application. In some embodiments, the maximum working length of needle 702 is no more than about 15", 10", 8", 7", 6", or less depending upon the target and access pathway. In one embodiment, when the working length of needle 702 is no more than about 8", the adjustable distal portion 712 of shaft has a length of at least about 1" and preferably at least about 1.5" or 2".

FIGS. 7 A-B are schematic perspective views of a distal portion of shaft 702 of a steerable and curvable vertebroplasty injector, according to one embodiment of the invention. Shown is the preferably rigid proximal portion 710 and deflectable distal portion 712. The distal portion 712 of shaft 702 includes a plurality of transverse slots 718 that extend partially circumferentially around the distal portion 712 of the shaft 702, leaving a relatively axially non-compressible spine 719 in the form of the unslotted portion of the tubular wall.

In some embodiments, the slots 718 can be machined or laser cut out of the tube stock that becomes shaft 702, and each slot may have a linear, chevron or other shape. In other embodiments, the distal portion 712 of shaft 702 may be created from an elongate coil rather than a continuous tube.

Slots 718 provide small compression hinge joints to assist in the reversible deflection of distal portion 712 of shaft 702 between a relatively straightened configuration and one or more curved configurations. One of ordinary skill in the art will appreciate that adjusting the size, shape, and/or spacing of the slots 718 can impart various constraints on the radius of curvature and/or limits of deflection for a selected portion of the distal portion 712 of shaft 702. For example, the distal portion 712 of shaft 702 may be configured to assume a second, fully deflected shape with a relatively constant radius of curvature throughout its length. In other embodiments, the distal portion 712 may assume a progressive curve shape with a variable radius of curvature distally which may, for example, have a decreasing radius distally. In some embodiments, the distal portion may be laterally displaced through an arc having a radius of at least about 0.5", 0.75", 1.0", 1.25", or 1.5" minimum radius (fully deflected) to 00 (straight) to optimize delivery of bone cement within a vertebral body. Wall patterns and deflection systems for bendable slotted tubes are disclosed, for example, in U.S. Patent Publication No. 2005/0060030 A1 to Lashinski et al., the disclosure of which is incorporated in its entirety by reference herein.

Still referring to FIGS. 7A-B, a pull wire 724 resides within the lumen 720 of shaft 702. The distal end 722 of the pull wire 724 is preferably operably attached, such as by adhesive, welding, soldering, crimping or the like, to an inner side wall of the distal portion 712 of the shaft 702. Preferably, the attachment point will be approximately 180° offset from the center of the axially extending spine 719. Proximal portion of pull wire 724 is preferably operably attached to adjustment control 706. The adjustment control 706 may be configured to provide an axial pulling force in the proximal direction toward the proximal end of pull wire 724. This in turn exerts a proximal traction on the distal portion 712 of shaft 702 operably attached to distal end 722 of pull wire 724. The slotted side of the tubular body shortens under compression, while the spine side 719 retains its axial length causing the distal portion 712 of shaft 702 to assume a relatively curved or deflected configuration. In some embodiments, a plurality of pull wires, such as two, three, four, or more pull wires 724 may be present within the lumen 720 with distal points of attachment spaced axially apart to allow the distal portion 712 of shaft 702 to move through compound bending curves depending on the desired bending characteristic. Distal axial advance of the actuator will cause a deflection in an opposite direction, by increasing the width of the slots 718.

Figure 8:
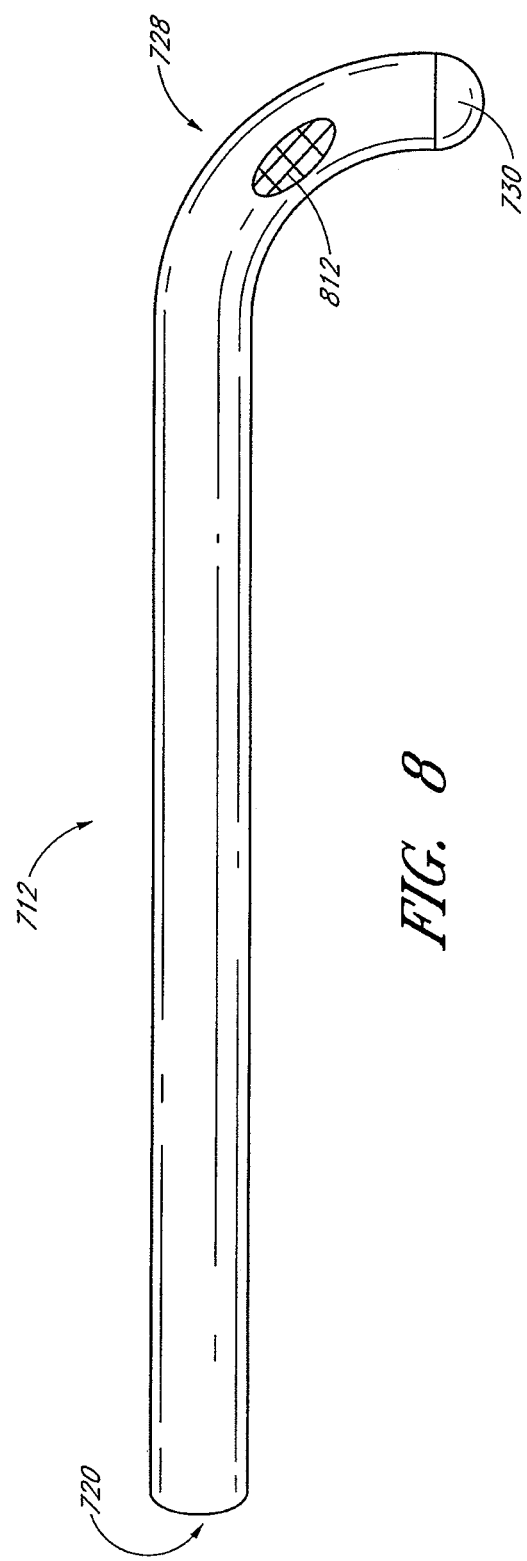
FIG. 8 is a schematic view of a distal portion of a steerable and curvable needle, having a side port.

A distal opening 728 is provided on shaft 702 in communication with central lumen 720 to permit expression of material, such as bone cement, from the injector 700. Some embodiments may include a filter such as mesh 812. Mesh structure 812 can advantageously control cement output by controlling air bubbles and/or preventing undesired large or unwieldy aggregations of bone cement from being released at one location and thus promote a more even distribution of bone cement within the vertebral body. The mesh 812 may be created by a laser-cut criss-crossing pattern within distal end as shown, or can alternatively be separately formed and adhered, welded, or soldered on to the distal opening 728. Referring to FIG. 8, the distal shaft portion 712 may also include an end cap 730 or other structure for occluding central lumen 720, and a distal opening 728 on the sidewall of shaft 702.

In some embodiments, the distal shaft 712 can generate a lateral force of at least about 0.125 pounds, 0.25 pounds, 0.5 pounds, 1 pound, 1.5 pounds, 2 pounds, 3 pounds, 4 pounds, 5 pounds, 6 pounds, 7 pounds, 8 pounds, 9 pounds, 10 pounds, or more by activating control 706. This can be advantageous to ensure that the distal portion 712 is sufficiently navigable laterally through cancellous bone to distribute cement to the desired locations. In some embodiments, the distal shaft 712 can generate a lateral force of at least about 0.125 pounds but no more than about 10 pounds; at least about 0.25 pounds but no more than about 7 pounds; or at least about 0.5 pounds but no more than about 5 pounds.

In some embodiments, the distal portion 712 of shaft 702 (or end cap 730) has visible indicia, such as, for example, a marker visible via one or more imaging techniques such as fluoroscopy, ultrasound, CT, or MRI.

Figure 9A:
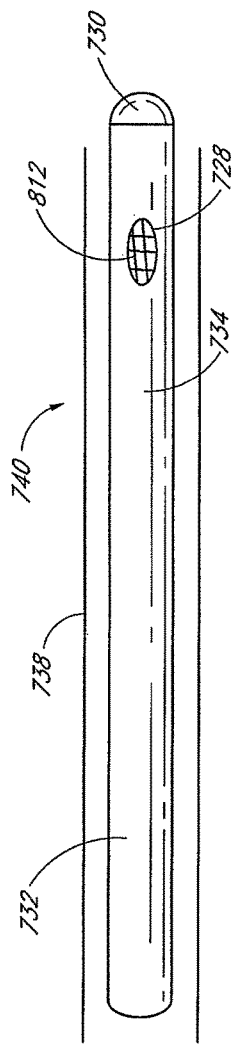
FIG. 9A is a schematic view of a distal portion of a steerable and curvable needle, positioned within an outer sheath.
Figure 9B:
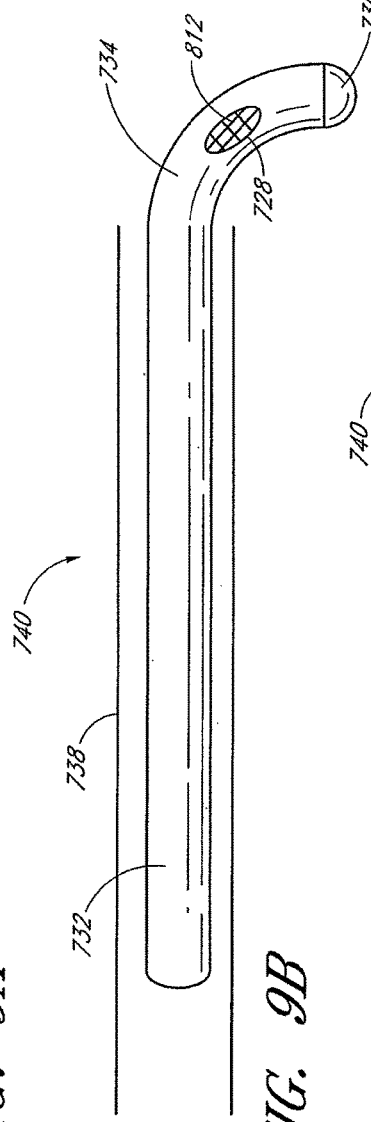
FIG. 9B is an illustration as in FIG. 9A, with the distal sheath partially proximally retracted.
Figure 9C:
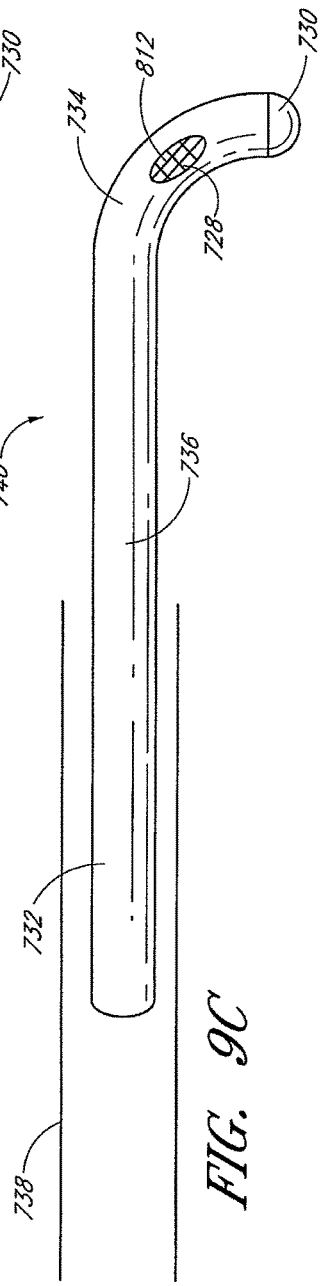
FIG. 9C is an illustration as in FIG. 9B, with the outer sheath proximally retracted a sufficient distance to fully expose the deflection zone.

FIGS. 9A-C illustrate in schematic cross-section another embodiment of a distal portion 734 of a steerable and curvable injection device 740. The tubular shaft 736 can include a distal portion 734 made of or containing, for example, a shape memory material that is biased into an arc when in an unconstrained configuration. Some materials that can be used for the distal curved portion 734 include Nitinol, Elgiloy, stainless steel, or a shape memory polymer. A proximal portion 732 of the shaft 736 is preferably relatively straight as shown. Also shown is end cap 730, distal lateral opening 728 and mesh 812.

The distal curved portion 734 may be configured to be axially movably received within an outer tubular sheath 738. The sheath 738 is preferably configured to have sufficient rigidity and radial strength to maintain the curved distal portion 734 of shaft 732 in a relatively straightened configuration while the outer tubular sheath 738 coaxially covers the curved distal portion 734. Sheath 738 can be made of, for example, a metal such as stainless steel or various polymers known in the catheter arts. Axial proximal withdrawal of the sheath 738 with respect to tubular shaft 736 will expose an unconstrained portion of the shape memory distal end 734 which will revert to its unstressed arcuate configuration. Retraction of the sheath 738 may be accomplished by manual retraction by an operator at the proximal end, retraction of a pull wire attached to a distal portion of the sheath 738, or other ways as known in the art. The straightening function of the outer sheath 738 may alternatively be accomplished using an internal stiffening wire, which is axially movably positioned within a lumen extending through the tubular shaft 736. The length, specific curvature, and other details of the distal end may be as described elsewhere herein.

Figure 10A:
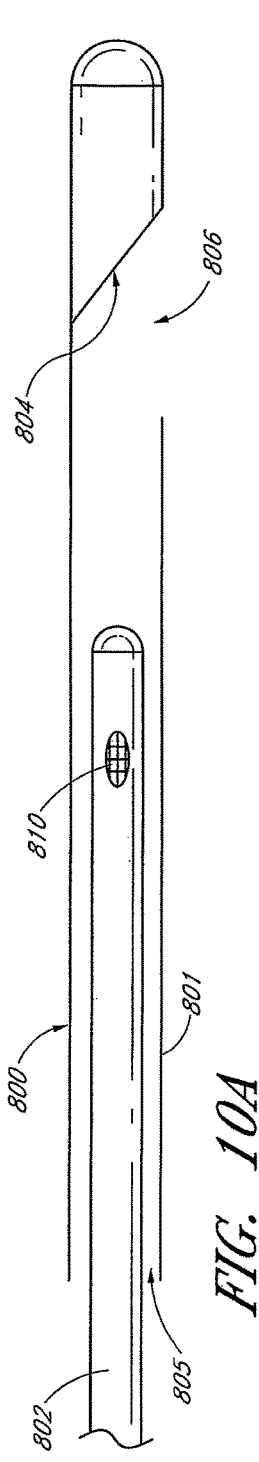
FIGS. 10A-10C illustrate various aspects of an alternative deflectable needle in accordance with the present invention.
Figure 10B:
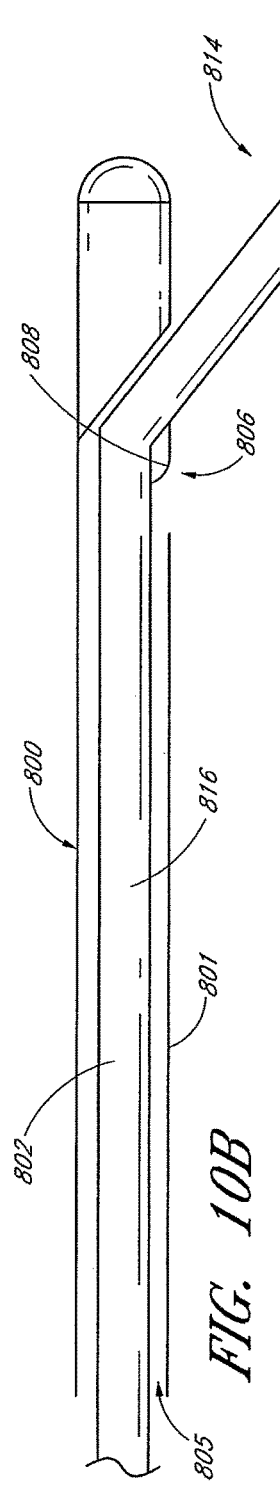
Figure 10C:
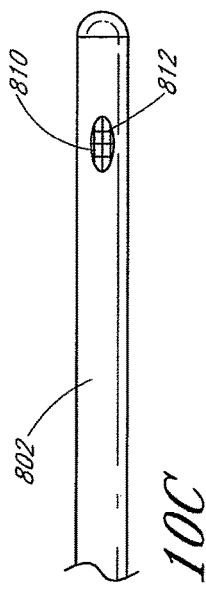

In another embodiment, as shown in FIGS. 10A-C, tubular shaft 802 of a steerable and curvable vertebroplasty injector may be generally substantially straight throughout its length in its unstressed state, or have a laterally biased distal end. A distally facing or side facing opening 810 is provided for the release of a material, such as bone cement. In this embodiment, introducer 800 includes an elongate tubular body 801 with a lumen 805 therethrough configured to receive the tubular shaft (also referred to as a needle) 802. Introducer 800 can be made of any appropriate material, such as, stainless steel and others disclosed elsewhere herein. Needle 802 may be made of a shape memory material, such as Nitinol, with superelastic properties, and has an outside diameter within the range of between about 1 to about 3 mm, about 1.5-2.5 mm, or about 2.1 mm in some embodiments.

Introducer 800 includes a needle-redirecting element 804 such as an inclined surface near its distal end. Needle-redirecting element 804 can be, for example, a laser-cut tang or a plug having a proximal surface configured such that when needle 802 is advanced distally into introducer 800 and comes in contact with the needle-redirecting element 804, a distal portion 814 of needle 802 is redirected out an exit port 806 of introducer 800 at an angle 808, while proximal portion 816 of needle 802 remains in a relatively straightened configuration, as shown in FIG. 10B. Bone cement can then be ejected from distal opening 810 on the end or side of needle 802 within bone 1000. Distal opening 810 may be present at the distal tip of the needle 802 (coaxial with the long axis of the needle 802) or alternatively located on a distal radial wall of needle 802 as shown in FIG. 10C. In some embodiments, the angle 808 is at least about 15 degrees and may be at least about 30, 45, 60, 90, 105 degrees or more with respect to the long axis of the introducer 800.

The illustrated embodiment of FIGS. 10A-C and other embodiments disclosed herein are steerable and curvable through multiple degrees of freedom to distribute bone cement to any area within a vertebral body. For example, the introducer 800 and needle 802 can both rotate about their longitudinal axes with respect to each other, and needle 802 can move coaxially with respect to the introducer 800, allowing an operator to actuate the injection system three dimensionally. The distal portion 814 of needle 802 can be deflected to a position that is angularly displaced from the long axis of proximal portion 816 of needle without requiring a discrete curved distal needle portion as shown in other embodiments herein.

Figure 11A:
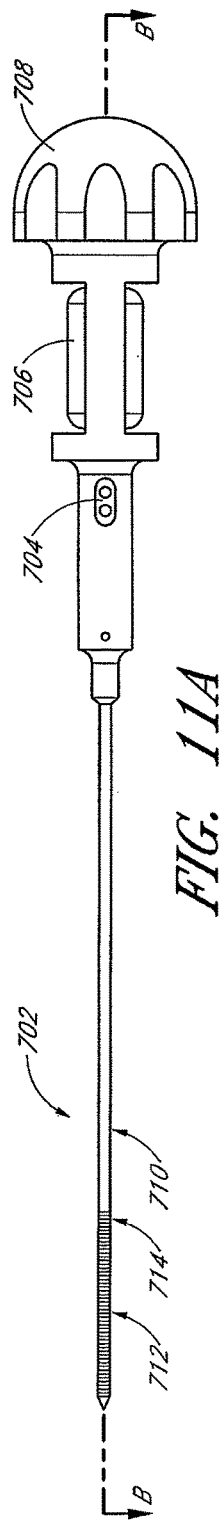
FIGS. 11A through 11C illustrate various aspects of a further deflectable needle design in accordance with the present invention.
Figure 11B:
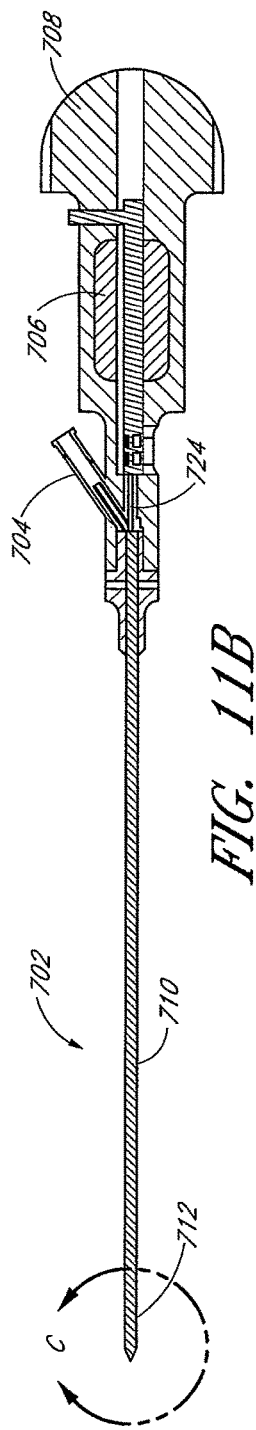
Figure 11C:
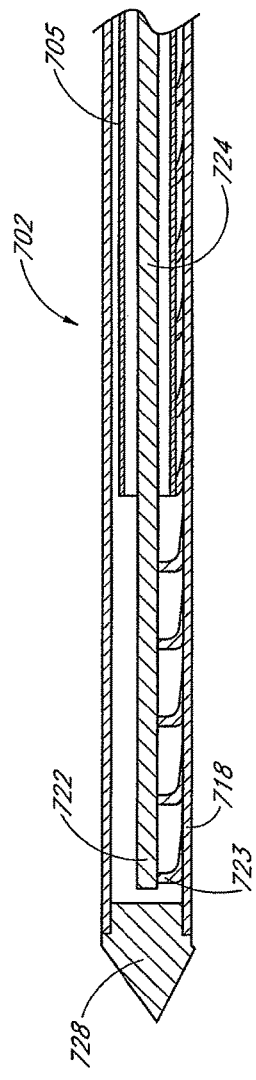

FIGS. 11A-C illustrate another embodiment of a steerable and curvable vertebroplasty injector. FIG. 11A schematically shows handle portion 708, adjustment control 706, and elongate needle shaft 702, including proximal portion 710, distal portion 712, and transition point 714. FIG. 11B is a vertical cross-section through line A-A of FIG. 11A, and shows adjustment control 706 operably connected to pull wire 724 such as through a threaded engagement. Also shown is input port 704, and proximal portion 710 and distal portion 712 of needle shaft 702. FIG. 11C illustrates a cross-sectional view of distal portion 712 of shaft 702. The distal end 722 of pull wire 724 is attached at an attachment point 723 to the distal portion 712 of shaft 702. Proximal retraction on pullwire 724 will collapse transverse slots 718 and deflect the injector as has been discussed. Also shown is an inner tubular sleeve 709, which can be advantageous to facilitate negotiation of objects or media such as bone cement, through the central lumen of the needle shaft 702.

The interior sleeve 709 is preferably in the form of a continuous, tubular flexible material, such as nylon or polyethylene. In an embodiment in which the needle 702 has an outside diameter of 0.095 inches (0.093 inch coil with a 0.001 inch thick outer sleeve) and an inside diameter of 0.077 inches, the interior tubular sleeve 709 may have an exterior diameter in the area of about 0.074 inches and an interior diameter in the area of about 0.069 inches. The use of this thin walled tube 705 on the inside of the needle shaft 702 is particularly useful for guiding a fiber through the needle shaft 702. The interior tube 705 described above is additionally preferably fluid-tight, and can be used to either protect the implements transmitted therethrough from moisture, or can be used to transmit bone cement through the steerable and curvable needle.

In some embodiments, an outer tubular coating or sleeve (not shown) is provided for surrounding the steerable and curvable needle shaft at least partially throughout the distal end of the needle. The outer tubular sleeve may be provided in accordance with techniques known in the art and, in one embodiment, is a thin wall polyester (e.g., ABS) heat shrinks tubing such as that available from Advanced Polymers, Inc. in Salem, N.H. Such heat shrink tubing have a wall thickness of as little as about 0.0002 inches and tube diameter as little as about 0.010 inches. The outer tubular sleeve enhances the structural integrity of the needle, and also provides a fluid seal and improved lubricity at the distal end over embodiments with distal joints 718. Furthermore, the outer tubular sleeve tends to prevent the device from collapsing under a proximal force on a pull wire. The sleeve also improves lubricity of the tubular members, and improves torque transmission.

In other embodiments, instead of a slotted tube, the needle shaft of a vertebroplasty injection system may include a metal or polymeric coil. Steerable and curvable helical coil-type devices are described, for example, in U.S. Pat. No. 5,378,234 or 5,480,382 to Hammerslag et al., which are both incorporated by reference herein in their entirety.

An interior tubular sleeve (not illustrated) may be provided to facilitate flow of media through the central lumen as described elsewhere in the application. In some embodiments, a heat-shrunk outer tubular sleeve as described elsewhere in the application is also provided to enhance the structural integrity of the sheath, provide a fluid seal across the chevrons or slots, as well as improve lubricity.

The steerable and curvable injection needle (also referred to as the injection shaft) may have an outside diameter of between about 8 to 24 gauge, more preferably between about 10 to 18 gauge, e.g., 12 gauge, 13 gauge (0.095" or 2.41 mm), 14 gauge, 15 gauge, or 16 gauge. In some embodiments, the inside diameter (luminal diameter) of the injection needle is between about 9 to 26 gauge, more preferably between about 11 to 19 gauge, e.g., 13 gauge, 14 gauge, 15 gauge, 16 gauge, or 17 gauge. In some embodiments, the inside diameter of the injection needle is no more than about 4 gauge, 3 gauge, 2 gauge, or 1 gauge smaller than the outside diameter of the injection needle.

The inside luminal diameter of all of the embodiments disclosed herein is preferably optimized to allow a minimal exterior delivery profile while maximizing the amount of bone cement that can be carried by the needle. In one embodiment, the outside diameter of the injection needle is 13 gauge (0.095" or 2.41 mm) with a 0.077" (1.96 mm) lumen. In some embodiments, the percentage of the inside diameter with respect to the outside diameter of the injection needle is at least about 60%, 65%, 70%, 75%, 80%, 85%, or more.

Referring to FIGS. 12 and 13, there is illustrated a modification of the steerable and curvable injection needle 10, in accordance with the present invention. The injection needle 10 comprises an elongate tubular shaft 702, extending between a proximal portion 710 and a distal portion 712. The proximal portion 710 is carried by a proximal handle 708, which includes a deflection controller 706 such as a rotatable knob or wheel. Rotation of the control 706 causes a lateral deflection or curvature of the distal steering region 24 as has been discussed.

Input port 704 is in fluid communication with a distal opening 728 on a distal tip 730, by way of an elongate central lumen 720. Input port 704 may be provided with any of a variety of releasable connectors, such as a Luer or other threaded or mechanically interlocking connector known in the art. Bone cement or other media advanced through lumen 720 under pressure may be prevented from escaping through the plurality of slots 718 in the steering region 24 by the provision of a thin flexible tubular membrane carried either by the outside of tubular shaft 702, or on the interior surface defining central lumen 720.

Figures 14, 15:
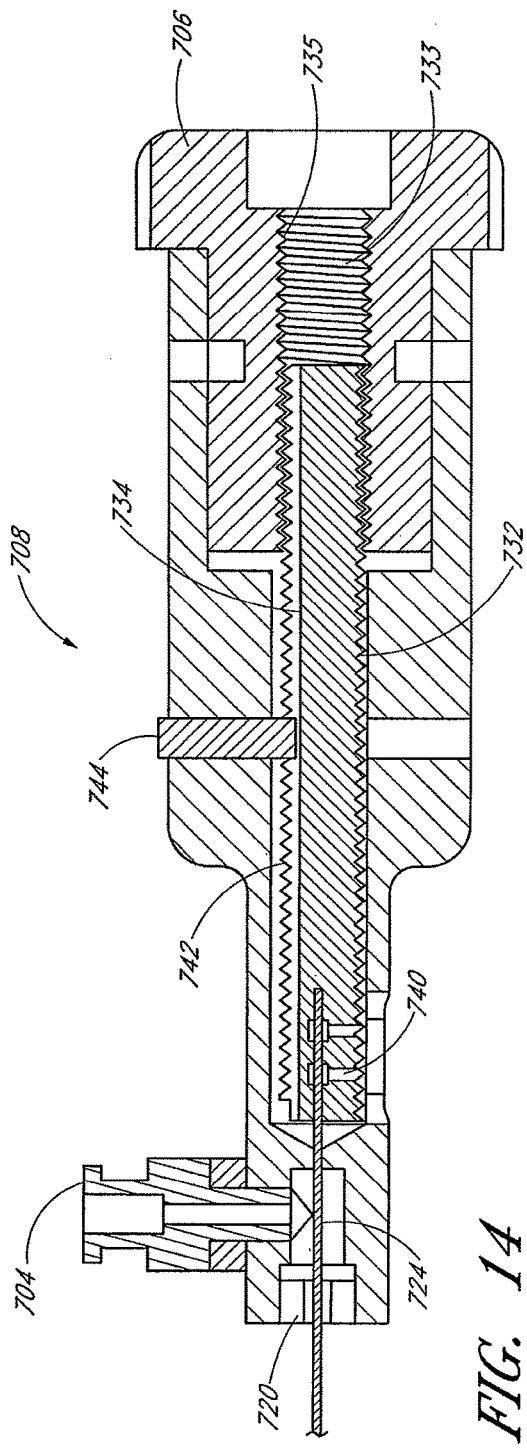
FIG. 14 is a side elevational cross section through the proximal handle of the deflectable needle illustrated in FIG. 13.
FIG. 15 is a cross sectional detail view of the distal tip of the steerable and curvable needle illustrated in FIG. 13.

Referring to FIG. 14, the handle 708 is provided with an axially oriented central bore 732 having a first, female thread 733 thereon. A slider 734 having a second complementary male thread 735, is thread-engaged with the central bore 732. Rotation of the knob 706 relatively to the slider 734 thus causes the slider 734 to distally advance or proximally retract in an axial direction with respect to the handle 708. The slider 734 is mechanically linked to the pull wire 724, such as by the use of one or more set screws or other fastener 740.

Slider 734 is provided with at least one axially extending keyway or spline 742 for engaging a slide dowel pin 744 linked to the handle 708. This allows rotation of the rotatable control 706, yet prevents rotation of the slider 734 while permitting axial reciprocal movement of the slider 734 as will be apparent to those of skill in the art. One or more actuating knob dowel pins 746 permits rotation of the rotatable control 706 with respect to the handle 708 but prevents axial movement of the rotatable control 706 with respect to the handle 708.

Referring to FIG. 15, the distal end of the shaft 702 may be provided with any of a variety of distal opening 728 orientations or distal tip 730 designs, depending upon the desired functionality. In the illustrated embodiment, the distal tip 730 is provided with an annular flange 748 which may be slip fit into the distal end of the tubular body 702, to facilitate attachment. The attachment of the distal tip 730 may be further secured by welding, crimping, adhesives, or other bonding technique.

In general, the distal tip 730 includes a proximal opening 750 for receiving media from the central lumen 720, and advancing media through distal opening 728. Distal opening 728 may be provided on a distally facing surface, on a laterally facing surface, or on an inclined surface of the distal tip 730.

Referring to FIGS. 15A and 15B, there is illustrated a distal tip 30 having a single inclined opening 728 thereon. In any of the designs disclosed herein, one or two or three or four or more distal ports 728 may be provided, depending upon the desired clinical performance. In the illustrated embodiment, the distal tip includes a rounded distal end 750 which transitions either smoothly or through an angular interface with an inclined portion 752. The distal opening 728 is positioned distally of a transition 754 at the proximal limit of the inclined surface 752. This configuration enables the distal opening 728 to have a distal axially facing component, as compared to an embodiment having a side wall opening. See, for example, FIG. 8.

Referring to FIG. 15B, the tip 730 can be considered to have a central longitudinal axis 770. The aperture 728 may be considered as residing on an aperture plane 772, which intersects the distal most limit and the proximal most limit of the aperture 728. Aperture plane 772 intersects the longitudinal axis at an angle, θ. In an embodiment having a side wall aperture, the aperture plane 772 and longitudinal axis 770 would be parallel. In an embodiment having a completely distally facing aperture, the aperture plane 772 would intersect the longitudinal axis 770 at an angle of 90°.

In the illustrated embodiment, the inclined aperture 728 is defined by an aperture plane 772 intersecting the longitudinal axis 770 at an angle θ, which is at least about 5°, often at least about 15°, and in many embodiments, at least about 25° or more. Intersection angles within the range of from about 15° to about 45° may often be used, depending upon the desired clinical performance.

Figure 15D:
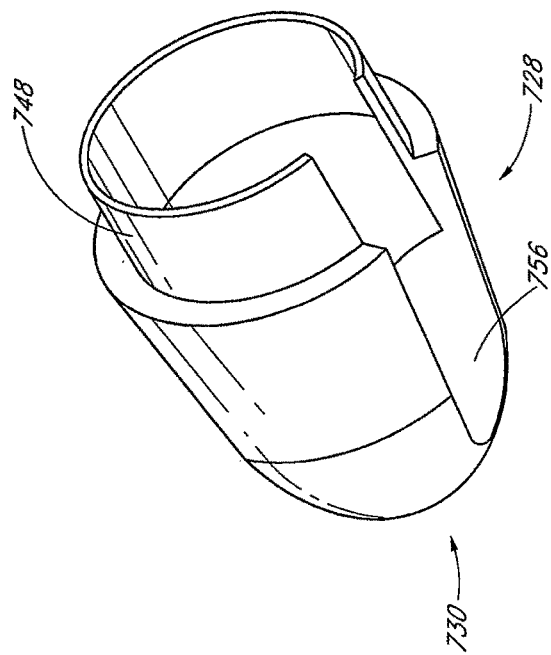
FIGS. 15A through 15X illustrate various views of alternative distal tip designs.
FIG. 15Y illustrates schematically an injector with an anti-coring and clog-preventing obturator within the central lumen of the injector.
Figure 15C:
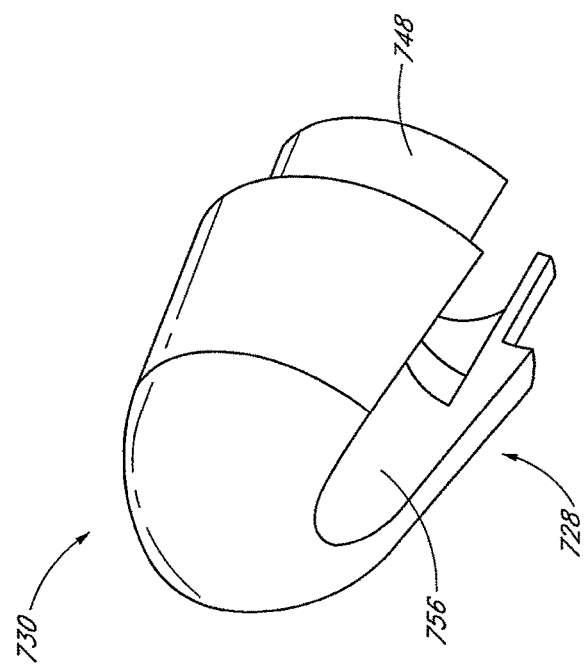

Referring to FIGS. 15C and 15D, an alternate distal tip 730 is illustrated. In this configuration, the distal opening 728 is in the form of a sculpted recess 756 extending axially in alignment with at least a portion of the central lumen 720. Sculpted recess 756 may be formed in any of a variety of ways, such as by molding, or by drilling an axial bore in an axial direction with respect to the tip 730. The sculpted recess 756 cooperates with the tubular body 702, as mounted, to provide a distal opening 728 having an inclined aspect as well as an axially distally facing aspect with respect to the longitudinal axis of the steerable and curvable needle.

Figure 15F:
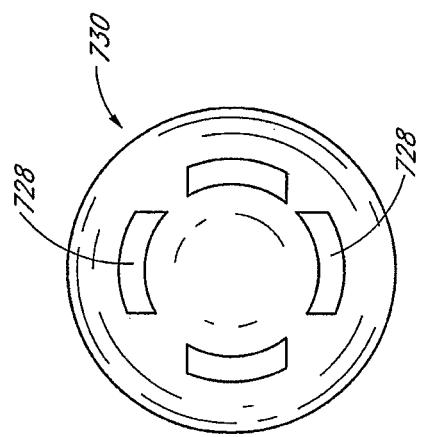
Figure 15E:
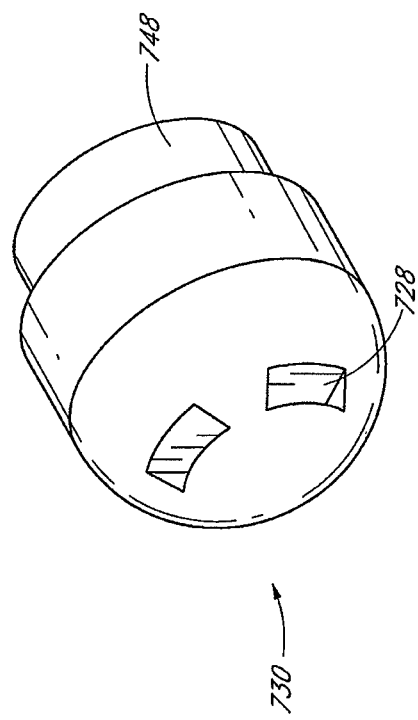

Referring to FIGS. 15E and 15F, there is illustrated a distal tip 730 having a plurality of distally facing apertures 728. In the illustrated embodiment, four distal apertures are provided. The distal apertures 728 may be provided on the rounded distal end 750, or on an inclined surface 752 as has been discussed.

Referring to FIGS. 15G and 15H, there is illustrated an alternative distal tip 730. In this configuration, an opening 728 is oriented in a distally facing direction with respect to the longitudinal axis of the needle. The distal opening of the central lumen is covered by at least one, preferably two, and, as illustrated, four leaflets 758 to provide a collet-like configuration. Each of the adjacent leaflets 758 is separated by a slot 760 and is provided with a living hinge or other flexible zone 762.

In use, the distal tip 730 may be distally advanced through soft tissue or cancellous bone, with the distal opening 728 being maintained in a closed orientation. Following appropriate positioning of the distal tip 30, the introduction of bone cement or other media under pressure through the central lumen 720 forces the distal opening 728 open by radially outwardly inclining each leaflet 758 about its flexion point 762. This configuration enables introduction of the needle without "coring" or occluding with bone or other tissue, while still permitting injection of bone cement or other media in a distal direction.

Figure 15I:
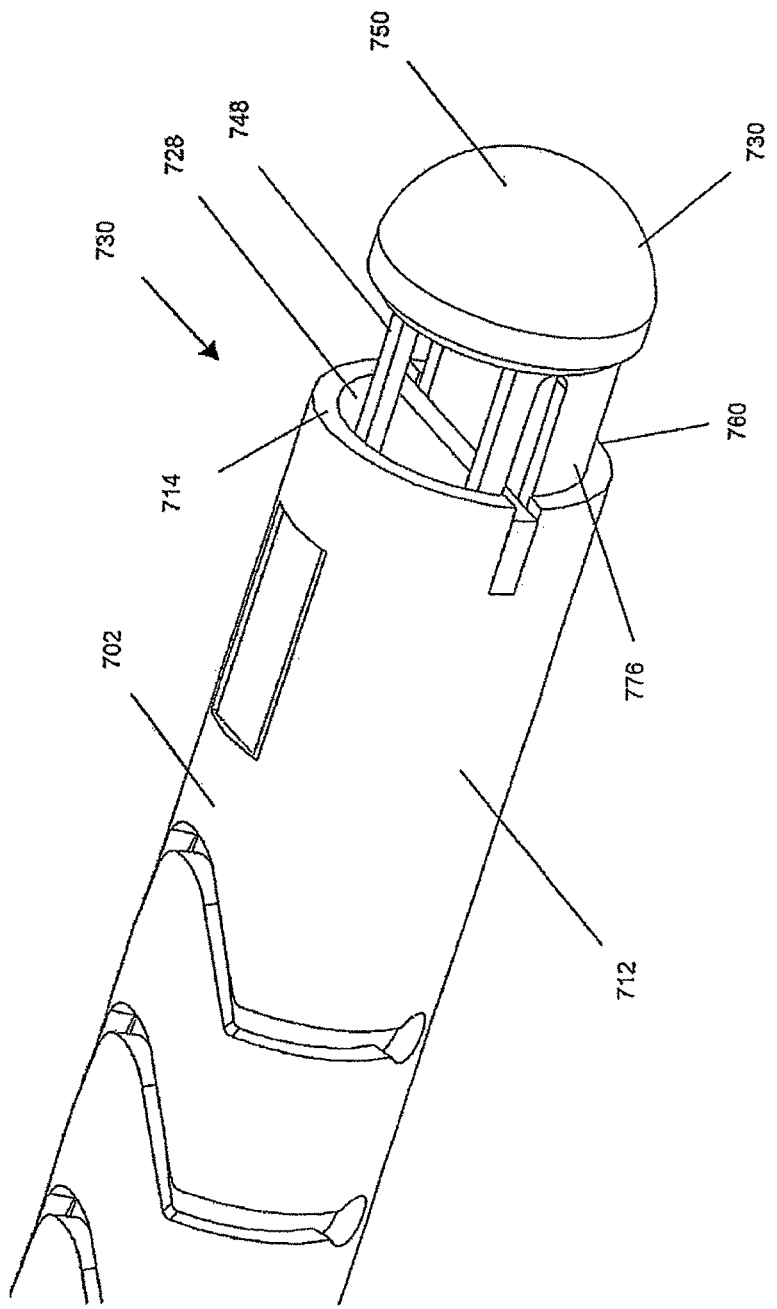

Referring to FIG. 15I, there is illustrated yet another distal tip, this time comprising a "pop-up" or deployable cap 730 in its deployed state. The injection needle 10 includes a shaft 702 having a distal shaft end 714. Any of the foregoing or other tip configurations may be separately formed and secured to the distal end of the tubular body 702, or may be machined, molded or otherwise formed integrally with the tube 702. Distal aperture 728 can be occluded by a plug or cap 730 with, preferably, an atraumatic tip, which minimizes coring during distal advance of the injection needle. The cap 730 includes a flange 748 and cap extensions 776 having optional slots 760. In its undeployed state, the cap flange 748 is slip fitted within the needle injector shaft 702 and retained only by friction or by a reversible bond to the distal end 714 of the shaft, which is sufficient to retain the cap 730 in the distal end 714 during injection, but insufficient to resist the force of injected bone cement in some embodiments. In its undeployed state, the cap extensions 776 are not exposed and covered by the injection needle shaft 702. The deployable cap 730 can be popped-up or deployed distally from the distal end 714 of the shaft under pressure, thereby exposing the distal aperture 728 for cement release.

The deployable cap 730 may take any of a variety of forms depending upon the injector design. The deployable cap 730 may be made from any of a variety of materials, such as stainless steel, Nitinol, or other implantable metals; any of a wide variety of implantable polymers such as PEEK, nylon, PTFE; or of bone cement such as PMMA. Alternatively, any of a variety of bioabsorbable polymers may be utilized to form the deployable cap 730, including blends and polymers in the PLA-PGLA absorbable polymer families.

In operation, once the injection needle 10 is positioned in a desired location, the distal cap 730 may be pushed or popped-open from the distal end of the injector, such as by applying pressure from the injected bone cement. For example, the injected bone cement can apply a fluidic pressure that forces the deployable cap 730 to pop-open distally to its deployed state, as shown in FIG. 15I. In some embodiments, the cap can have at least two, three, or more successively longer distal deployment positions, thereby adjusting the size of the distal aperture 728 for variable control on the flow of media through distal aperture 728. In some embodiments, the minimum amount of pressure required to pop-open the deployable cap 730 can be set at a certain pressure threshold. Once the deployable cap 730 is popped-open and placed in its deployed state, the aperture 728 is exposed and bone cement can be released and injected into a target location. The bone cement can flow out of the injection needle 10, past the distal aperture 728, and through any of the slots 760 or open regions of the deployable cap 730. In some embodiments, the deployable cap 730 is configured to be retractable back to its undeployed state, such as via a pullwire or other actuating mechanism, thereby reducing or inhibiting the flow of bone cement and advantageously reducing the risk of overflow and clogging of the injection needle.

Figure 15J:
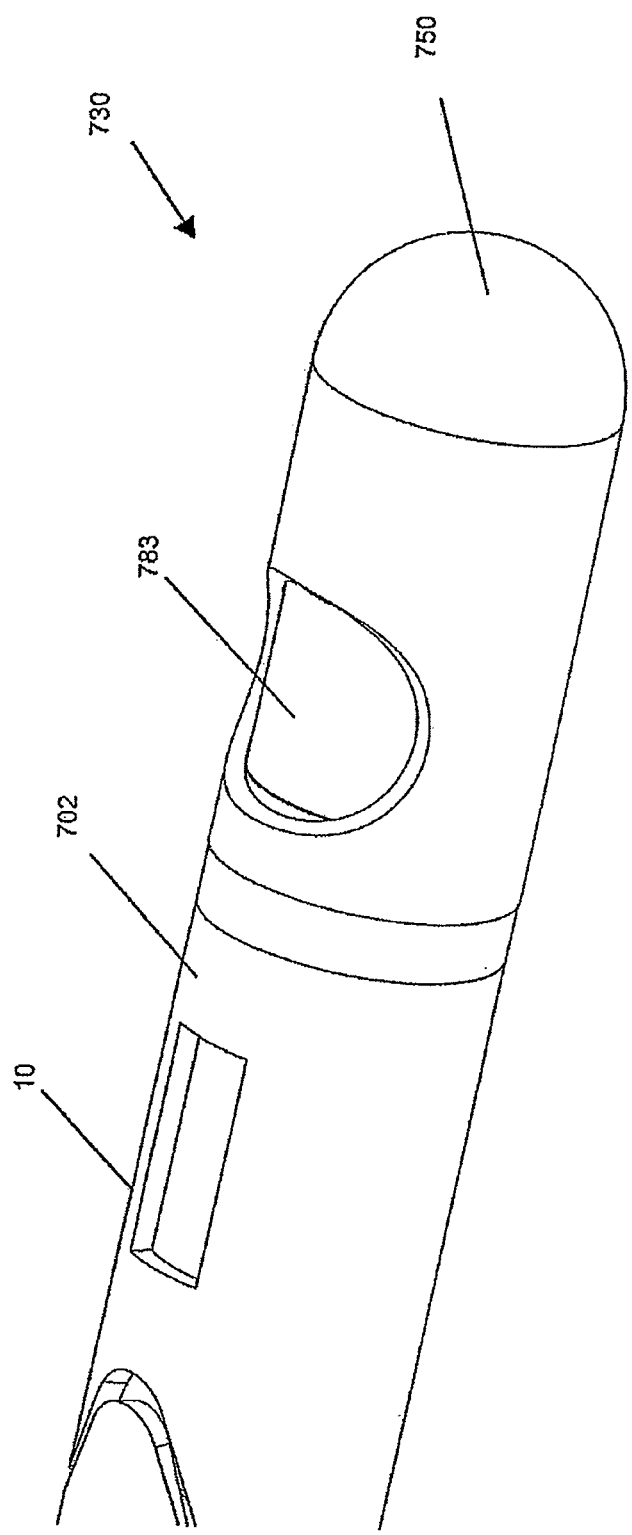
Figure 15K:
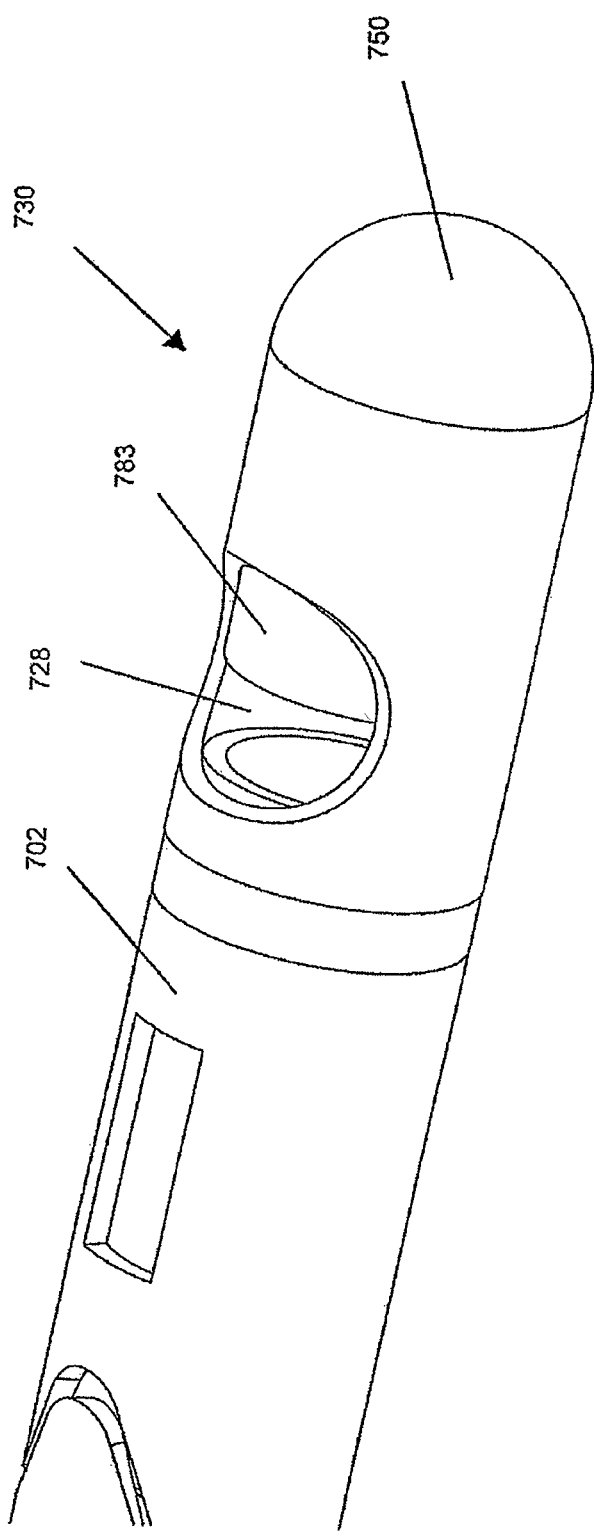

Referring to FIG. 15J, there is illustrated yet another distal tip, this time including a check valve 783 that can block the release of bone cement from a sidewall aperture 728 of an injection needle 10. The distal tip 730 includes a blunt rounded distal end 750 and a check valve 783 coupled to an interior surface of the injection needle 10. The check valve 783 is capable of covering one or more apertures formed on the injection needle, such as on its rounded distal end or sidewalls (as shown in FIGS. 15J and 15K), that exposes the interior of the shaft 702. In some embodiments, the check valve 783 is moveable or capable of gliding along a longitudinal axis of the shaft 702. With the gliding check valve 783, the distal tip 730 can assume three different states: a blocked state (not shown), in which the check valve 783 completely covers the aperture 728; a partially blocked state (shown in FIGS. 15J and 15K), in which the check valve 783 partially covers the aperture 728; and an unblocked state (not shown), in which the aperture 728 is completely exposed.

In its blocked state, the distal tip 730 includes a check valve 783 that serves as a plug to completely cover the aperture 728 such that no bone cement will flow through the aperture 728. The check valve 783 can be moved to expose the aperture 728, in whole or in part, by using a mechanical or electrical mechanism. In some embodiments, the check valve 783 can be moved to expose the aperture 728 by using fluidic pressure, e.g., from flowing bone cement, that forces the check valve 783 to slide along the longitudinal direction of the injection needle 10, thereby exposing the sidewall aperture 728. In some embodiments, a lock or mechanical stopper can be provided that limits the movement of the check valve 783, such that the size of the exposed aperture 728 can be controlled. For example, the mechanical stopper can lock the check valve 783 in place once approximately half of the aperture 728 is exposed, thereby restricting the amount of bone cement that can be released from the injection needle 10. The check valve 783 advantageously allows for greater control over the injected volume and flow rate of the bone cement material, thereby reducing the risk of overflow and clogging of the injection needle.

Figure 15L:
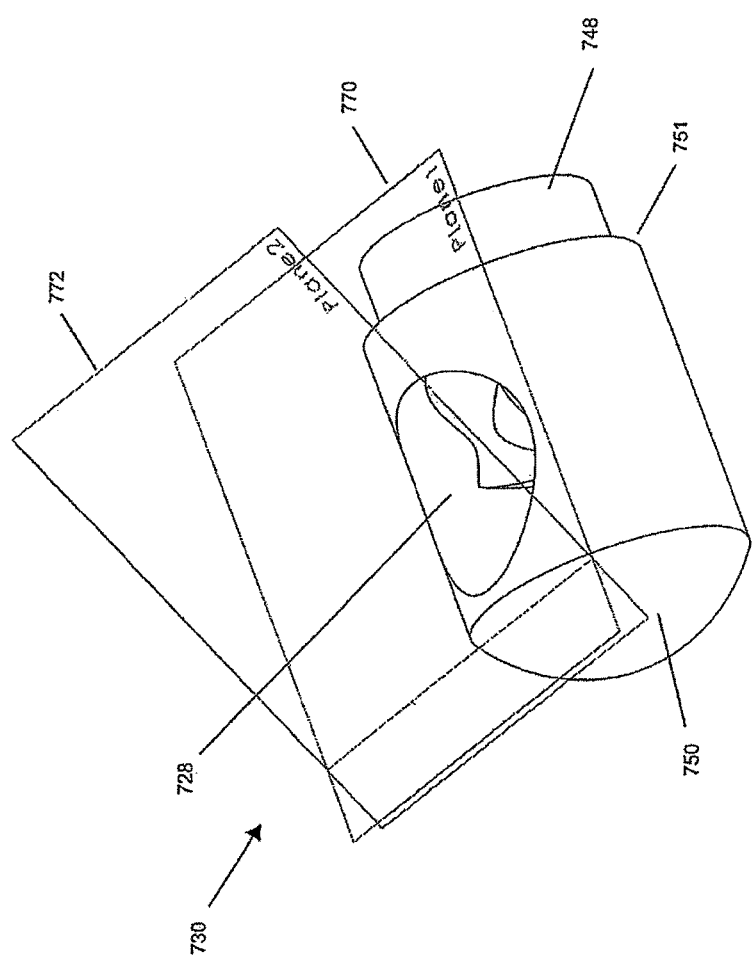
Figure 150:
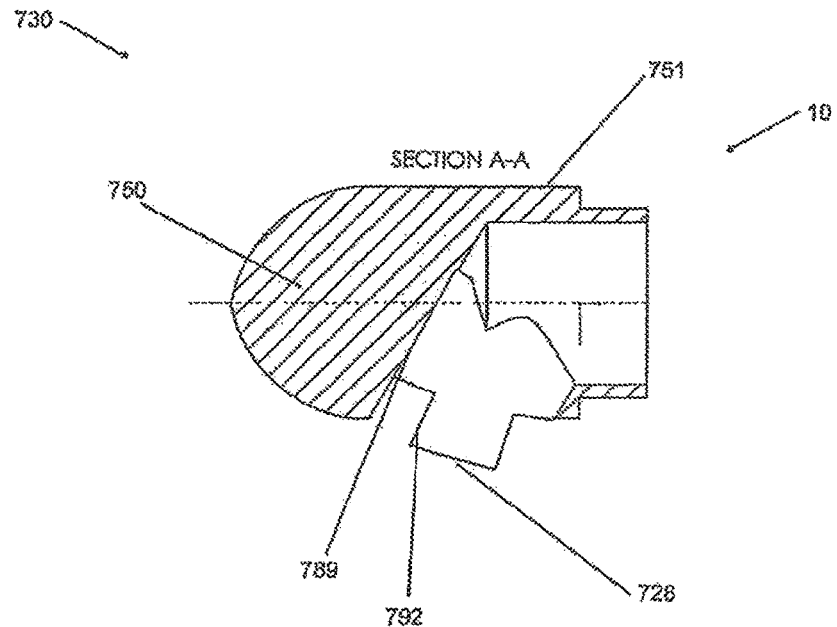

Referring to FIG. 15L, there is illustrated yet another distal tip, this time comprising a single inclined aperture 728 serving as an exit port along the sidewall 751 of the distal tip 730. Unlike the distal tip in FIGS. 15A and 15B that includes a single inclined aperture that resides on the rounded distal end 750, the distal tip in FIG. 15L includes a single inclined aperture that resides on the sidewall 751. The single inclined aperture 728 may be considered as residing on an aperture plane 772, which intersects a plane along the longitudinal axis 770. While in some embodiments, the aperture plane 772 is viewed as being parallel to the plane along the longitudinal axis 770, in other embodiments, the aperture plane 772 is at an angle that is at least about 5°, often at least about 15°, and in many embodiments, at least about 25° or more. Intersection angles within the range of from about 15° to about 45° may often be used, depending upon the desired clinical performance.

As the aperture 728 resides in a plane 772 that is at a non-parallel angle to the plane 770 along the longitudinal axis of the distal tip 730, the aperture 728 is also angulated with respect to the surface of the distal tip 730. Angled surfaces 789 (best shown in FIGS. 15M and 15N) reside adjacent to the aperture 728. FIG. 15M1 is a cross-section across line A-A of FIG. 15M. The angled surfaces 789 provide a sloped passage upon which bone cement from the injection needle 10 can pass through. Providing angled surfaces 789 on the sidewall of the distal tip 730 from which bone cement is injected allows for greater control of the bone cement relative to conventional injection needles, as the angled surfaces assist in breaking the flow of the bone cement exiting from the injection needle 10, thereby reducing the risk of overflow. The advantage of this design is that the aperture yields a smooth transition, which allows better outflow of the cement against cancellous bone fragments, blood and bone marrow that may have become lodged in the aperture. While the angled surfaces 789 appear planar, as shown in FIG. 15N, in some embodiments, the surfaces may be non-planar e.g., it may include ridges, to assist in controlling the flow rate of the bone cement from the injection needle to a target site.

Referring to FIG. 15O, there is illustrated a distal tip similar to the distal tip in FIG. 15N having a single inclined aperture 728 residing adjacent to angled surfaces 789; however, the distal tip 730 in FIG. 15O includes a single inclined aperture 728 that is narrower than the aperture in FIG. 15N. While the aperture 728 is still formed in the sidewall of the distal tip 730, the aperture is formed from an angled surface 789 that is narrowed to a restricting neck 792 having a reduced width or diameter. In some embodiments, the width or diameter of the restricting neck 792 is at least about 5%, 10%, 15%, 20%, 25%, 30%, 35%, 40%, 45%, 50%, or more narrower than the width or diameter of the lumen of the distal end 730 proximal to the restricting neck 792. The restricting neck 792 helps to both control the flow rate of the bone cement out of the injection needle 10 and to reduce the volume of bone cement flowing into a target site, thereby reducing the likelihood of overflow and clogging.

Referring to FIGS. 15P-15P2, there is illustrated an aperture 728 having angled surfaces 789 that are located at right angles to the corresponding angled surfaces 789 shown in FIG. 15N, e.g., the aperture is inclined proximally and laterally. FIG. 15P1 is a cross-section through line C-C of FIG. 15P. FIG. 15P2 is a perspective view of the tip 730 shown in FIG. 15P. This allows injectable material to be dispensed in a direction that is inward and proximal, as opposed to distal as in FIG. 15N. The merit of this positioning is to minimize clogging during the insertion of the steerable and curvable needle. In some embodiments, the angled surface 789 of the inclined aperture 728 forms an angle with the longitudinal axis of the tip 730 (as illustrated in FIG. 15B). In some embodiments, the angle can be between about 0 and 90 degrees, such as between about 15 and 75 degrees, between about 30 and 60 degrees, between about 15 and 45 degrees, between about 20 and 40 degrees, between about 45 and 75 degrees, or about 30 degrees or about 45 degrees. In some embodiments, the angled surface can have a distally facing component as illustrated in FIGS. 15M-N, or a proximally facing component as illustrated in FIGS. 15P-15P2. Where the aperture 728 is not on the distal tip 730 but more proximally on the distal end cap 750 as illustrated, the distal end of the aperture 728 can be, in some embodiments, separated by about 0.10, 0.09, 0.08, 0.07, 0.06, 0.05, 0.04, 0.03, 0.02 or less inches from the inclined distal tip 730 portion of the distal end cap 750. Any of the foregoing or other tip configurations may be separately formed and secured to the distal end of the tubular body 702, or may be machined, molded or otherwise formed integrally with the tube 702. In some embodiments, the aperture 728 can have a diameter of between about 0.060 and 0.010 inches, such as between about 0.070 and 0.090 inches, or between about 0.075 and 0.085 inches. In some embodiments, the distal end 730 can have an outside diameter (OD) of between about 0.05 and 0.20 inches, such as between about 0.10 and 0.12 inches, or between about 0.107 and 0.111 inches. In some embodiments, the distal end 730 can have an inside diameter (ID) for flow of cement media of between about 0.04 and 0.19 inches, such as between about 0.05 and 0.10 inches, or between about 0.072 and 0.078 inches in some embodiments. The length of the distal end cap 730 can be, in some embodiments, between about 0.10 and 0.50 inches, such as between about 0.10 inches and 0.30 inches, or between about 0.15 inches and 0.25 inches.

Referring to FIGS. 15Q-15Q2, there is illustrated one embodiment of a distal tip 730 having an aperture 728 with angled surfaces 789 that allow injectable material to be dispensed in a direction that is outward and distal. FIG. 15Q1 is a cross-sectional view through line A-A of FIG. 15Q. FIG. 15Q2 is a perspective view of the distal tip 730 of FIG. 15Q. The body of the distal tip 730 in FIG. 15Q is somewhat different from other distal tips disclosed herein. Whereas the distal tip 730 in some embodiments (e.g., FIG. 15P) include a generally cylindrical body with a section having a generally constant cross-sectional diameter that transitions into a dome-like distal end cap 750, in FIG. 15Q, the body of the distal tip 730 having a wall that has a first radially inwardly tapering surface 773 (going from the proximal to distal end of the distal tip) that transitions into a second radially outwardly tapering surface 774 that transitions into the distal end cap 750. In some embodiments, the length of the first radially inwardly tapering surface (starting from the proximal end to the distal end of the distal tip) is more than about 50%, 60%, 70%, 80%, 90%, or more of the second radially outwardly tapering surface. In other embodiments, the length of the first radially inwardly tapering surface 773 is less than about 50%, 40%, 30%, 20%, 10%, or less of the length of the second radially outwardly tapering surface 774. The radially inwardly tapering surface 773 could be proximal to (as illustrated in FIG. 15T), or distal to the radially outwardly tapering surface 774, or a distal tip could have two, three, or more radially inwardly tapering surface 773 and/or radially outwardly tapering surfaces 774 (e.g., in a sinusoidal pattern).

Referring to FIGS. 15R-15R2, there is illustrated a distal tip 730 having an aperture 728 with angled surfaces 789 that allow injectable material to be dispensed in a direction that has a proximally facing component. FIG. 1581 is a cross-sectional view through line A-A of FIG. 15R, while FIG. 15R2 is a perspective view. The body of the distal tip 730 in FIGS. 15R-15R2 has a wall having a generally transversely symmetrical, concave curvilinear surface 774 that transitions into the dome-like distal end cap 750.

Referring to FIG. 15S-15S2, there is illustrated a distal tip 730 having an aperture 728 with angled surfaces 789 that allow injectable material to be dispensed in a direction that has a proximally facing component. FIG. 15S1 is a cross-sectional view through line A-A of FIG. 15S, while FIG. 15S2 is a perspective view. The body of the distal tip 730 in FIG. 15S has a wall having a linear bow-tie shaped radially inwardly tapered zone 773 and a linear radially outwardly tapered zone 774 from a proximal to distal direction (in contrast to the more curved taper of the wall of FIG. 15R) before forming the dome-like distal end cap 750.

Referring to FIG. 15T, there is illustrated a distal tip 730 having an aperture 728 with angled surfaces 789 that allow injectable material to be dispensed in a direction that is inward and proximal. FIG. 15T1 is a cross-sectional view through line A-A of FIG. 15T, while FIG. 15T2 is a perspective view. The body of the distal tip 730 in FIG. 15T includes a wall having a proximal radially inwardly tapering zone 774 followed by a radially outwardly tapering zone 773 from a proximal to distal direction, which transitions into the dome-like distal end cap 750.

Referring to FIGS. 15U-15U2, there is illustrated a "double angle" distal tip 730 having an aperture 728 with opposing angled surfaces 789a and 789b (angled relative to an axis normal to the longitudinal axis of the distal tip) that define an outflow path, or exit port for dispensation of injectable material. FIG. 15U1 is a cross-sectional view through line A-A of FIG. 15U, while FIG. 15U2 is a perspective view. As illustrated, the angled surfaces 789a, 789b are configured such that the aperture 728 can become larger in an axial direction, circumferential direction, or both as the media flows out of the central lumen, through the exit port, and out of the device into the intended anatomical location. Other embodiments could include a plurality of apertures 728, such as 2, 3, 4, or more. In some embodiments, the exit port has a first inner axial or circumferential dimension at a junction with the central lumen and a second axial or circumferential dimension where bone cement exits the device, where the second dimension is greater than the first dimension, such as by at least about 5%, 10%, 15%, 20%, 25%, 50%, or more. The increase in axial or circumferential direction of the exit port from the junction with the central lumen to the location in which the bone cement exits the device can be in a linear fashion, follow an accelerated curve, or a decelerated curve in some embodiments. Also as illustrated, the outer wall of the distal tip 730 has a first portion 799 that has a sidewall that is generally parallel to the longitudinal axis of the injector when the injector is in a nondeflected configuration, followed by a second radially inwardly tapering portion 774 that is not generally parallel to the longitudinal axis of the injector when the injector is in a nondeflected configuration, and ending distally in the distal cap 750, which can be dome-shaped or another atraumatic shape. The first portion 799 can have a cross-sectional diameter that is larger than a cross-sectional diameter of the radially inwardly tapering portion 774, which in turn has a cross-sectional diameter that is larger than a cross-sectional diameter of the end cap 750. While the taper of the second portion 774 illustrated in FIG. 15U is generally constant, an accelerating, decelerating, undulating, or other taper could be employed as well. The exit port can span one, two, or more of the first portion 799, second portion 774, or third cap portion 750. In some embodiments, the angled surfaces 789a and 789b have intersecting longitudinal axes that form an angle of between about 30 degrees and 150 degrees, between about 60 degrees and about 120 degrees, between about 75 degrees and 115 degrees, or about 90 degrees. In some embodiments, angled surface 789b has an axial length that is greater or less than the axial length of angled surface 789a, such as by at least about 5%, 10%, 15%, 20%, 25%, or more. Angled surface 789b can have the same axial length as angled surface 789a in other embodiments.

Referring to FIGS. 15V-15V2, there is illustrated a distal tip 730 similar to that of FIG. 15U, but also including one, two, three, or more rippled zones 777. FIG. 15V1 is a cross-sectional view through line A-A of FIG. 15V, while FIG. 15V2 is a perspective view. In some embodiments, the rippled zones 777 may help slow the flow of injectable material to allow for greater control over the dispensation of fluid.

Referring to FIGS. 15W-15W2, there is illustrated a schematic diagram including non-limiting examples of particular dimensions for a distal tip similar to that illustrated in FIGS. 15U and 15V according to one embodiment. FIG. 15W1 is a perspective view, and FIG. 15W2 is a side view. For example, in some embodiments, the distal tip could have an overall length of between about 0.15 and 0.25 inches, such as between about 0.17 and 0.23 inches, or about 0.193 inches as shown. The aperture 728 could in some embodiments, have a maximal linear dimension of between about 0.05 and 0.15 inches, such as between about 0.08 and 0.12 inches, or about 0.094 inches in some embodiments. In accordance with FIGS. 15W-15W2, a distal tip 730 is provided having an aperture 728 with non-parallel angled surfaces 789a, 789b that allow dispensing of injectable material. In some embodiments, the distal-most angled surface 789b of the aperture 728 has an axis P4 that intersects both the longitudinal axis of the distal tip P3 or an axis normal to the longitudinal axis of the distal tip P5 at an angle of about 45 degrees. In other embodiments, the angle could be between about 0 and 90 degrees, such as between about 15 and 75 degrees, between about 15 and 45 degrees, or between about 30 and 60 degrees. The angle formed between an axis of the proximal-most angled surface 789a could be as described above, and could be the same, less, or greater than the angle formed between an axis of the distal-most angled surface 789b and the longitudinal axis P3 of the distal tip. The distal tip 730 includes a radially inwardly (from proximal to distal) tapering wall 773 that transitions into a dome-like distal end cap 750. In some embodiments, opposing zones of tapered wall 773, in some embodiments, resides in planes P1, P2 that intersect at an angle approximately 15 degrees to 45 degrees, such as about 15 to 25 degrees, or about 20.5° in some embodiments as illustrated, although other angles between 0 and 90 degrees are also possible.

Figure 15X:
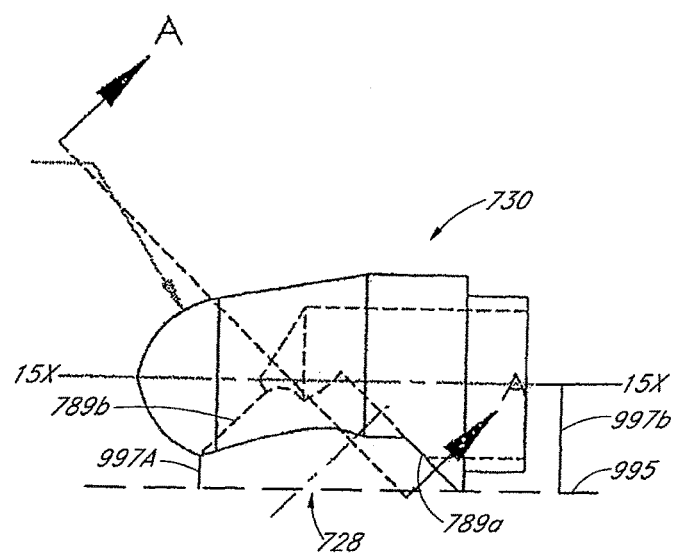

FIG. 15X illustrates a side schematic view of the distal tip 730 illustrated in FIG. 15W, also illustrating a radially asymmetric offset 997A of the aperture 728 (e.g., from proximal radial termination of wall 789a and distal radial termination of wall 789b) from its proximal end to its distal end. In part due to the offset 997A, a cement flow out of the aperture 728 could be prevented from easily and prematurely severing at the aperture 728, for example, when the injector is rotated while the distal tip 730 is positioned near cancellous bone. In some embodiments, the offset distance 997A could be between about 0.01 and 0.05 inches, such as between about 0.01 and 0.03 inches. In some embodiments, the offset distance 997A is at least about 2%, 3%, 5%, 7%, 10%, 12%, 15%, or more of the distance from line 15X-15X (connecting the midpoints of the width of the distal tip 730 from its proximal end to its distal end) to the section of the tip 730 that extends the farthest radially outward, illustrated as distance 997B. In other embodiments, the offset distance 997A is no more than about 15%, 12%, 10%, 7%, 5%, 3%, 2%, or less of the distance 997B. Other embodiments, including that of FIGS. 15U-15U2, can also be configured to have angled surfaces with an offset as described.

As a further alternative, coring during insertion of an injector having a distal opening 728 may be prevented by positioning a removable obturator 999 in the distal opening, as illustrated schematically in FIG. 15Y. The obturator 999 comprises an elongate body, extending from a proximal end throughout the length of the injector to a blunt distal tip. The obturator 999 is advanced axially in a distal direction through the central lumen, until the distal tip of the obturator extends slightly distally of the distal opening 728 in the injector. This provides a blunt atraumatic tip for distal advance of the injector through tissue. Following positioning of the injector, the obturator 999 may be proximally withdrawn from the central lumen, and discarded. The obturator 999 may be provided with any of a variety of structures for securing the obturator 999 within the central lumen during the insertion step, such as a proximal cap for threadably engaging a complementary Luer connector on the proximal opening of the central lumen.

In accordance with another aspect of the present invention, there is provided a combination device in which a steerable and curvable injector is additionally provided with one or two or more cavity formation elements. Thus, the single device may be advanced into a treatment site within a bone, expanded to form a cavity, and used to infuse bone cement or other media into the cavity. Either or both of the expansion step and the infusion step may be accomplished following or with deflection of the distal portion of the injector.

Referring to FIGS. 16A and 16B, the distal portion 302 of a steerable and curvable injector 300 having a cavity formation element 320 thereon is schematically illustrated. The steerable and curvable injector 300 includes a relatively rigid proximal section 304 and a deflectable section 306 as has been discussed elsewhere herein. The lateral flexibility of distal section 306 may be accomplished in any of a variety of ways, such as by the provision of a plurality of transverse chevrons or slots 308. Slots 308 may be machined or laser cut into appropriate tube stock, such as stainless steel or any of a variety of rigid polymers.

The slots 308 oppose a column strength element such as an axially extending spine 310, for resisting axial elongation or compression of the device. A pull wire 312 axially moveably extends throughout the length of the tubular body, and is secured with respect to the tubular body distally of the transverse slots 308. The proximal end of the pull wire is operatively connected to a control on a proximal handpiece or manifold. The control may be any of a variety of structures, such as a lever, trigger, slider switch or rotatable thumb wheel or control knob. Axial proximal traction (or distal advance) of the pull wire 312 with respect to the tubular body causes a lateral deflection of the distal steering section 306, by axial compression or expansion of the transverse slots 308 relative to the spine 310.

A distal aperture 314 is in communication via a central lumen 316 with the proximal end of the steerable and curvable injector 300. Any of a variety of tip configurations may be used such as those disclosed elsewhere herein. The proximal end of the central lumen 316 may be provided with a Luer connector, or other connection port to enable connection to a source of media such as bone cement to be infused. In the illustrated embodiment, the aperture 314 faces distally from the steerable and curvable injector 302, although other exit angles may be used as will be discussed below.

The steerable and curvable injector 300 is optionally provided with a cavity forming element 320, such as an inflatable balloon 322. In the illustrated embodiment, the inflatable balloon 322 is positioned in the vicinity of the steerable and curvable distal section 306. Preferably, the axial length of a distal leading segment 307 is minimized, so that the balloon 322 is relatively close to the distal end of the steerable and curvable injector 300. In this embodiment, the plurality of transverse slots 308 are preferably occluded, to prevent inflation media from escaping into the central lumen 316 or bone cement or other injective media from escaping into the balloon 322. Occlusion of the transverse slots 308 may be accomplished in a variety of ways, such as by positioning a thin tubular membrane coaxially about the exterior surface of the tubular body and heat shrinking or otherwise securing the membrane across the openings. Any of a variety of heat shrinkable polymeric sleeves, comprising high density polyethylene, polyvinyl chloride, ethylvinyl acetate, polyethylene terephthalate, polyurethane, mixtures, and block or random copolymers, or other materials, are well known in the catheter arts. Alternatively, a tubular liner may be provided within the central lumen 316, to isolate the central lumen from the transverse slots 308.

The balloon 322 is secured at a distal neck 309 to the leading segment 307 as is understood in the balloon catheter arts. The distal neck 309 may extend distally from the balloon, as illustrated, or may invert and extend proximally along the tubular body. In either event, the distal neck 309 of the balloon 322 is preferably provided with an annular seal 324 either directly to the tubular body 301 or to a polymeric liner positioned concentrically about the tubular body, depending upon the particular device design. This will provide an isolated chamber within balloon 322, which is in fluid communication with a proximal source of inflation media by way of an inflation lumen 326.

In the illustrated embodiment, the balloon 322 is provided with an elongate tubular proximal neck which extends throughout the length of the steerable and curvable injector 300, to a proximal port or other site for connection to a source of inflation media. This part can be blow molded within a capture tube as is well understood in the balloon catheter arts, to produce a one piece configuration. Alternatively, the balloon can be separately formed and bonded to a tubular sleeve. During assembly, the proximal neck or outer sleeve 328 may conveniently be proximally slipped over the tubular body 301, and secured thereto, as will be appreciated by those of skill in the catheter manufacturing arts. In some embodiments, the balloon 322 has a lubricous coating that can be chemically bonded or physically coated.

Figure 16G:
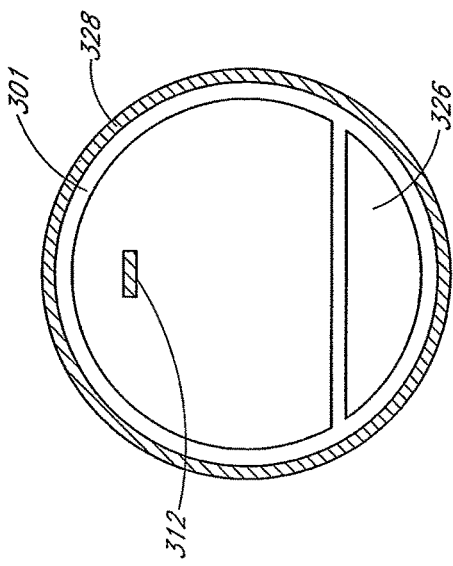
FIGS. 16E-16G illustrate cross-sections of further alternative inflation lumen configurations.
Figure 16F:
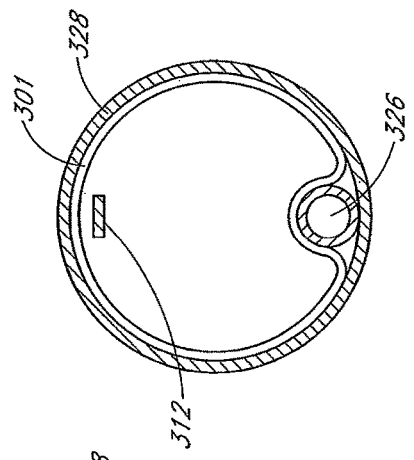
Figure 16E:
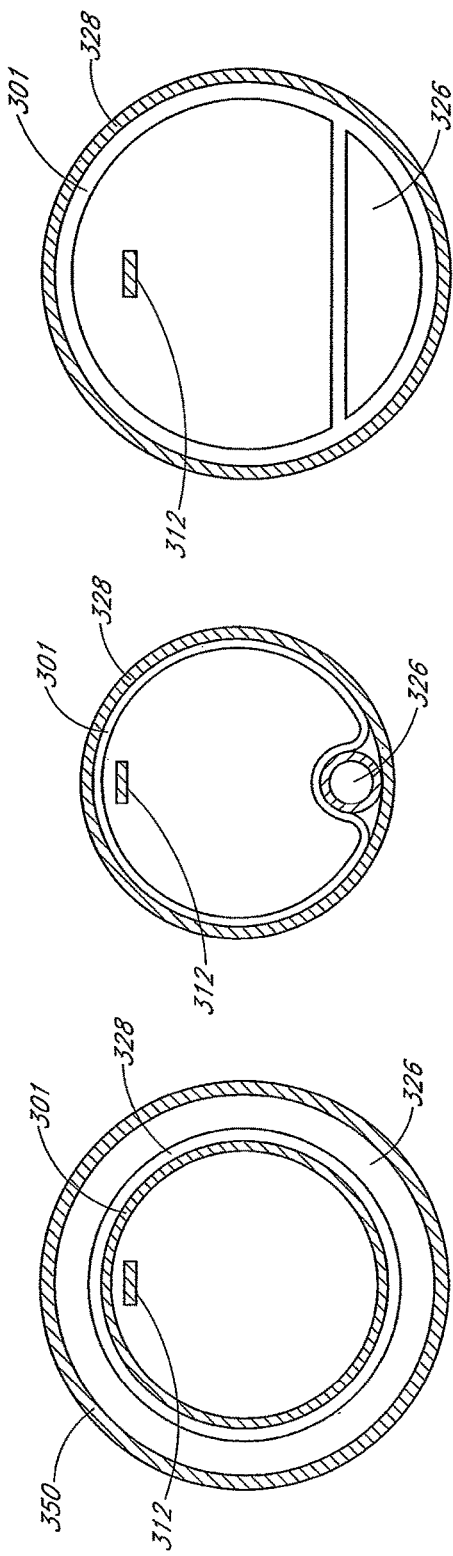

Referring to FIG. 16C, the inflation lumen 326 may occupy an annular space between the outer sleeve 328 and the tubular body 301. This may be accomplished by sizing the inside dimension of the outer sleeve 328 slightly larger than the outside dimension of the tubular body 301, by an amount sufficient to enable the desired inflation flow rate as understood in catheter art. Alternatively, referring to FIG. 16D, a discrete inflation lumen 326 may be provided while the remainder of the outer sleeve 328 is bonded or snuggly fit against the tubular body 301. This may be accomplished by positioning an elongate mandrel (not illustrated) between the outer sleeve 328 and the tubular body 301, and heat shrinking or otherwise reducing the outer sleeve 328, thereafter removing the mandrel to leave the discrete inflation lumen 326 in place. In another embodiment, a cross-section of a catheter with a balloon having an inflation lumen 326 with outer layer 350 coextensive with the outer surface of the balloon coaxial with sleeve 328 and tubular body 301 is shown in FIG. 16E. FIG. 16F illustrates a cross-section of another embodiment with an inflation lumen 326 external to the tubular body 301. FIG. 16G illustrates a cross-section of another embodiment with an inflation lumen 326 with a lumen internal to the tubular body 301. In some embodiments, the internal inflation lumen 326 can be integrally formed with the tubular body 301 as shown. Alternatively, any of a variety of other inflation lumen 326 configurations can be used.

In some embodiments, the cavity-creating element could include a reinforcing layer that may be, for example, woven, wrapped or braided (collectively a "filament" layer), for example, over the liner of a balloon. The filament layer can advantageously protect the balloon from damage while in the working space, for example from jagged cancellous bone fragments within the interior of the vertebral body. The filament layer can also significantly elevated the burst pressure of the balloon, such that it exceeds about 20 atmospheres (ATM), in some embodiments exceeds about 25 ATM, and in a preferred embodiment, is at least about 30 ATM.

The filament layer can also be configured to control the compliance of the balloon depending on the desired clinical result, either symmetrically or, if the filaments are asymmetric, to constrain expansion of the balloon in one or more directions. In some embodiments, the balloon can be said to have a first compliance value when inflated to a first volume at a given first pressure when the balloon expands without being mechanically constrained by the constraining element such as the filament layer. The balloon can have a second compliance value when further inflated to a second volume (greater than the first volume) at a given second pressure (greater than the first pressure) when the balloon expands while being mechanically constrained by the constraining element. The second compliance value is, in some embodiments, less than the first compliance value due to the effect of the constraining element on the balloon. The second compliance value can be, for example, at least about 5%, 10%, 15%, 20%, 25%, 30%, 40%, 50%, 60%, or 70% less than the first compliance value. In other embodiments, the second compliance value can be, for example, no more than about 70%, 60%, 50%, 40%, 30%, 25%, 20%, 15%, 10%, or 5% less than the first compliance value. In embodiments with a plurality of braided layers, the balloon could have an additional third, fourth, etc. progressively lower compliance values.

Figure 16J:
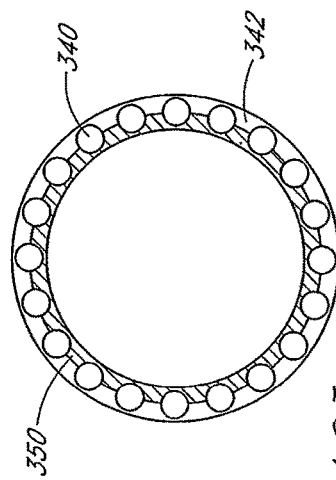
FIG. 16J illustrates a cross-section similar to that of FIG. 16I with an additional exterior layer.
Figure 16I:
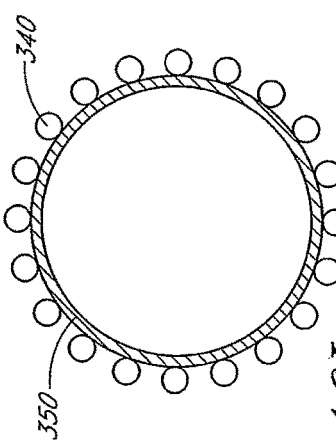
FIG. 16I illustrates a cross-section through line 16I-16I of FIG. 16H, which some elements omitted for clarity.
Figure 16H:
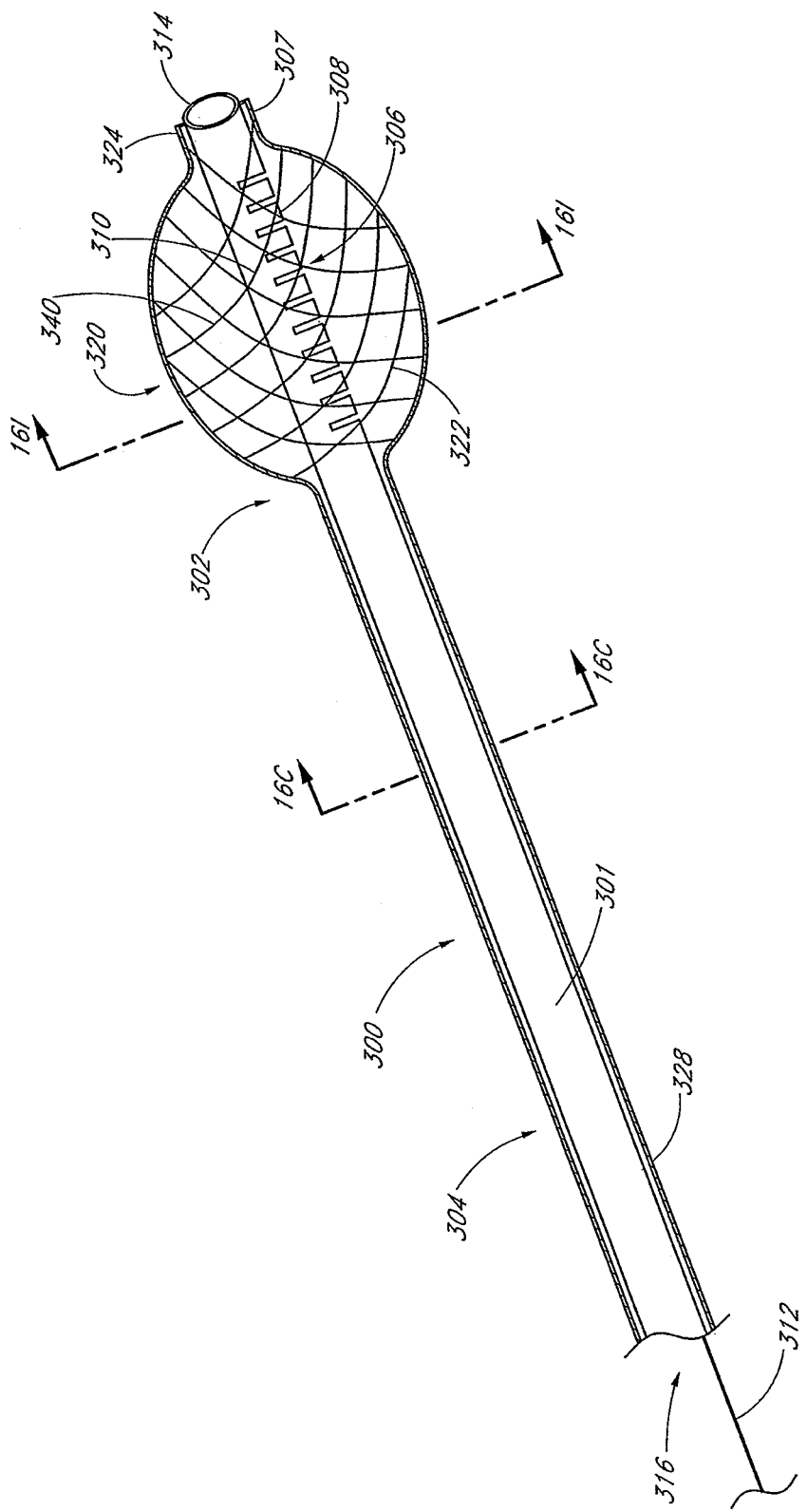
FIG. 16H schematically illustrates the distal end of a steerable and curvable injection device having a cavity creation element with a braided layer.

FIG. 16H schematically illustrates a vertebroplasty catheter 300 with a cavity creation element, namely a balloon 322 with a filament layer 340 carried by the balloon. FIG. 16I illustrates a cross-section of the filament reinforced balloon 322 through line 161-161 of FIG. 16H, with filaments 340 surrounding the sidewall 350 of the balloon 322. FIG. 16J illustrates a cross-section of an alternative embodiment with filaments 340 over balloon sidewall 350 and also another layer 342 exterior to the braided layer 340. Other features have not been illustrated in FIGS. 16I and 16J for clarity. The exterior layer 342 could be made of, for example, a material discussed with respect to polymeric sleeve construction noted above, nylon, urethane, PET, or a thermoplastic. In some embodiments, there may be multiple layers, such as made of a polymer, exterior to the filament layer 340 and/or multiple liner layers interior to the filament 340, as well as multiple braided or other filament layers between or amongst the various layers. In some embodiments, the filament 340 is co-molded within a wall 350 of the balloon 322 itself.

The filament 340 may comprise any of a variety of metallic ribbons, although wire-based braids could also be used. In some embodiments, the ribbons can be made at least in part of wires in braids or made of strips of a shape memory material such as Nitinol or Elgiloy, or alternatively stainless steel, such as AISI 303, 308, 310, and 311. When using a braid 340 containing some amount of a super-elastic alloy, an additional step may be desirable in some embodiments to preserve the shape of the stiffening braid 340. For instance, with a Cr-containing Ni/Ti superelastic alloy which has been rolled into 1 mm×4 mm ribbons and formed into a 16-member braid 340, some heat treatment is desirable. The braid 340 may be placed onto a, e.g., metallic, mandrel of an appropriate size and then heated to a temperature of 600 degrees Fahrenheit to 750 degrees Fahrenheit for a few minutes, to set the appropriate shape. After the heat treatment step is completed, the braid 340 retains its shape and the alloy retains its super-elastic properties.

In some embodiments, metallic ribbons can be any of a variety of dimensions, including between about 0.25 mm and 3.5 mm in thickness and 1.0 mm and 5.0 mm in width. Ribbons can include elongated cross-sections such as a rectangle, oval, or semi-oval. When used as ribbons, these cross-sections could have an aspect ratio of thickness-width of at least 0.5 in some embodiments.

In some embodiments, the braid 340 may include a minor amount of fibrous materials, both synthetic and natural, may also be used. In certain applications, particularly in smaller diameter catheter sections, more malleable metals and alloys, e.g., gold, platinum, palladium, rhodium, etc., can be used. A platinum alloy with a few percent of tungsten is sometimes could be used partially because of its radio-opacity.

Nonmetallic ribbons or wires can also be used, including, for example, materials such as those made of polyaramides (Kevlar), polyethylene terephthalate (Dacron), polyamides (nylons), polyimide carbon fibers, or a shape memory polymer.

In some embodiments, the braids 340 can be made using commercial tubular braiders. The term "braid" when used herein includes tubular constructions in which the wires or ribbons making up the construction are woven in an in-and-out fashion as they cross, so as to form a tubular member defining a single lumen. The braid members may be woven in such a fashion that 2-4 braid members are woven together in a single weaving path, although single-strand weaving paths can also be used. In some embodiments, the braid 340 has a nominal pitch angle of 45 degrees. Other braid angles, e.g., from 20 degrees to 60 degrees could also be used.

Figure 16K:
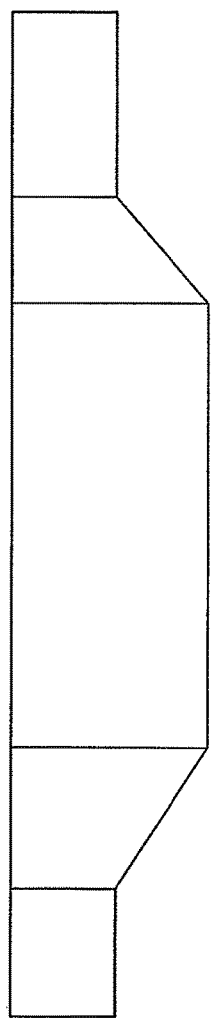
FIGS. 16K-16M illustrate various views of an asymmetrical cavity creation element, according to some embodiments of the invention.
Figure 16L:
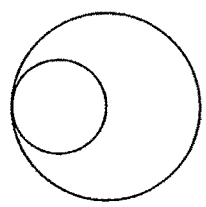
Figure 16M:
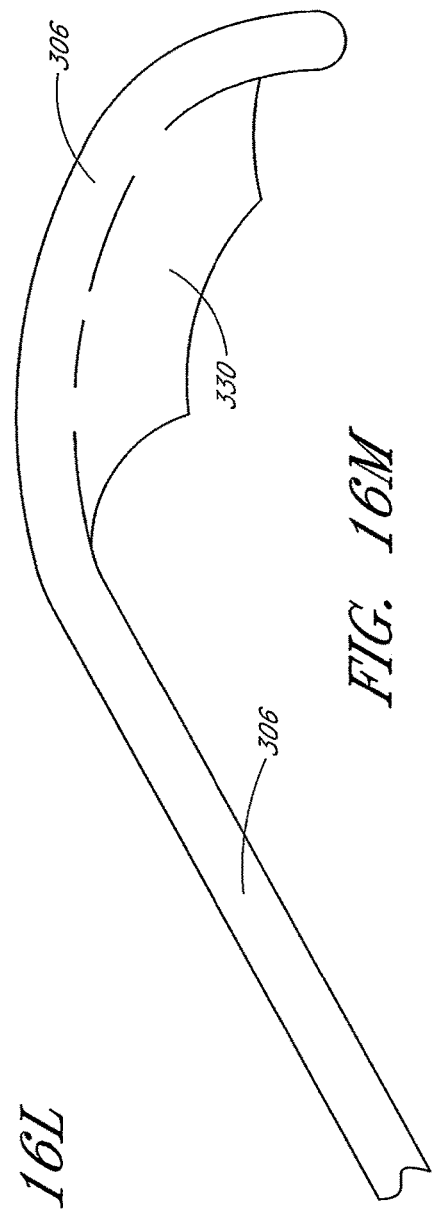
Figures 16O, 16P:
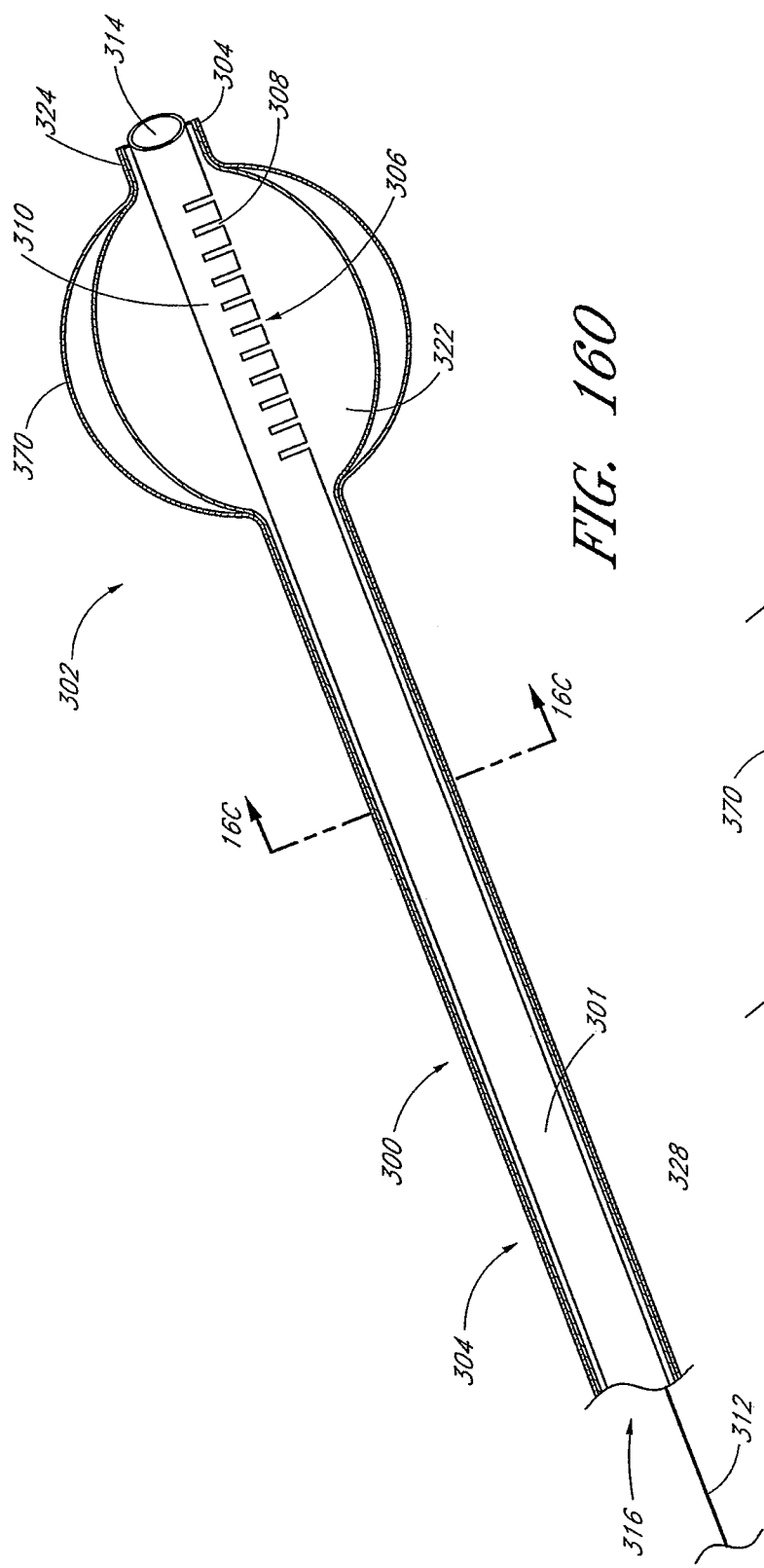
FIGS. 16O and 16P schematically illustrate views of a catheter with a plurality of coaxial balloons, according to some embodiments of the invention.

In some embodiments, the cavity creation element includes two or more coaxial balloons, including an inner balloon 322 and an outer balloon 370 as illustrated schematically in FIG. 16O. Inner balloon 322 can be oriented in a first direction, such as more axially, while outer balloon 370 is oriented in a second direction, such as more radially. Balloon wall orientation, such as by stretching, is well understood in the art. The coaxial balloon configuration advantageously provides improved strength and burst resistance while minimizing the wall thickness of each balloon. Thus, two or more relatively thin-walled balloons can be utilized rather than a single thick-walled balloon to achieve both higher burst pressure and lower crossing profile. FIG. 16P illustrates a schematic cross-section of a section of the inner balloon wall 322 and outer balloon wall 370 that can be separated by a slip plane 372 that may have a friction-reducing lubricious coating or the like. In some embodiments, two, three, four, or more coaxially arranged balloons can be used in the same fashion. In some embodiments, one or more coaxial balloons is interspersed or integrated with one or more braided or other filament layers as described above. In some embodiments, each balloon could have a thickness of between about 0.0005 inches to 0.008 inches, or between about 0.001 inches to about 0.005 inches in other embodiments.

In some embodiments, the cavity creation element could be asymmetrical, for example, as with the balloon 344 offset from the longitudinal axis of the tubular body 301 illustrated schematically in FIG. 16K. Such a balloon configuration can be advantageous, for example, if the vertebral fracture is generally more anterior, so that the balloon 344 can be positioned to expand away from the anterior area to reduce the risk of balloon expansion causing a rupture all the way through the cortical bone of the vertebrae. A cross-sectional schematic view through the inflated offset balloon 344 is illustrated in FIG. 16L, also illustrating the tubular body 301. Other components such as guidewire 312 have been omitted for clarity purposes. In some embodiments, various balloons as described in FIGS. 1-20 and the accompanying disclosure of U.S. Pat. No. 6,066,154 to Reiley et al., which is hereby incorporated by reference in its entirety can also be used in connection with the injector 300 described herein. A schematic illustration of an offset balloon 344 on the catheter 300 when the distal segment 306 is deflected is illustrated in FIG. 16M.

Referring to FIGS. 17A and 17B, there is illustrated an alternative embodiment in which the distal aperture 314 is provided on a side wall of the tubular body. One or two or three or more distal apertures 314 may be provided in any of the embodiments disclosed herein, depending upon the desired clinical performance. In the illustrated embodiment, the distal aperture 314 is provided on the inside radius of curvature of the steerable and curvable section 306, as illustrated in FIG. 17B. The aperture 314 may alternatively be provided on the opposite, outside radius of curvature, depending upon the desired clinical performance.

As a further alternative, the distal aperture or apertures 314 may be provided in any of a variety of configurations on a distal cap or tip, adapted to be secured to the tubular body.

In some embodiments, it may be advantageous to have multiple cavity-creation elements on a steerable and curvable injector in order to, for example, more quickly and efficiently move sclerotic cancellous bone to better facilitate cavity formation and the subsequent introduction of cement media. Referring to FIGS. 17C and 17D, there is an illustrated another embodiment of a steerable and curvable injector with a plurality of cavity creation elements thereon schematically illustrated, such as at least two, three, four, or more cavity creation elements. The cavity creation elements can be, for example, a first balloon 330 and a second balloon 332 as shown. As illustrated, both the first balloon 330 and the second balloon 332 are positioned in the vicinity of the steerable and curvable distal section 306. In other embodiments, as illustrated in FIGS. 17G and 17H, the first balloon 330 is positioned in the vicinity of the steerable and curvable distal section 306 while the second balloon 332 is positioned more proximally on the more rigid proximal section 304. In still other embodiments, as illustrated in FIGS. 17I and 17J, the first balloon 330 is positioned in the vicinity of the steerable and curvable distal section 306 while the second balloon 332 is positioned partially on the proximal section 304 and partially on the steerable and curvable distal section 306. In other embodiments, both the first balloon 330 and the second balloon 332 can be positioned in the vicinity of the proximal section 306.

In some embodiments, the first balloon 330 and the second balloon 332 share a common inflation lumen 326 (such as illustrated in FIG. 16C or D) and thus can be simultaneously inflatable from a common source of inflation media. In other embodiments, the first balloon 330 and the second balloon 332 have separate respective first inflation lumen 326 and second inflation lumen 327 and thus can be inflated according to the desired clinical result, e.g., simultaneously or the second balloon 332 inflated before or after the first balloon 330. FIGS. 17E and 17F are alternative cross sectional views showing different inflation lumen configurations. As illustrated in FIG. 17E, in some embodiments the first inflation lumen 328 can be positioned concentrically around the second inflation lumen 329, both of which can occupy annular spaces between the outer sleeve 328 and the tubular body 301. FIG. 17F illustrates an alternative embodiment where first 326 and second 327 discrete inflation lumens may be provided while the remainder of the outer sleeve 328 is bonded or snuggly fit against the tubular body 301.

The first balloon 330 and the second balloon 332 can have substantially the same properties or differing properties, such as thickness, material, inflation diameter, burst strength, compliance, or symmetry (or lack thereof) depending on the desired clinical result. In some embodiments, the distal aperture 314 could be distally facing, positioned on a side wall, or on an inclined surface; or 2, 3, 4, 5, or more apertures could be presented as previously described. Furthermore, while the aperture 314 is illustrated in FIGS. 17C-17D, and 17G-17J as positioned on the distal end of the catheter 300 as being distal to both first balloon 330 and second balloon 332 in some embodiments the aperture 314 or additional aperture(s) can be positioned in between first balloon 330 and second balloon 332 and/or proximal to second balloon 332. In embodiments with one or more cavity creating elements having multiple apertures, the apertures could be fluidly communicate with each other, or be fluidly isolated in other embodiments.

The steerable and curvable injection systems described above are preferably used in conjunction with a mixing and dispensing pump for use with a multi-component cement. In some embodiments, a cement dispensing pump is a handheld device having an interface such as a tray or chamber for receiving one or more cartridges. In one embodiment, the pump is configured to receive a double-barreled cartridge for simultaneously dispensing first and second bone cement components. The system additionally includes a mixing chamber, for mixing the components sufficiently and reproducibly to fully automate the mixing and dispensing process within a closed system. In some embodiments, the cavity creation element(s) such as balloons described above can be coated or impregnated with particles such as those described in U.S. Pat. Pub. No. 2007/0185231 to Liu et al., hereby incorporated by reference in its entirety. The particles can be released within the vertebral cavity upon expansion or other transformation of the cavity-creating element in order to promote bone ingrowth into the bone cement or improve the crack arrestation properties of the composite bone cement.

Bone cement components have conventionally been mixed, such as by hand, e.g., in mixing bowls in the operating room, which can be a time-consuming and inelegant process. The devices disclosed herein may be used with conventional bone cement formulations, such as manually mixed liquid-powder PMMA formulations. The mixed bone cement can then be transferred to an infusion device, such as a syringe connectable to the input port of the steerable vertebroplasty device, such that bone cement can be delivered through the steerable vertebroplasty device to a desired anatomical location within the body. In one embodiment, a first bone cement component, such as a cement powder, can be placed into a mixing bowl. A second bone cement component such as a liquid monomer, can be poured over the cement powder. The first and second bone cement components can then be mixed. The bone cement is then moved from the mixing bowl into a cement reservoir. The cement reservoir can have a distal opening connectable to the input port of the steerable vertebroplasty device, and a proximal cap having an opening connectable to a pump, such as a hydraulic pump. When the pump is connected to the cement reservoir, actuation of a pump control (e.g., turning a control, such as a knob) on the pump can urge the bone cement within the cement reservoir into the input port of the steerable vertebroplasty device for delivery to a desired anatomical location. Alternatively, the use of a closed mixing device such as a double-barreled dispensing pump as disclosed herein is highly advantageous in reducing bone cement preparation time, preventing escape of fumes or ingredients, ensuring that premature cement curing does not occur (i.e., the components are mixed immediately prior to delivery into the body), and ensuring adequate mixing of components.

Two separate chambers contain respective materials to be mixed in a specific ratio. Manual dispensing (e.g., rotating a knob or squeezing a handle) forces both materials into a mixing nozzle, which may be a spiral mixing chamber within or in communication with a nozzle. In the spiral mixing nozzle, all or substantially all mixing preferably occurs prior to the bone cement entering the steerable and curvable injection needle and, subsequently, into the vertebra. The cement dispensing hand pump may be attached to the steerable and curvable injection needle permanently, or removably via a connector, such as slip-ring Luer fittings. A wide range of dispensing pumps can be modified for use with the present invention, including dispensing pumps described in, for example, U.S. Pat. Nos. 5,184,757, 5,535,922, 6,484,904, and Patent Publication No. 2007/0114248, all of which are incorporated by reference in their entirety.

Currently favored bone cement compositions are normally stored as two separate components or precursors, for mixing at the clinical site shortly prior to implantation. As has been described above, mixing of the bone cement components has traditionally been accomplished manually, such as by expressing the components into a mixing bowl in or near the operating room. In accordance with the present invention, the bone cement components may be transmitted from their storage and/or shipping containers, into a mixing chamber, and into the patient, all within a closed system. For this purpose, the system of the present invention includes at least one mixing chamber positioned in the flow path between the bone cement component container and the distal opening on the bone cement injection needle. This permits uniform and automated or semi-automated mixing of the bone cement precursors, within a closed system, and thus not exposing any of the components or the mixing process at the clinical site.

Thus, the mixing chamber may be formed as a part of the cartridge, may be positioned downstream from the cartridge, such as in-between the cartridge and the proximal manifold on the injection needle, or within the proximal manifold on the injection needle or the injection needle itself, depending upon the desired performance of the device. The mixing chamber may be a discrete component which may be removably or permanently coupled in series flow communication with the other components of the invention, or may be integrally formed within any of the foregoing components.

In general, the mixing chamber includes an influent flow path for accommodating at least two bone cement components. The first and second incoming flow path is combined, and mixing structures for facilitating mixing of the components are provided. This may include any of a variety of structures, such as a helical flow path, baffles and or additional turbulence inducing structures.

Tables 1-2 below depict the contents and concentrations of one exemplary embodiment of bone cement precursors. Chambers 1A and 1B contain precursors for a first cement composition for distribution around the periphery of the formed in place vertebral body implant with a higher particle concentration to promote osteoconduction and/or osteoinduction, as discussed previously in the application. Chambers 2A and 2B contain precursors for a second cement composition for expression more centrally within the implanted mass within the vertebral body, for stability and crack arresting, as discussed previously in the application.

One of ordinary skill in the art will recognize that a wide variety of chamber or cartridge configurations, and bone cements, can be used with the present injection system. For example, in one embodiment, a first cartridge includes pre-polymerized PMMA and a polymerization catalyst, while a second cartridge includes a liquid monomer of MMA as is common with some conventional bone cement formulations. In some embodiments, the contents of two cartridges can be combined into a single cartridge having multiple (e.g., four) chambers. Chambers may be separated by a frangible membrane (e.g., 1A and 2A in a first cartridge and 1B and 2B in a second cartridge, each component separated by the frangible membrane or other pierceable or removable barrier). In other embodiments, contents of the below cartridges can be manually pre-mixed and loaded into the input port of the injection system without the use of a cement mixing dispenser.

TABLE 1

| Chamber 1A | |
|---|---|
| Methyl methacrylate (balance) | Hydroquinone (~75 ppm)(stabilizer) |
| N,N-dimethyl-p-toluidine (~0.9%)(catalyst for polymerization) | Sterile bone particles (≥35 wt. %) |
| Barium sulfate (~20 wt. %)(radio-opacifier) | |

| Chamber 1B | |
|---|---|
| Benzoyl peroxide (~2%)(activator for polymerization) | Physiological saline or poppy seed oil (balance) |

TABLE 2

| Chamber 2A | |
|---|---|
| Methyl methacrylate (balance) | Hydroquinone (~75 ppm)(stabilizer) |
| N,N-dimethyl-p-toluidine (~0.9%)(catalyst for polymerization) | Sterile bone particles (~30 wt. %) |
| Barium sulfate (~20 wt. %)(radio-opacifier) | |

| Chamber 2B | |
|---|---|
| Benzoyl peroxide (~2%)(activator for polymerization) | Physiological saline or poppy seed oil (balance) |

As illustrated in FIGS. 18A and 18B, in one embodiment, a system or kit for implanting bone cement includes at least some of the following components: a stylet configured to perforate a hole into the pedicle of the vertebral body; an introducer/cannula 800 for providing an access pathway to the treatment site, a steerable and curvable injection needle 700 to deliver bone cement to a desired location, and, a cement dispensing pump 910 preferably configured to accommodate one or two or more dual chamber cartridges 1200 as well as a mixing nozzle 995.

The stylet may have a diameter of between about 0.030" to 0.300", 0.050" to about 0.200" and preferably about 0.100" in some embodiments. The introducer/cannula 800 is between about 8-14 gauge, preferably between about 10-12 gauge, more preferably 11 gauge in some embodiments. The introducer/cannula 800, which may be made of any appropriate material, such as stainless steel (e.g., 304 stainless steel) may have a maximum working length of no more than about 12", 8", or 6" in some embodiments. One or two or more bone cement cartridges, each having one or two or more chambers, may also be provided. Various other details of the components have been described above in the application.

One embodiment of a method for delivering bone cement into a vertebral body is now described, and illustrated in FIGS. 19A-F. The method involves the general concept of vertebroplasty and kyphoplasty in which a collapsed or weakened vertebra is stabilized by injecting bone cement into cancellous bone.

Figure 19A:
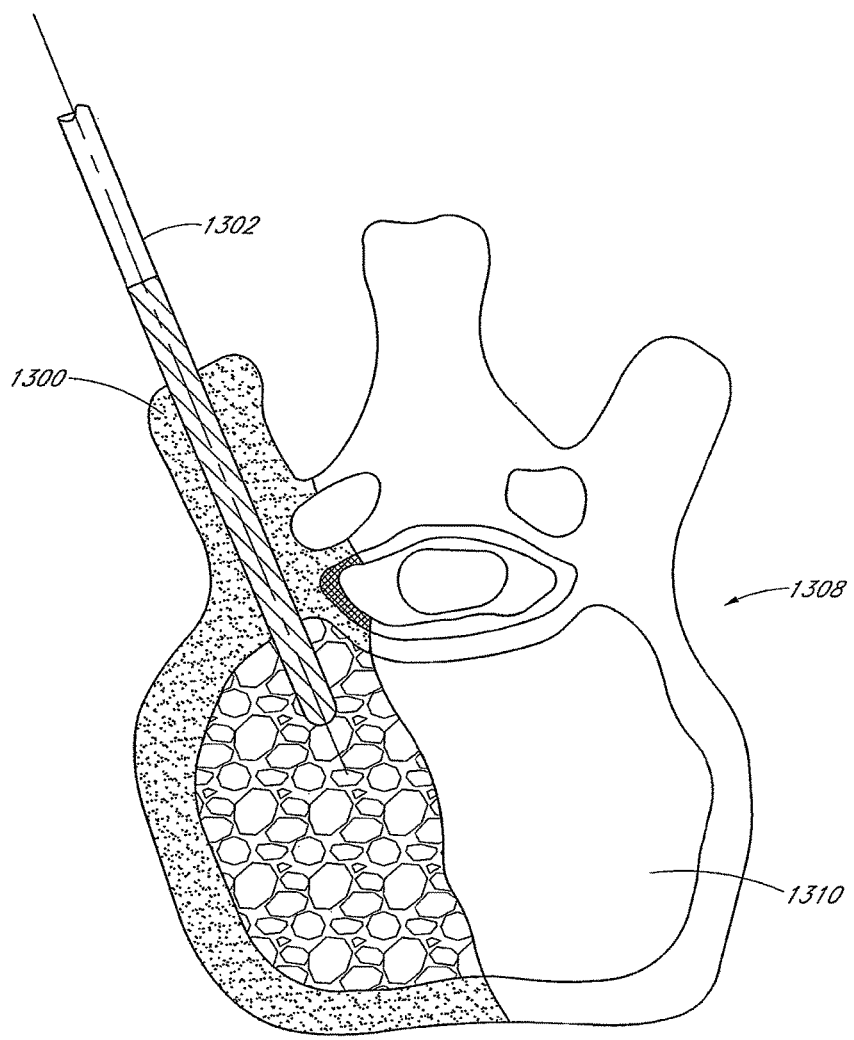
FIGS. 19A through 19F show stages m the method of accomplishing vertebroplasty in accordance with the invention.
Figure 19B:
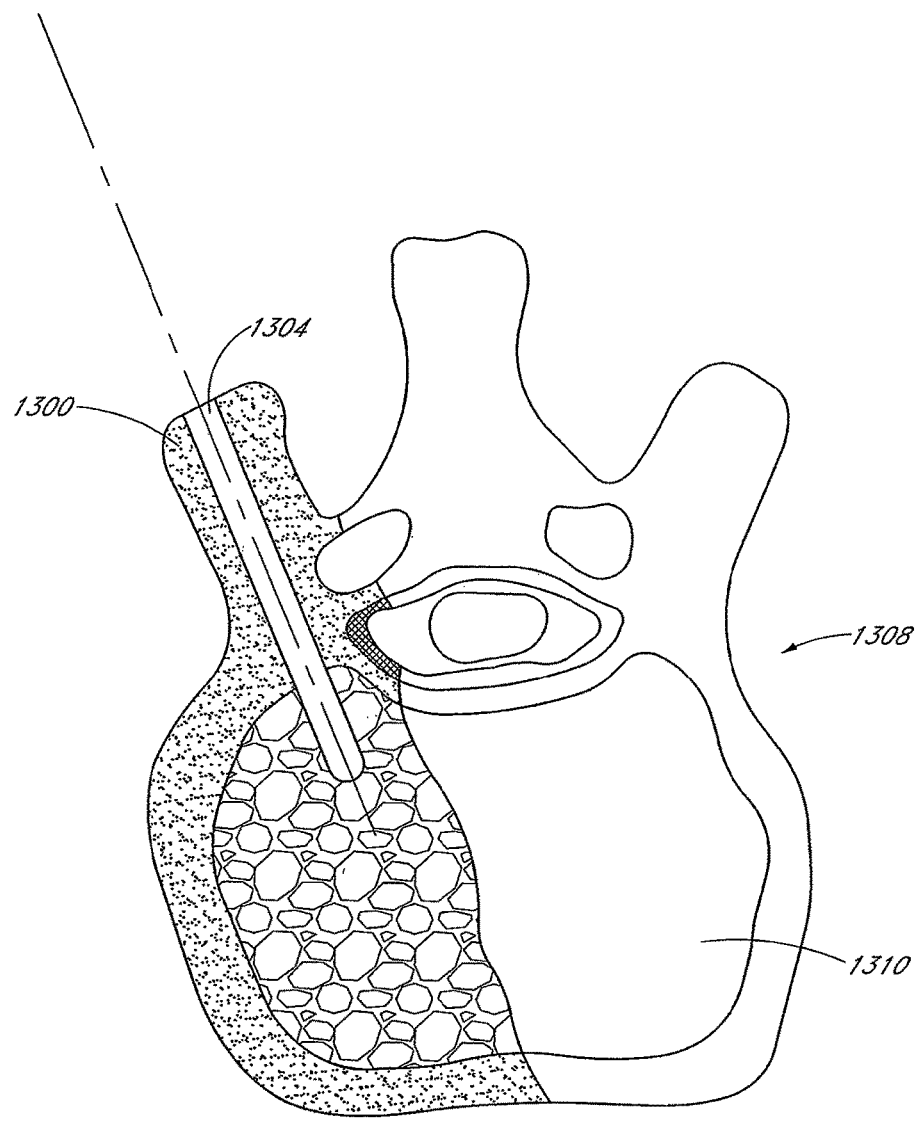
Figure 19C:
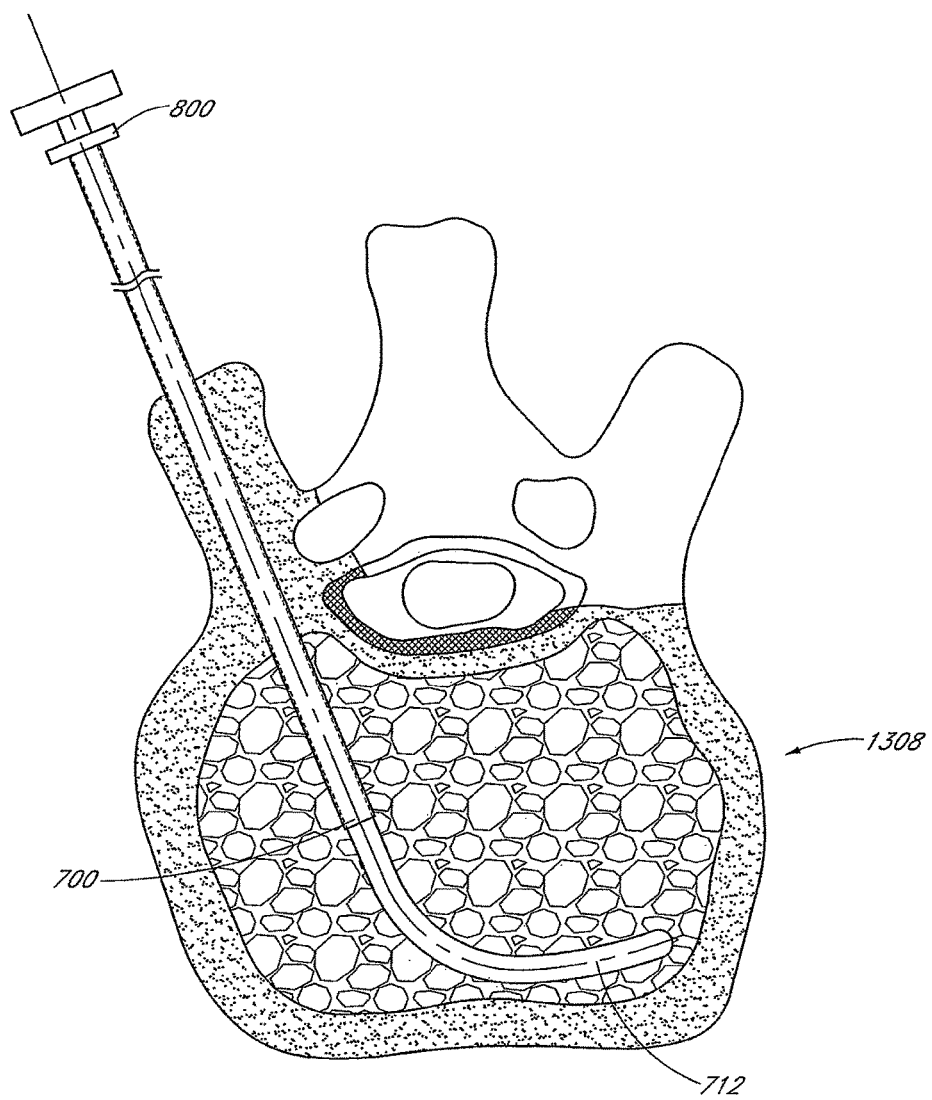

The cement implantation procedure is designed for uni-transpedicular access and generally requires either a local anesthetic or short-duration general anesthetic for minimally invasive surgery. Once the area of the spine is anesthetized, as shown in FIGS. 19A-B, the physician inserts a stylet 1302 to perforate a lumen 1304 into the pedicle wall 1300 of the vertebra 1308 to gain access to the interior of the vertebral body 1310. As illustrated in FIG. 19C, the introducer/cannula 800 is then inserted through the lumen 1304 for bone access as well as acting as the guide for the steerable and curvable injection needle 700. The introducer/cannula 800 is sized to allow physicians to perform vertebroplasty or kyphoplasty on vertebrae with small pedicles 1300 such as the thoracic vertebra (e.g., T5) as well as larger vertebrae (e.g., L5). In addition, this system and method is advantageously designed to allow uni-transpedicular access as opposed to bi-pedicular access, resulting in a less invasive surgical procedure.

Once bone access has been achieved, as shown in FIG. 19C the steerable and curvable injection needle 700 such as any of the devices described above can be inserted through the introducer/cannula 800 and into the vertebra 1308. The entire interior 1310 of the target vertebral body may be accessed using the steerable and curvable injection needle 800. The distal end 712 of the needle 700 can be laterally deflected, rotated, and/or proximally retracted or distally advanced to position the bone cement effluent port at any desired site as previously described in the application. The radius can be adjusted by means of an adjustment control, such as a knob on the proximal end of the device as previously described.

Figure 19D:
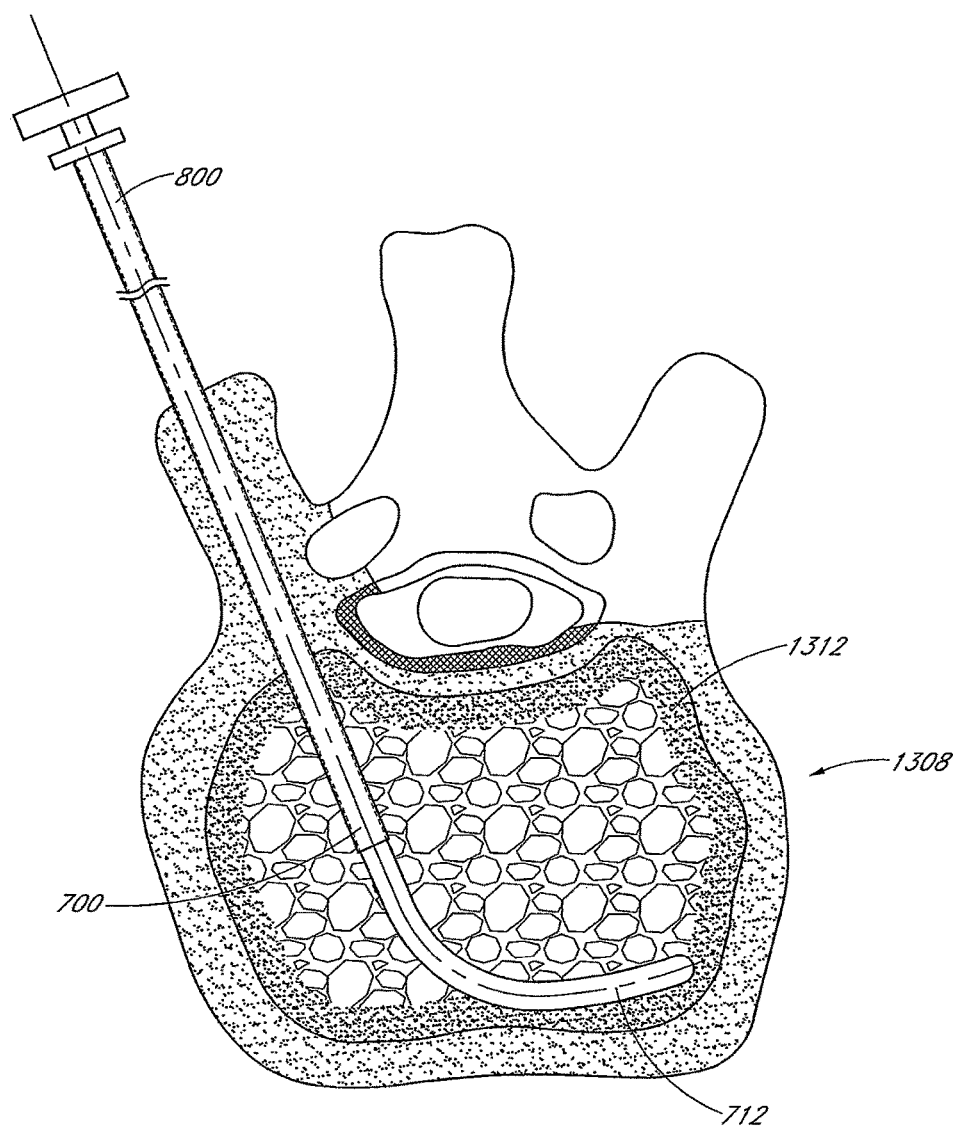
Figure 19E:
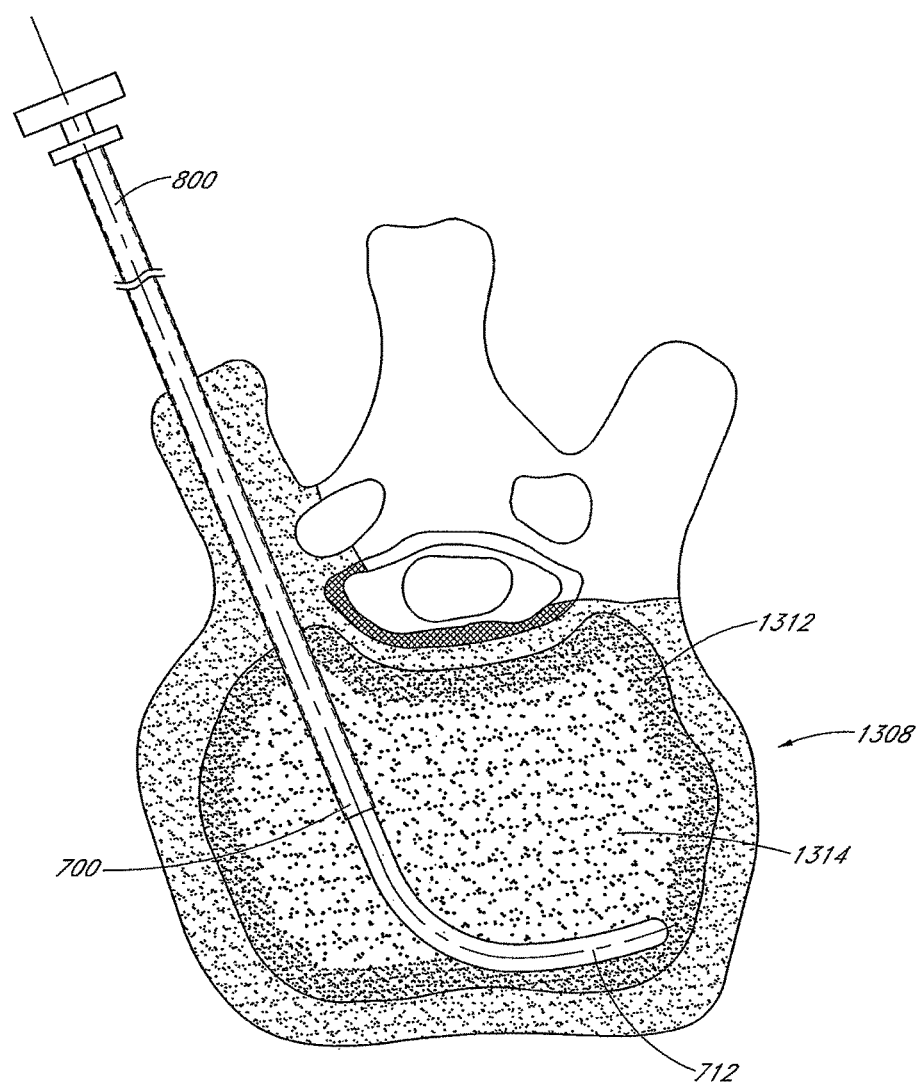

The actual injection procedure may utilize either one or two basic steps. In a one step procedure, a conventional bone cement is introduced as is done in simple vertebroplasty. The first step in the two step injection involves injection of a small quantity of PMMA with more than about 35%, e.g., 60% particles (such as inorganic bone particles) onto the periphery of the treatment site, i.e., next to the cortical bone of the vertebral body as shown in FIG. 19D. This first cement composite 1312 begins to harden rather quickly, forming a firm but still pliable shell, which is intended to minimize or prevent any blood/bone marrow/PMMA content from being ejected through any venules or microfractures in the vertebral body wall. The second step in the procedure involves an injection of a bolus of a second formulation of PMMA with a smaller concentration such as approximately 30% (inorganic bone) particles (second cement composite 1314) to stabilize the remainder of the weakened, compressed cancellous bone, as illustrated in FIG. 19E.

Figure 19F:
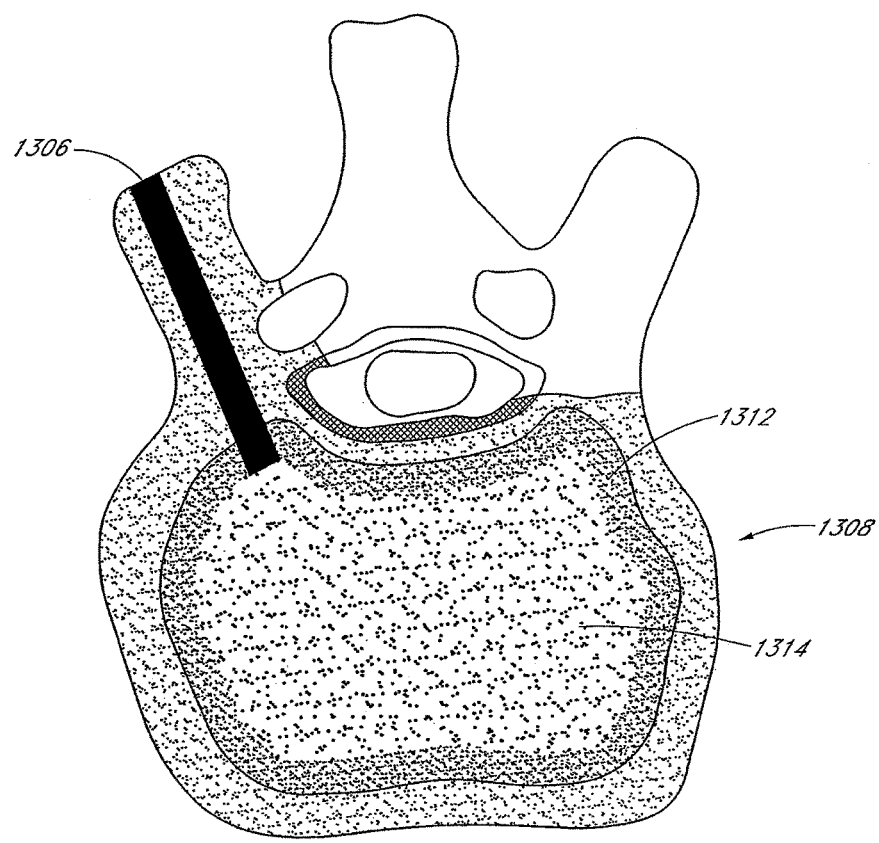

Injection control for the first and second steps is provided by an approximately 2 mm inside diameter flexible introducer/cannula 800 coupled to a bone cement injection pump (not shown) that is preferably hand-operated. Two separate cartridges containing respective bone cement and (inorganic bone) particle concentrations that are mixed in the 60% and 30% ratios are utilized to control (inorganic bone) particle to PMMA concentrations. The amount of the injectate is under the direct control of the surgeon or interventional radiologist by fluoroscopic observation. The introducer/cannula 800 is slowly withdrawn from the cancellous space as the bolus begins to harden, thus preventing bone marrow/PMMA content from exiting the vertebral body 1308. The procedure concludes with the surgical incision being closed, for example, with bone void filler 1306 as shown in FIG. 19F. Both the high and low bone cement particle concentration cement composites 1312, 1314 harden after several minutes. In vitro and in vivo studies have shown that the 60% bone-particle impregnated bone cement hardens in 2-3 minutes and 30% bone-particle impregnated bone cement hardens between 4 to 10 minutes.

The foregoing method can alternatively be accomplished utilizing the combination steerable and curvable needle of FIG. 16A, having a cavity formation structure 320 thereon. Once the steerable and curvable injector 300 has been positioned as desired, such as either with deflection as illustrated in FIG. 19C, or linearly, the cavity forming element 320 is enlarged, such as by introducing inflation media under pressure into the inflatable balloon 322. The cavity forming element 320 is thereafter reduced in cross sectional configuration, such as by aspirating inflation media from the inflatable balloon 322 to produce a cavity in the adjacent cancellous bone. The steerable and curvable injector 300 may thereafter by proximally withdrawn by a small distance, to position the distal opening 314 in communication with the newly formed cavity. Bone cement or other media may thereafter be infused into the cavity, as will be appreciated by those skilled in the art.

At any time in the process, whether utilizing an injection needle having a cavity formation element or not, the steerable and curvable injector may be proximally withdrawn or distally advanced, rotated, and inclined to a greater degree or advanced into its linear configuration, and further distally advanced or proximally retracted, to position the distal opening 314 at any desired site for infusion of additional bone cement or other media. More than one cavity, such as two, or three or more, may be sequentially created using the cavity formation element, as will be appreciated by those of skill in the art.

The aforementioned bone cement implant procedure process eliminates the need for the external mixing of PMMA powder with MMA monomer. This mixing process sometimes entraps air in the dough, thus creating porosity in the hardened PMMA in the cancellous bone area. These pores weaken the PMMA. Direct mixing and hardening of the PMMA using an implant procedure such as the above eliminates this porosity since no air is entrapped in the injectate. This, too, eliminates further weakening, loosening, or migration of the PMMA.

Figure 20A:
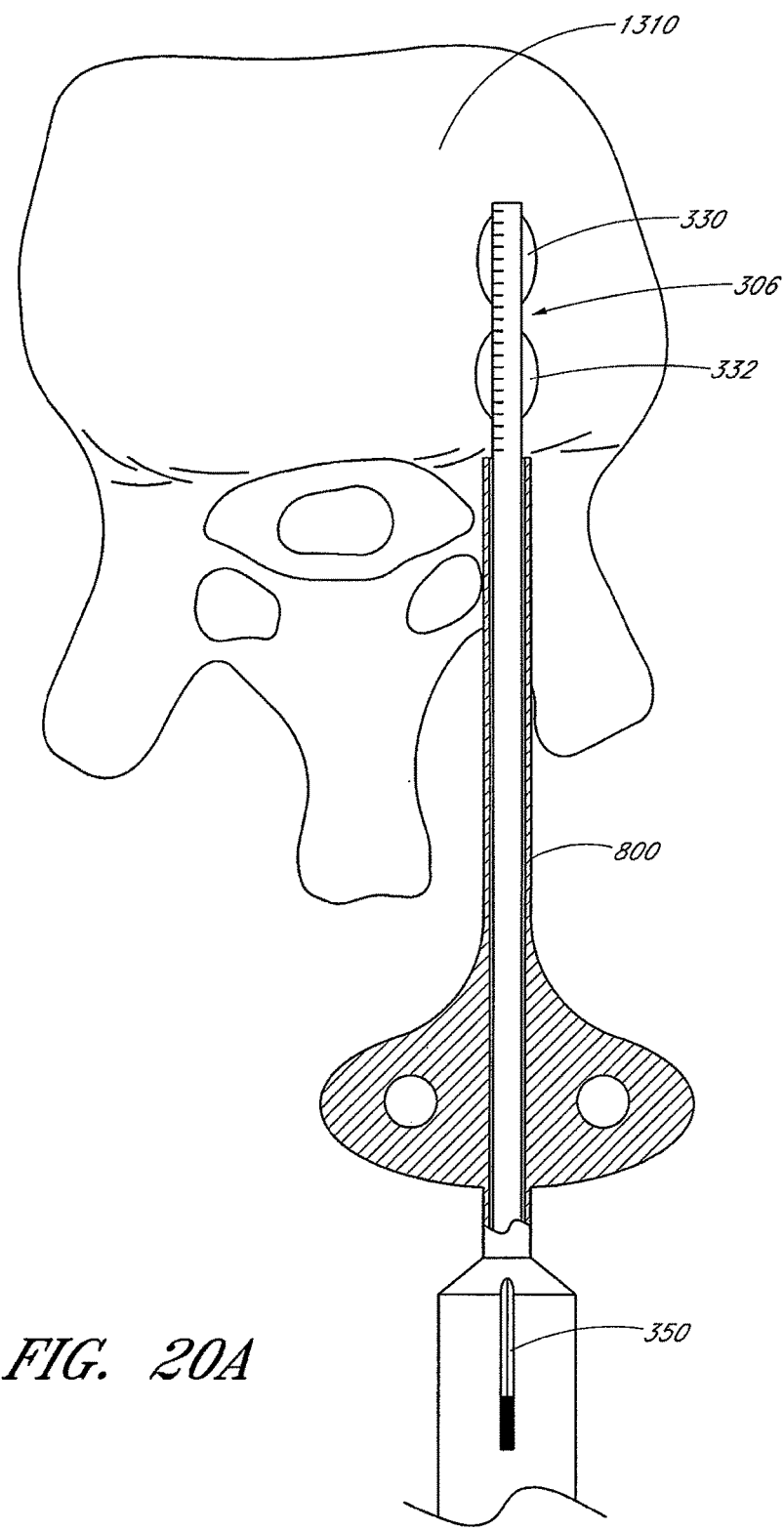
FIGS. 20A-20C show stages in a method of creating a cavity using a steerable and curvable injector with a plurality of cavity creation elements during a vertebroplasty procedure in accordance with the invention.
Figure 20B:
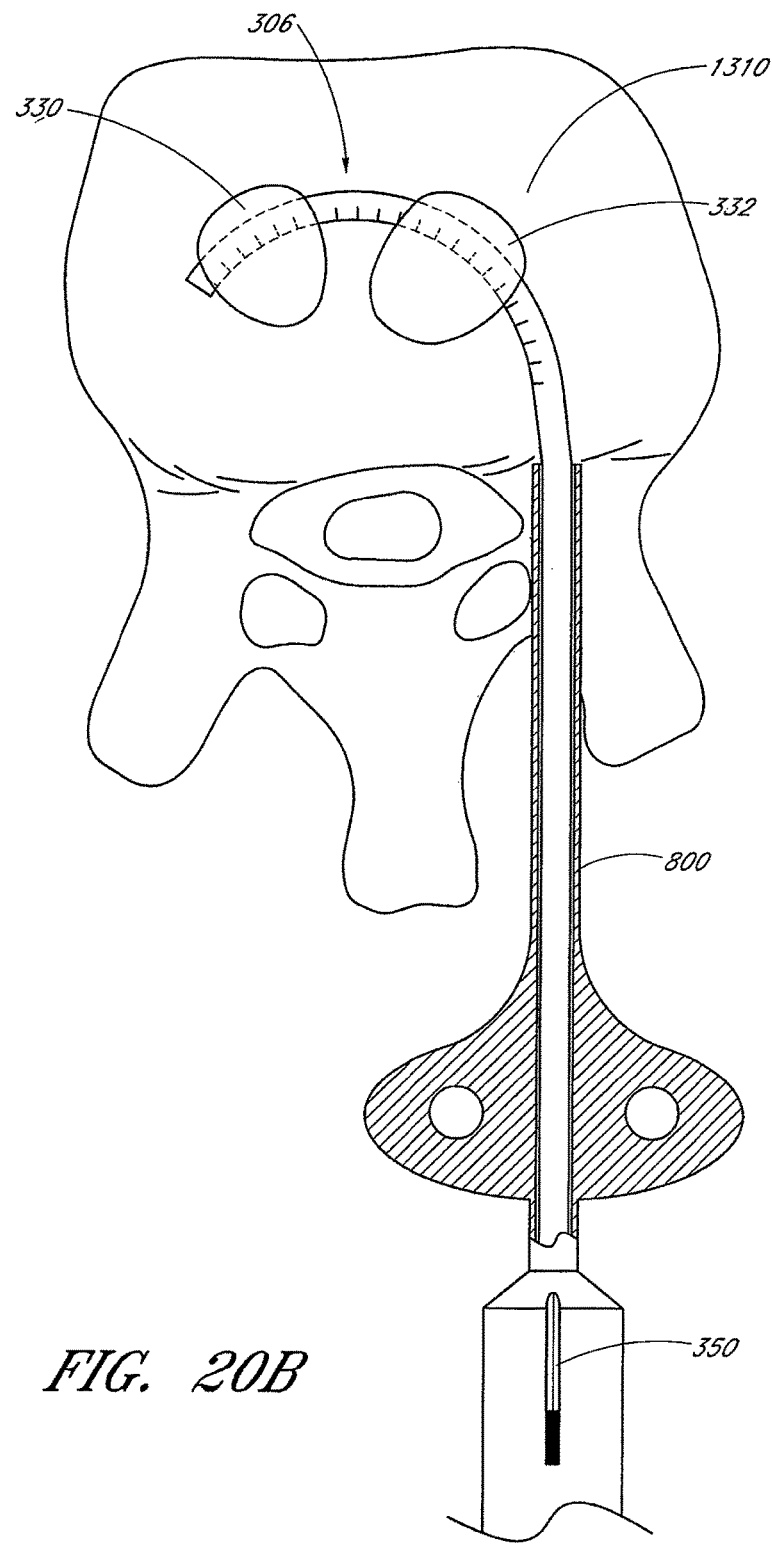
Figure 20C:
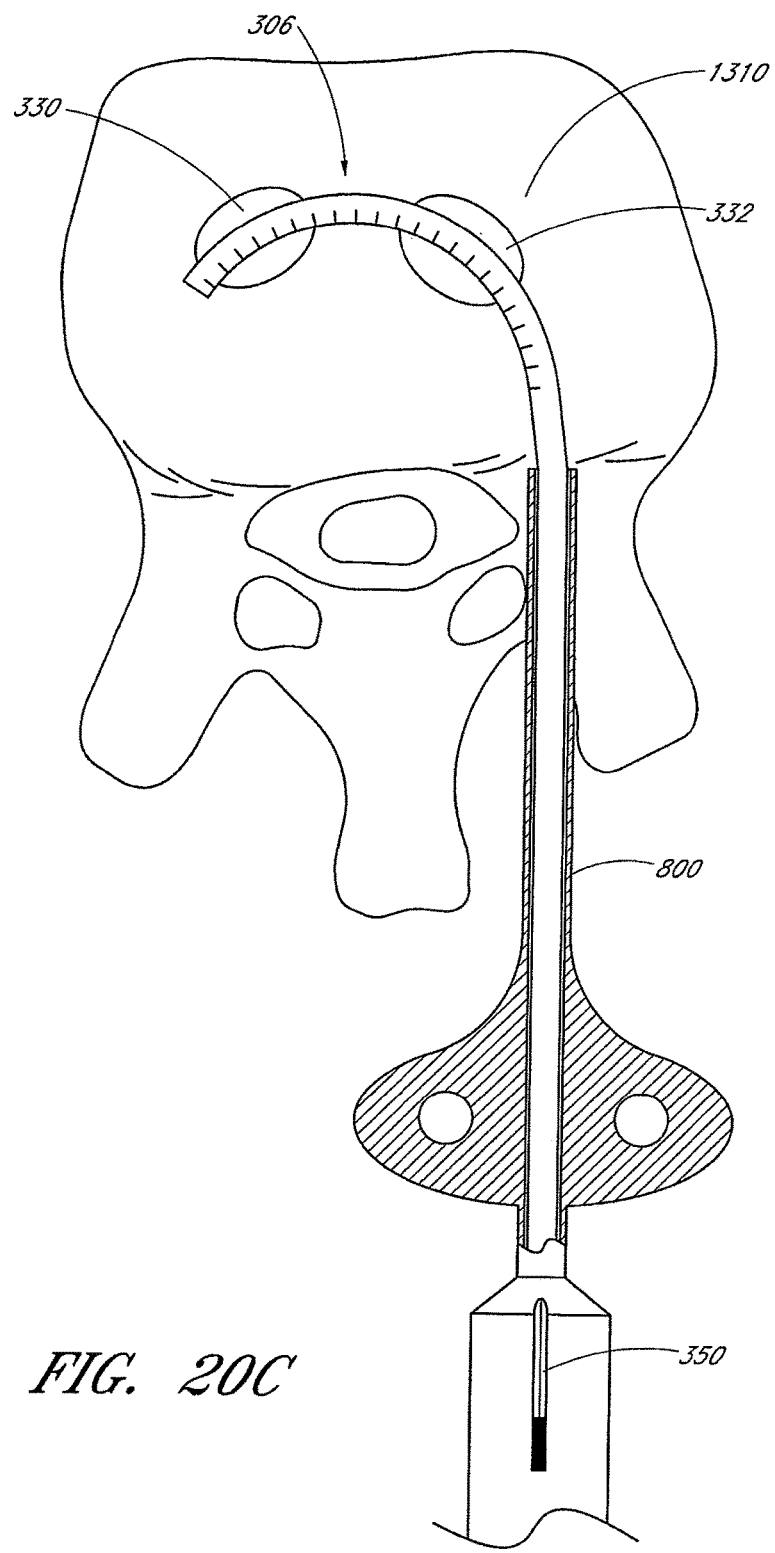

A method of using the steerable and curvable injection system described, for example, in FIGS. 17C-17D will now be described. Various components of the injector 300 are not illustrated for clarity purposes. The interior of the vertebral body 1310 can be first accessed via a unipedicular approach as described and illustrated in connection with FIGS. 19A-B. Next, the steerable and curvable injector 300 having first balloon 330 and second balloon 332 thereon is inserted through an introducer 800 into the interior of the vertebral body 1310 with the distal deflectable section 306 in a relatively straightened configuration, as shown schematically in FIG. 20A. In some embodiments, the injector 300 also has a retractable outer sheath 340 actuatable by a controller 350 on the handpiece 360 to protect the balloons 330, 332 from damage during introduction of the injector 300 into the interior of the vertebral body 1310. The injector 300 can then be laterally deflected, rotated, and or proximally retracted or distally advanced to position the injector at any desired site as previously described in the application, and illustrated schematically in FIG. 20B. The radius can be adjusted by means of an adjustment control, such as a knob on the proximal end of the device as previously described. The first balloon 330 and second balloon 332 can then be inflated simultaneously as illustrated in FIG. 20C or sequentially as previously described. In some embodiments, only one of the balloons may need to be inflated depending on the size of the cavity desired to be created. Injection of the cement media can proceed at any desired time as previously described, such as, for example, following deflation of one or both balloons.

Figure 21A:
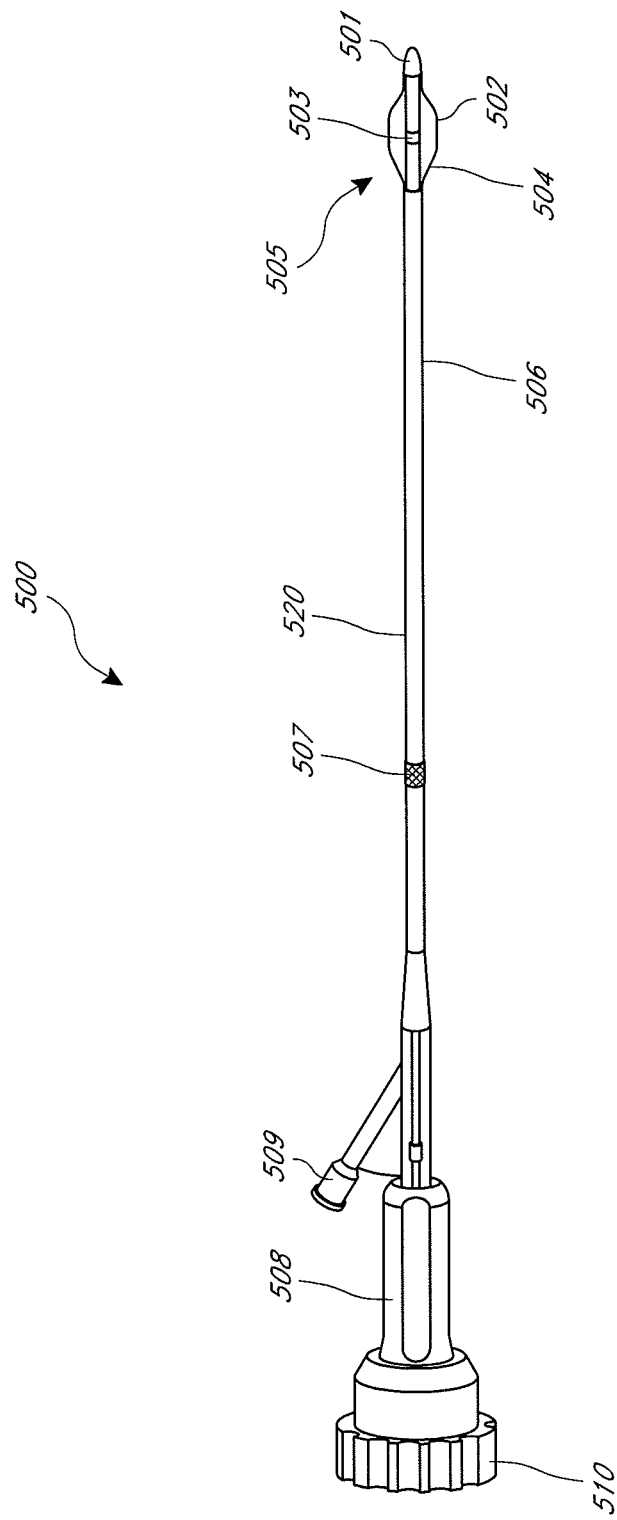

FIG. 21A illustrates an embodiment of a steerable cavity creation device 500. The device 500 includes a proximal handle 508, a shaft portion 520, and a steerable and curvable distal end 505 including a distal tip 501. The proximal handle 508 includes a deflection control 510, such as a rotatable knob, that when actuated in an appropriate direction causes a tensile or compression force to be applied on the distal end 505, causing it to move in an appropriate direction (e.g., opposite or toward the injection port 509). One, two, or more input ports 509 extend from the proximal handle 508 for example, to inject a fluid (e.g., a liquid or gas) to expand the expandable member 502, such as inflating a balloon. Input port 509 is operably connected to a lumen within the shaft portion 520, which is in turn operably connected to balloon 502. The input port 509 could be spaced apart distally with respect to the deflection control 510 as illustrated, or proximally with respect to the deflection control 510 with respect to a longitudinal axis of the device 500 in some embodiments. The input port 509 could be coaxial with, or have a longitudinal axis that is offset from the longitudinal axis of the device 500, such as at an angle of between about 0° and 90°, between about 15° and 60°, between about 15° to 45°, about 90°, or about 30° in some embodiments. The device 500 can include an inner member 504 such as a tubing, and an outer member 506, such as a shaft. Outer shaft 506 can include indicia, such as an insertion marker 507 in shaft section 520 that may be radiopaque. Marker 507 can assist in indicating when the balloon 502 has distally cleared the access introducer/cannula and is in a space conducive for expansion of the balloon 502. The distal end of the device 505 includes one, two, or more cavity creation structures 502, which in some embodiment is an expandable member 502. Other non-expandable cavity creation structures such as one or a combination of cutting elements, or energy-based cavity creation structures involving RF, microwave, optical, thermal, or cryoablation elements could also be utilized.

The expandable member 502 could be a balloon in some embodiments. A radiopaque marker 503 may assist in confirming the position of the balloon prior to expansion at the appropriate target location to create a cavity. The radiopaque marker 503 could be, for example, a marker band partially or completely circumferentially surrounding a portion of the shaft at the distal end 505 of the device 500, such as at the axial midpoint of the balloon 502 for example. Distal tip 501 could be either blunt or sharp, and in some embodiments can include a cutting element to further assist in cavity creation.

Figure 21B:
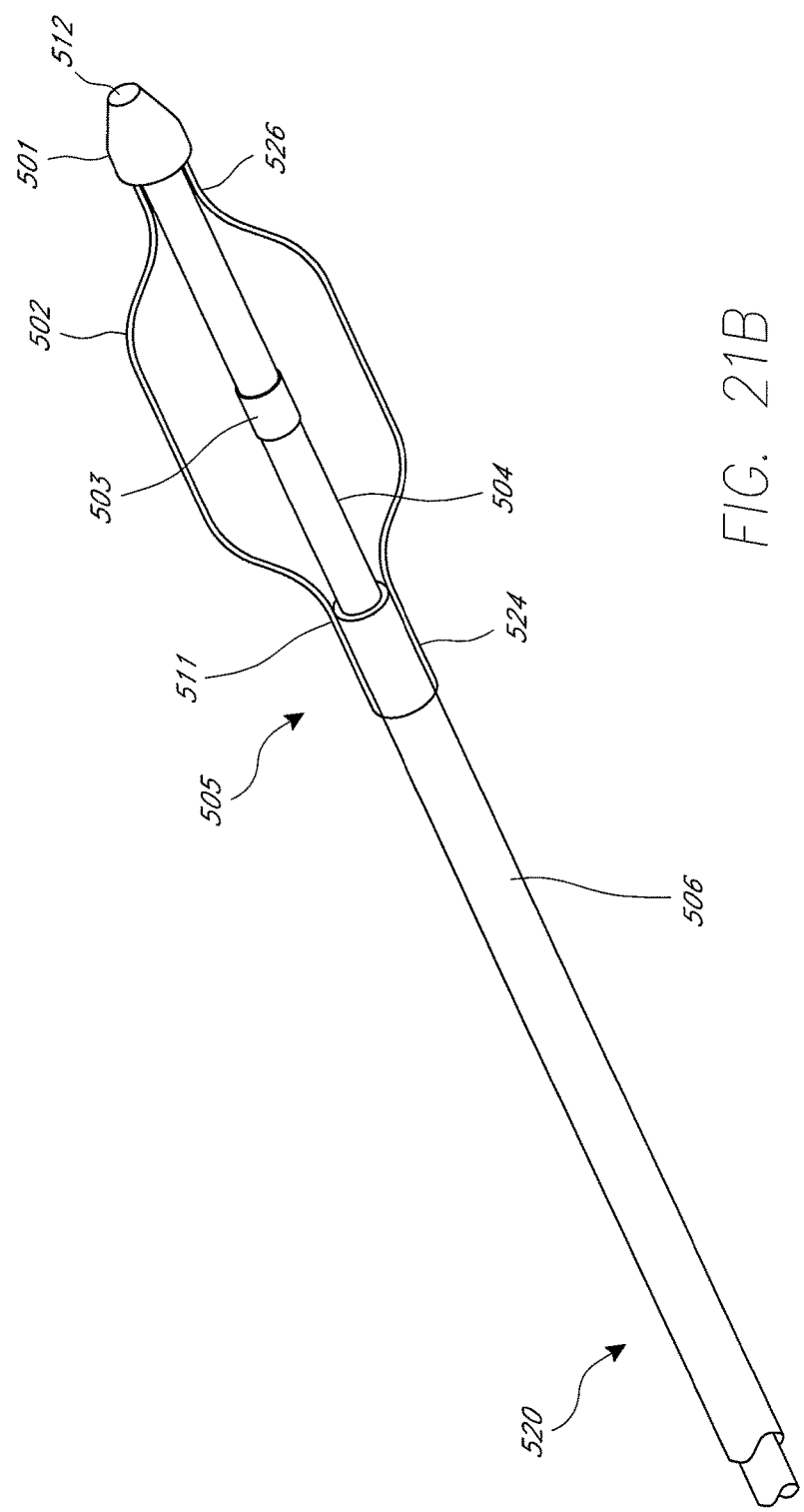

FIG. 21B illustrates a close-up view of the distal end 505 of the device. As shown, the proximal neck 524 of the balloon 502 is bonded or otherwise attached to the outer shaft 506. The distal neck 526 of the balloon 502 is bonded or otherwise attached to inner tubing 504. In order to expand the balloon, a fluid is injected through the input port 509 (shown in FIG. 50A) through an annular space 511 between the inner tubing 504 and the outer shaft 506. The effect of the balloon bond configuration is that the balloon 502 will expand generally radially outwardly without or substantially without expansion in the axial direction. The balloon could be either constrained or unconstrained, and have features, for example, as previously described.

Also shown is the distal tip 501, which could be a welded tip 512 having a closed distal end in some embodiments. The welded tip 512 can advantageously hold the distal neck 526 of the balloon 502 to improve bond strength and holds the balloon bond stationary when inflated.

In some embodiments, instead of a closed distal end the distal tip could include one, two, or more distal or side-facing exit ports connected via a lumen, e.g., a central lumen of the inner tubing 504, to a media input port for delivery of a media, such as a bone cement, to the interior of a bone, such as a cavity. Alternatively, the cavity creating device 500 can be withdrawn after cavity creation, and a separate steerable injection device then inserted for delivery of the media as described further below.

Figure 21C:
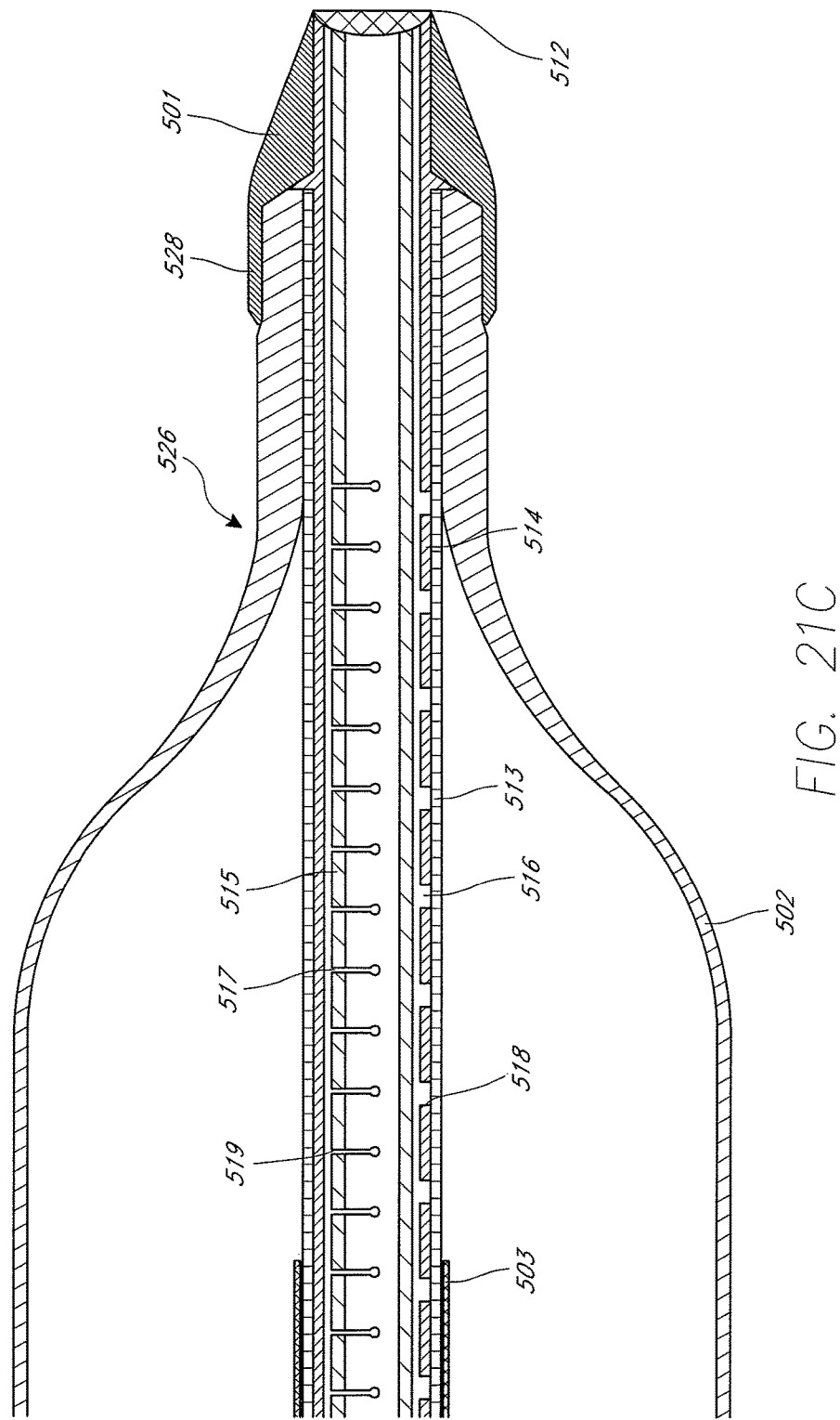

FIG. 21C is a cross-section of the distal end 505 of the device 500 illustrated in FIG. 21B. Shown is an inner hypotube 515 having slots 519 present within an inner lumen of an outer hypotube 514, which also has slots 518. In some embodiments, the length of the inner hypotube 515 zone having slots 519 is the same or substantially the same as the length of the outer hypotube 514 zone having slots 518. The slots 519 of the inner hypotube 515 can, in some embodiments, be spaced apart, such as between about 120° and about 240°, or about 180° apart from the slots 518 of the outer hypotube 514. The distal ends of the inner hypotube 515 and the outer hypo tube 514 can be attached, such as by welding at 512 at the distal tip 501 of the device 500. The inner hypotube 515 and outer hypotube 514 can be made of any appropriate material with sufficient column strength to navigate cancellous bone, such as a metal such as stainless steel, or nitinol for example. The inner hypotube 515 and outer hypotube 514 could be made of the same or different materials. Either or both hypotubes 515, 514 includes slots 519, 518 that could be, for example, laser-cut. The slots 519, 518 could be any desired wall pattern, such as simply transverse to the longitudinal axis of the hypotube, or in a chevron pattern in other embodiments. Inner tubing 504 at least partially circumscribing the outer hypotube 514 serves to seal the balloon chamber. Radiopaque marker band 503 can be positioned either inside or outside of the balloon chamber in some embodiments, for visualization during fluoroscopy. The proximal end 528 of the distal tip 501 of the device 500 is positioned over the distal neck 526 of the balloon 502 to prevent or substantially prevent the balloon 502 from elongating distally when inflated. The proximal end 528 of the distal tip 501 of the device also constrains the bond section to improve bond integrity.

FIG. 21D illustrates schematically the distal end 505 of the device 500, highlighting the inner hypotube 515-outer hypotube 514 configuration in an undeflected configuration where a longitudinal axis of the distal end 505 is coaxial with, or at least parallel to the longitudinal axis of the device 500. The number of inner hypotube slots 519 can be less than, equal to, or greater than the number of outer hypotube slots 518. In some embodiments, the number of inner hypotube slots 519 is at least about 5%, 10%, 15%, 20%, 25%, 30%, 40%, 50%, 75%, 100%, or more than the number of outer hypotube slots 518. A dimension, such as the axial width 516 of the outer hypotube slots 518 can be, for example, less than, equal to, or greater than the axial width 517 of the inner hypotube slots 519. In some embodiments, the axial width 516 of outer hypotube slots 518 is at least about 5%, 10%, 15%, 20%, 25%, 30%, 40%, 50%, 75%, 100%, 150%, 200%, 250%, 300% greater than the axial width 517 of the inner hypotube slots 519. In some embodiments, the axial width 516 of the outer hypotube slots 518 is between about 1.5× and 3×, or about 2× of the axial width 517 of the inner hypotube slots 519. In some embodiments, the width 517 of the inner hypotube slot 519 is between about 0.001" and about 0.005", between about 0.002" and about 0.006", or about or at least about 0.002". The width 517 of the inner hypotube is in some embodiments sufficiently large to allow for the desired degree of deflection, but sufficiently small such that the structural integrity of the inner hypotube 515 is not sufficiently impaired.

Figure 21E:
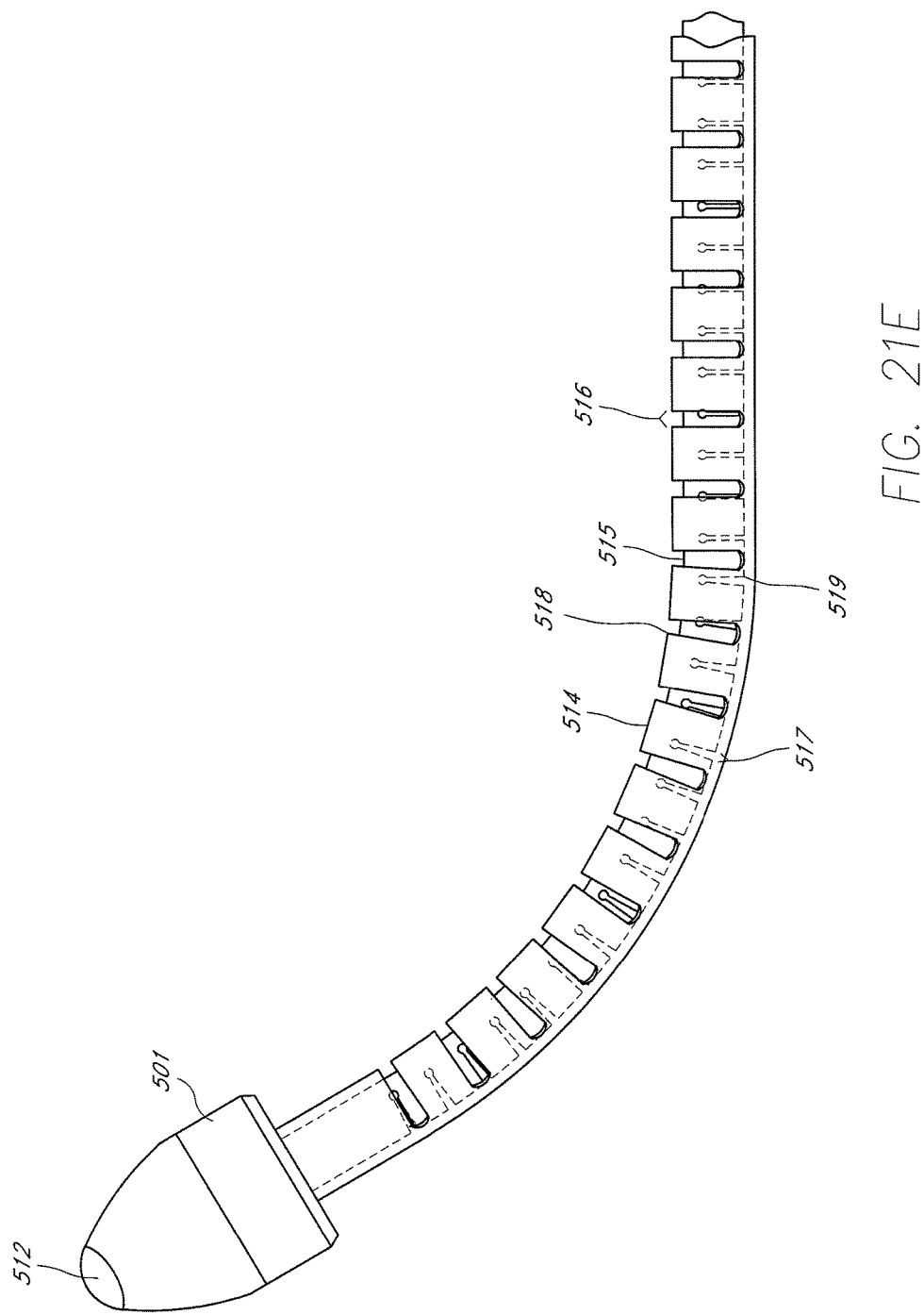

FIG. 21E illustrates distal end 505 of the device 500, highlighting the inner hypotube 515-outer hypotube 514 configuration in a deflected configuration. In some embodiments, the device can be configured to deflect from the longitudinal axis of the device 500 by at least about 50°, 60°, 70°, 80°, 90°, 100°, or more, or between about 70° and about 100° in some embodiments. When a tensile force is applied to the inner hypotube 515 while the outer hypotube 514 is immobilized or held stationary, a compression force will thus be applied to the outer hypo tube 514 which will bend both the inner hypo tube 515 and the outer hypo tube 514 in the direction of the openings of the outer hypotube slots 518 as shown. As the deflectable distal end 505 of the device deflects, the axial width 516 of the outer hypotube slots 518 decreases and the axial width 517 of the inner hypotube slots 519 increases in the deflected zone. When a compression force is applied to the inner hypotube 515 the axial width 517 of the inner hypotube slots 519 decreases and the axial width 516 of the outer hypotube slots 518 increases, causing the distal end 505 of the device 500 to deflect in a direction opposite of the direction of the openings of the outer hypotube slots 518. The distal end of either or both of the inner hypotube 515 and outer hypotube 514 could be operably connected via one, two, or more pullwires (e.g., two pullwires positioned 180° circumferentially apart along a sidewall (such as oriented against or opposite the slots) of either the inner hypotube 515 and/or outer hypotube 514 to the deflection control 510 proximally) to create the desired tension or compression forces when the deflection control is moved in an appropriate direction (e.g., clockwise or counterclockwise). In some embodiments, distal pullwires are not required, and a tensile or compression force can be transmitted via a mechanism to the proximal end of one or more of the inner hypotube 515 or outer hypotube 514.

In other words, the device could have a distal end 505 having a first hypotube having a first plurality of slots and a second hypotube having a second plurality of slots, the first hypotube coaxially aligned with the second hypotube, the second plurality of slots oriented in a direction opposite to that of the first plurality of slots. The axial width of the first plurality of slots can be greater than, e.g., about 2× greater than, the axial width of the second plurality of slots. The number of slots of the second plurality of slots can be greater than the number of slots of the first plurality of slots.

Embodiments of the cavity creation device 500 described in connection with FIGS. 21A-21E above can be utilized with methods similar to those described and illustrated, for example, in connection with FIGS. 19A-20C above. Access to a bone, such as a vertebral body, can be achieved as described above, e.g., by utilizing a stylet to perforate a lumen, and then inserting an introducer/cannula through the lumen as described in connection with FIGS. 19A-B above. The cavity creation device 500 can then be inserted through the introducer/cannula and into the vertebrae. The entire interior of the target bone (e.g., the vertebral body) can be laterally deflected, rotated, and/or proximally retracted or distally advanced to position the cavity creation structure at any desired site. The radius of the distal end 505 can be adjusted by means of a deflection control, such as a knob at the proximal end of the device as previously described. Once the steerable and curvable cavity creation device 500 has been positioned as desired, either linearly or deflected, such as illustrated in FIG. 19C for example, the cavity creation structure is used to form or enlarge a cavity, such as by introducing inflation media under pressure into an inflatable balloon. The balloon is thereafter reduced in cross-sectional configuration, such as by aspirating inflation media from the inflatable balloon 322, and the cavity creation device 500 is withdrawn from the cavity. Cavity creation device 500 can be used to form one, two, three, or more cavities. An injector, such as a steerable curvable injector as previously described, for example, can be inserted through the introducer/cannula and a media such as bone cement injected into the cavity as described, for example, in connection with FIGS. 19C-19E above.

The hypotube and slot configurations, distal tip configurations, and other features of a steerable device as described and illustrated in connection with FIGS. 21A-21E can be applied, for example to any of the steerable and curvable injectors shown in any of the preceding figures, including those without a closed distal end, such as injectors having distally, side-facing, or angled exit ports for delivery of media, such as a bone cement, to a cavity of a bone. For example, features of embodiments of FIGS. 21A-21E or variations thereof can be utilized with a combination steerable and curvable injector having a cavity forming structure, such as described in connection with FIG. 16A above.

While described herein primarily in the context of vertebroplasty, one of ordinary skill in the art will appreciate that the disclosed injection system can be used or modified in a wide range of clinical applications, such as, for example, other orthopedic applications such as kyphoplasty, treatment of any other bones, pulmonary, cardiovascular, gastrointestinal, gynecological, or genitourinary applications. While this invention has been particularly shown and described with references to embodiments thereof, it will be understood by those skilled in the art that various changes in form and details may be made therein without departing from the scope of the invention. For all of the embodiments described above, the steps of the methods need not be performed sequentially and the individual components of the devices may be combined permanently or be designed for removable attachment at the clinical site. Additionally, the skilled artisan will recognize that any of the above-described methods can be carried out using any appropriate apparatus. Further, the disclosure herein of any particular feature in connection with an embodiment can be used in all other disclosed embodiments set forth herein. Thus, it is intended that the scope of the present invention herein disclosed should not be limited by the particular disclosed embodiments described above.

What is claimed is:

1. A steerable cavity creation device having a proximal end and a distal end, comprising:
   an outer shaft having a proximal end and a distal end, an inner tubing extending therethrough, a first hypotube diposed within the inner tubing, and a second hypotube disposed within the first hypotube;
   a deflectable zone on the distal end of the device, deflectable through an angular range, the deflectable zone having a proximal portion and a distal portion, wherein the first hypotube has a distal zone having a first plurality of Slots, and the second hypotube has a distal zone having a second plurality of slots, herein the first plurality of slots is oriented 180 degrees circumferentially apart from the second plurality of slots, wherein the first hypotube has a first longitudinal axis extending from the proximal end to the proximal portion of the deflectable zone, wherein the deflectable zone is movable from a first substantially straight configuration in an a unstressed state to a second deflected configuration;
   a deflection controller on the proximal end of the device, wherein the deflection controller is actuated by rotation about the first longitudinal axis of the first hypotube, wherein upon rotation of the deflection controller a proximally directed force is exerted on a movable actuator attached to the second hypotube to actively change the curvature of the deflectable zone, wherein the first hypotube is held stationary when the movable actuator applies a force to the second hypotube;
   an input port positioned distally on the second hypotube relative to the deflection controller;
   a cavity creating element carried by the deflectable zone, wherein the cavity creating element comprises a balloon having a balloon chamber, wherein the balloon has as proximal neck and a distal neck, wherein the proximal neck is attached to the distal end of the outer shaft and the distal neck is attached to the inner tubing, wherein the inner tubing is configured to seal the balloon chamber; and
   a distal tip positioned over the distal neck of the balloon and over a distal end of the first hypotube and a distal end of the second hypotube.

2. The cavity creation device of claim 1, wherein the first plurality of slots each have an axial width that is between about 1.5x and 3x of the axial width of each of the second plurality of slots.

3. The cavity creation deice of claim 1, wherein the axial width of each of the second plurality of slots is between about .001" and, 005".

4. The cavity creation device of claim 1, wherein the total distance of the second plurality of slots is at least the number of the first plurality of slots.

5. The cavity creation device of claim 1, wherein the device has a closed distal end.

6. The cavity creation device of claim 1, wherein the first hypotube and the second hypotube are comprised of metal.

7. The cavity creation device of claim 6, wherein the distal end of the first hypotube and the distal end of the second hypotube are attached to each other at the distal tip.

8. The cavity creation device of claim 7, wherein the distal end of the first hypotube and the distal end of the second hypotube are attached to each other at the distal tip by welding.

* * * * *